(12) United States Patent
Brake et al.

(10) Patent No.: US 10,426,782 B2
(45) Date of Patent: Oct. 1, 2019

(54) PHARMACEUTICAL FORMULATIONS OF A PAN-RAF KINASE INHIBITOR AND PROCESSES FOR THEIR PREPARATION

(71) Applicant: Millennium Pharmaceuticals, Inc., Cambridge, MA (US)

(72) Inventors: Rachael L. Brake, Natick, MA (US); Viviana Bozon, West Newton, MA (US); Ching-Kuo J. Chow, Littleton, MA (US); James C. Dinunzio, Bridgewater, NJ (US); Katherine M. Galvin, Newton, MA (US); Karuppiah Kannan, Newton, MA (US); Yuki Kodono, Osaka (JP); Qunli Xu, Wellesley, MA (US)

(73) Assignee: MILLENNIUM PHARMACEUTICALS, INC., Cambridge, MA (US)

( * ) Notice: Subject to any disclaimer, the term of this patent is extended or adjusted under 35 U.S.C. 154(b) by 89 days.

(21) Appl. No.: 15/128,714

(22) PCT Filed: Mar. 26, 2015

(86) PCT No.: PCT/US2015/022792
§ 371 (c)(1),
(2) Date: Sep. 23, 2016

(87) PCT Pub. No.: WO2015/148828
PCT Pub. Date: Oct. 1, 2015

(65) Prior Publication Data
US 2017/0173033 A1   Jun. 22, 2017

Related U.S. Application Data

(60) Provisional application No. 62/048,527, filed on Sep. 10, 2014, provisional application No. 61/970,595, filed on Mar. 26, 2014.

(30) Foreign Application Priority Data

Mar. 25, 2015 (PK) .................... 162/2015
Mar. 25, 2015 (UY) ........................ 36.046

(51) Int. Cl.
*A61K 31/541* (2006.01)
*A61K 9/14* (2006.01)
*A61K 9/20* (2006.01)
*C12Q 1/6886* (2018.01)
*A61K 9/28* (2006.01)

(52) U.S. Cl.
CPC ............ *A61K 31/541* (2013.01); *A61K 9/14* (2013.01); *A61K 9/146* (2013.01); *A61K 9/20* (2013.01); *A61K 9/2027* (2013.01); *A61K 9/2054* (2013.01); *A61K 9/28* (2013.01); *C12Q 1/6886* (2013.01); *A61K 9/2866* (2013.01); *C12Q 2600/106* (2013.01); *C12Q 2600/156* (2013.01)

(58) Field of Classification Search
CPC ........ A61K 31/541; A61K 9/14; A61K 9/146; A61K 9/20; A61K 9/2027; A61K 9/2054; A61K 9/28; A61K 9/2866
See application file for complete search history.

(56) References Cited

U.S. PATENT DOCUMENTS

| | | | |
|---|---|---|---|
| 5,741,519 A | 4/1998 | Rosenberg et al. | |
| 2005/0220865 A1 | 10/2005 | Koleng et al. | |
| 2008/0292702 A1 | 11/2008 | Woo et al. | |
| 2010/0143481 A1 | 6/2010 | Shenoy et al. | |
| 2010/0209495 A1 | 8/2010 | Li et al. | |

FOREIGN PATENT DOCUMENTS

| WO | WO-2008016260 A1 * | 2/2008 | ............. A61K 9/146 |
|---|---|---|---|
| WO | WO 2009/006389 A2 | 1/2009 | |
| WO | WO 2013/144923 A1 | 10/2013 | |

OTHER PUBLICATIONS

Maniruzzaman et al., "Dissolution enhancement of poorly water-soluble APIs processed by holt-melt extrusion using hydrophilic polymers," Drug Development and Industrial Pharmacy (2013); 39(2): pp. 218-227 (published online Mar. 28, 2012).*

Macauley, D. et al., "American Association for Cancer Research (AACR) 103rd Annual Meeting Chicago, Illinois, USA, Mar. 31-Apr. 4, 2012," Drugs of the Future, Prous Science, ES, vol. 37, No. 6, Jun. 1, 2012, pp. 451-455.

Ziai, J. and Hui, P., "*BRAF* mutation testing in clinical practice," *Expert Review of Molecular Diagnostics*, Expert Reviews Ltd., GB, vol. 12, No. 2, Mar. 1, 2012, pp. 127-138.

International Search Report for International Patent Application No. PCT/US2015/022792, European Patent Office, Rijswijk, The Netherlands, dated Jun. 22, 2015.

* cited by examiner

*Primary Examiner* — Sreenivasan Padmanabhan
*Assistant Examiner* — Jody L Karol
(74) *Attorney, Agent, or Firm* — Sterne, Kessler, Goldstein & Fox P.L.L.C.

(57) ABSTRACT

The invention relates to a pharmaceutical composition comprising Compound 1 or a pharmaceutically acceptable salt thereof for the treatment of cancer and a process for its preparation. The invention also relates to administering the pharmaceutical composition to a patient according to an intermittent dosing regimen.

6 Claims, 9 Drawing Sheets
Specification includes a Sequence Listing.

SEQUENCE LISTING

<160> NUMBER OF SEQ ID NOS: 6

<210> SEQ ID NO 1
<211> LENGTH: 2949
<212> TYPE: DNA
<213> ORGANISM: Homo sapiens

<400> SEQUENCE: 1

```
cgcctccctt cccctcccc gcccgacagc ggccgctcgg gccccggctc tcggttataa      60
gatggcggcg ctgagcggtg gcggtggtgg cggcgcggag ccgggccagg ctctgttcaa     120
cggggacatg gagcccgagg ccggcgccgg cgccggcgcc gcggcctctt cggctgcgga    180
ccctgccatt ccggaggagg tgtggaatat caaacaaatg attaagttga cacaggaaca    240
tatagaggcc ctattggaca aatttggtgg ggagcataat ccaccatcaa tatatctgga    300
ggcctatgaa gaatacacca gcaagctaga tgcactccaa caaagagaac aacagttatt    360
ggaatctctg gggaacggaa ctgattttc tgtttctagc tctgcatcaa tggataccgt    420
tacatcttct tcctcttcta gcctttcagt gctaccttca tctctttcag tttttcaaaa    480
tcccacagat gtggcacgga gcaaccccaa gtcaccacaa aaacctatcg ttagagtctt    540
cctgcccaac aaacagagga cagtggtacc tgcaaggtgt ggagttacag tccgagacag    600
tctaaagaaa gcactgatga tgagaggtct aatcccagag tgctgtgctg tttacagaat    660
tcaggatgga gagaagaaac caattggttg ggacactgat atttcctggc ttactggaga    720
agaattgcat gtggaagtgt tggagaatgt tccacttaca acacacaact ttgtacgaaa    780
aacgtttttc accttagcat tttgtgactt ttgtcgaaag ctgcttttcc agggtttccg    840
ctgtcaaaca tgtggttata aatttcacca gcgttgtagt acagaagttc cactgatgtg    900
tgttaattat gaccaacttg atttgctgtt tgtctccaag ttctttgaac caccccaat    960 accacaggaa gaggcgtcct tagcagagac tgccctaaca tctggatcat ccccttccgc   1020
acccgcctcg gactctattg ggcccaaat tctcaccagt ccgtctcctt caaaatccat   1080
tccaattcca cagcccttcc gaccagcaga tgaagatcat cgaaatcaat tgggcaacg   1140 agaccgatcc tcatcagctc ccaatgtgca tataaacaca atagaacctg tcaatattga   1200
tgacttgatt agagaccaag gatttcgtgg tgatggagga tcaaccacag gtttgtctgc   1260 tacccccct gcctcattac ctggctcact aactaacgtg aaagccttac agaaatctcc   1320
```

```
aggacctcag cgagaaagga agtcatcttc atcctcagaa gacaggaatc gaatgaaaac    1380
acttggtaga cgggactcga gtgatgattg ggagattcct gatgggcaga ttacagtggg    1440
acaaagaatt ggatctggat catttggaac agtctacaag ggaaagtggc atggtgatgt    1500
ggcagtgaaa atgttgaatg tgacagcacc tacacctcag cagttacaag ccttcaaaaa    1560
tgaagtagga gtactcagga aaacacgaca tgtgaatatc ctactcttca tgggctattc    1620
cacaaagcca caactggcta ttgttaccca gtggtgtgag ggctccagct tgtatcacca    1680
tctccatatc attgagacca aatttgagat gatcaaactt atagatattg cacgacagac    1740
tgcacagggc atggattact tacacgccaa gtcaatcatc cacagagacc tcaagagtaa    1800
taatatattt cttcatgaag acctcacagt aaaaataggt gattttggtc tagctacagt    1860
gaaatctcga tggagtgggt cccatcagtt tgaacagttg tctggatcca ttttgtggat    1920
ggcaccagaa gtcatcagaa tgcaagataa aaatccatac agctttcagt cagatgtata    1980
tgcatttgga attgttctgt atgaattgat gactggacag ttaccttatt caaacatcaa    2040
caacagggac cagataattt ttatggtggg acgaggatac ctgtctccag atctcagtaa    2100
ggtacggagt aactgtccaa aagccatgaa gagattaatg gcagagtgcc tcaaaaagaa    2160
aagagatgag agaccactct ttccccaaat tctcgcctct attgagctgc tggcccgctc    2220
attgccaaaa attcaccgca gtgcatcaga accctccttg aatcgggctg gtttccaaac    2280
agaggatttt agtctatatg cttgtgcttc tccaaaaaca cccatccagg caggggata    2340 tggtgcgttt cctgtccact gaaacaaatg agtgagagag ttcaggagag tagcaacaaa    2400
aggaaaataa atgaacatat gtttgcttat atgttaaatt gaataaaata ctctcttttt    2460
ttttaaggtg aaccaaagaa cacttgtgtg gttaaagact agatataatt tttccccaaa    2520
ctaaaattta tacttaacat tggattttta acatccaagg gttaaaatac atagacattg    2580
ctaaaaattg gcagagcctc ttctagaggc tttactttct gttccgggtt tgtatcattc    2640
acttggttat tttaagtagt aaacttcagt ttctcatgca acttttgttg ccagctatca    2700
catgtccact agggactcca gaagaagacc ctaccatgc ctgtgtttgc aggtgagaag    2760
ttggcagtcg gttagcctgg gttagataag gcaaactgaa cagatctaat ttaggaagtc    2820
agtagaattt aataattcta ttattattct taataatttt tctataacta tttcttttta    2880
taacaatttg gaaaatgtgg atgtcttta tttccttgaa gcaataaact aagtttcttt    2940
ttataaaaa                                                            2949
```

<210> SEQ ID NO 2
<211> LENGTH: 2301
<212> TYPE: DNA
<213> ORGANISM: Homo sapiens

<400> SEQUENCE: 2

```
atggcggcgc tgagcggtgg cgtggtggc ggcgcggagc cgggccaggc tctgttcaac       60
ggggacatgg agcccgaggc cggcgccggc gccggcgccg cggcctcttc ggctgcggac     120
cctgccattc cggaggaggt gtggaatatc aaacaaatga ttaagttgac acaggaacat     180
atagaggccc tattggacaa atttggtggg agcataatcc accatcaat atatctggag     240 gcctatgaag aatacaccag caagctagat gcactccaac aaagagaaca acagttattg     300
gaatctctgg ggaacggaac tgattttttct gtttctagct ctgcatcaat ggataccgtt     360
acatcttctt cctcttctag cctttcagtg ctaccttcat ctctttcagt tttcaaaat     420
```

```
cccacagatg tggcacggag caaccccaag tcaccacaaa aacctatcgt tagagtcttc      480
ctgcccaaca acagaggac  agtggtacct gcaaggtgtg gagttacagt ccgagacagt      540
ctaaagaaag cactgatgat gagaggtcta atcccagagt gctgtgctgt ttacagaatt      600
caggatggag agaagaaacc aattggttgg gacactgata tttcctggct tactggagaa      660
gaattgcatg tggaagtgtt ggagaatgtt ccacttacaa cacacaactt tgtacgaaaa      720
acgtttttca ccttagcatt tgtgactttt tgtcgaaagc tgcttttcca gggtttccgc      780
tgtcaaacat gtggttataa atttcaccag cgttgtagta cagaagttcc actgatgtgt      840
gttaattatg accaacttga tttgctgttt gtctccaagt tctttgaaca ccacccaata      900
ccacaggaag aggcgtcctt agcagagact gccctaacat ctggatcatc cccttccgca      960
cccgcctcgg actctattgg gccccaaatt ctcaccagtc cgtctccttc aaaatccatt     1020
ccaattccac agcccttccg accagcagat gaagatcatc gaaatcaatt tgggcaacga     1080
gaccgatcct catcagctcc caatgtgcat ataaacacaa tagaacctgt caatattgat     1140
gacttgatta gagaccaagg atttcgtggt gatggaggat caaccacagg tttgtctgct     1200
accccccctg cctcattacc tggctcacta actaacgtga aagccttaca gaaatctcca     1260
ggacctcagc gagaaaggaa gtcatcttca tcctcagaag acaggaatcg aatgaaaaca     1320
cttggtagac gggactcgag tgatgattgg gagattcctg atgggcagat tacagtggga     1380
caaagaattg gatctggatc atttggaaca gtctacaagg gaaagtggca tggtgatgtg     1440
gcagtgaaaa tgttgaatgt gacagcacct acacctcagc agttacaagc cttcaaaaat     1500
gaagtaggag tactcaggaa aacacgacat gtgaatatcc tactcttcat gggctattcc     1560
acaaagccac aactggctat tgttacccag tggtgtgagg gctccagctt gtatcaccat     1620
ctccatatca ttgagaccaa atttgagatg atcaaactta tagatattgc acgacagact     1680
gcacagggca tggattactt acacgccaag tcaatcatcc acagagacct caagagtaat     1740
aatatatttc ttcatgaaga cctcacagta aaaataggtg attttggtct agctacagtg     1800
aaatctcgat ggagtgggtc ccatcagttt gaacagttgt ctggatccat tttgtggatg     1860
gcaccagaag tcatcagaat gcaagataaa atcccataca gctttcagtc agatgtatat     1920
gcatttggaa ttgttctgta tgaattgatg actggacagt taccttattc aaacatcaac     1980
aacagggacc agataatttt tatggtggga cgaggatacc tgtctccaga tctcagtaag     2040
gtacggagta actgtccaaa agccatgaag agattaatgg cagagtgcct caaaaagaaa     2100
agagatgaga gaccactctt tccccaaatt ctcgcctcta ttgagctgct ggcccgctca     2160
ttgccaaaaa ttcaccgcag tgcatcagaa ccctccttga atcgggctgg tttccaaaca     2220
gaggatttta gtctatatgc ttgtgcttct ccaaaaacac ccatccaggc agggggatat     2280
ggtgcgtttc ctgtccactg a                                                2301
```

<210> SEQ ID NO 3
<211> LENGTH: 766
<212> TYPE: PRT
<213> ORGANISM: Homo sapiens

<400> SEQUENCE: 3

Met Ala Ala Leu Ser Gly Gly Gly Gly Gly Ala Glu Pro Gly Gln
1               5                   10                  15

Ala Leu Phe Asn Gly Asp Met Glu Pro Glu Ala Gly Ala Gly Ala Gly
            20                  25                  30

Ala Ala Ala Ser Ser Ala Ala Asp Pro Ala Ile Pro Glu Glu Val Trp

```
                35                  40                  45
Asn Ile Lys Gln Met Ile Lys Leu Thr Gln Glu His Ile Glu Ala Leu
 50                  55                  60

Leu Asp Lys Phe Gly Gly Glu His Asn Pro Pro Ser Ile Tyr Leu Glu
 65                  70                  75                  80

Ala Tyr Glu Glu Tyr Thr Ser Lys Leu Asp Ala Leu Gln Gln Arg Glu
                 85                  90                  95

Gln Gln Leu Leu Glu Ser Leu Gly Asn Gly Thr Asp Phe Ser Val Ser
                100                 105                 110

Ser Ser Ala Ser Met Asp Thr Val Thr Ser Ser Ser Ser Ser Ser Leu
            115                 120                 125

Ser Val Leu Pro Ser Ser Leu Ser Val Phe Gln Asn Pro Thr Asp Val
            130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
            195                 200                 205

Gly Trp Asp Thr Asp Ile Ser Trp Leu Thr Gly Glu Glu Leu His Val
210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
                260                 265                 270

Ser Thr Glu Val Pro Leu Met Cys Val Asn Tyr Asp Gln Leu Asp Leu
            275                 280                 285

Leu Phe Val Ser Lys Phe Phe Glu His His Pro Ile Pro Gln Glu Glu
            290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
                340                 345                 350

His Arg Asn Gln Phe Gly Gln Arg Asp Arg Ser Ser Ser Ala Pro Asn
            355                 360                 365

Val His Ile Asn Thr Ile Glu Pro Val Asn Ile Asp Asp Leu Ile Arg
            370                 375                 380

Asp Gln Gly Phe Arg Gly Asp Gly Gly Ser Thr Thr Gly Leu Ser Ala
385                 390                 395                 400

Thr Pro Pro Ala Ser Leu Pro Gly Ser Leu Thr Asn Val Lys Ala Leu
                405                 410                 415

Gln Lys Ser Pro Gly Pro Gln Arg Glu Arg Lys Ser Ser Ser Ser Ser
            420                 425                 430

Glu Asp Arg Asn Arg Met Lys Thr Leu Gly Arg Arg Asp Ser Ser Asp
            435                 440                 445

Asp Trp Glu Ile Pro Asp Gly Gln Ile Thr Val Gly Gln Arg Ile Gly
450                 455                 460
```

Ser Gly Ser Phe Gly Thr Val Tyr Lys Gly Lys Trp His Gly Asp Val
465                 470                 475                 480

Ala Val Lys Met Leu Asn Val Thr Ala Pro Thr Gln Gln Leu Gln
            485                 490                 495

Ala Phe Lys Asn Glu Val Gly Val Leu Arg Lys Thr Arg His Val Asn
                500                 505                 510

Ile Leu Leu Phe Met Gly Tyr Ser Thr Lys Pro Gln Leu Ala Ile Val
            515                 520                 525

Thr Gln Trp Cys Glu Gly Ser Ser Leu Tyr His His Leu His Ile Ile
        530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
            565                 570                 575

Leu Lys Ser Asn Asn Ile Phe Leu His Glu Asp Leu Thr Val Lys Ile
                580                 585                 590

Gly Asp Phe Gly Leu Ala Thr Val Lys Ser Arg Trp Ser Gly Ser His
            595                 600                 605

Gln Phe Glu Gln Leu Ser Gly Ser Ile Leu Trp Met Ala Pro Glu Val
610                 615                 620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
            645                 650                 655

Ser Asn Ile Asn Asn Arg Asp Gln Ile Ile Phe Met Val Gly Arg Gly
                660                 665                 670

Tyr Leu Ser Pro Asp Leu Ser Lys Val Arg Ser Asn Cys Pro Lys Ala
            675                 680                 685

Met Lys Arg Leu Met Ala Glu Cys Leu Lys Lys Lys Arg Asp Glu Arg
690                 695                 700

Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
            725                 730                 735

Gly Phe Gln Thr Glu Asp Phe Ser Leu Tyr Ala Cys Ala Ser Pro Lys
                740                 745                 750

Thr Pro Ile Gln Ala Gly Gly Tyr Gly Ala Phe Pro Val His
            755                 760                 765

<210> SEQ ID NO 4
<211> LENGTH: 4454
<212> TYPE: DNA
<213> ORGANISM: Homo sapiens

<400> SEQUENCE: 4
gaaacgtccc gtgtgggagg ggcgggtctg ggtgcggcct gccgcatgac tcgtggttcg      60
gaggcccacg tggccggggc ggggactcag gcgcctgggg cgccgactga ttacgtagcg     120
ggcggggccg gaagtgccgc tccttggtgg gggctgttca tggcggttcc ggggtctcca     180
acatttttcc cggctgtggt cctaaatctg tccaaagcag aggcagtgga gcttgaggtt     240
cttgctggtg tgaaatgact gagtacaaac tggtggtggt tggagcaggt ggtgttggga     300
aaagcgcact gacaatccag ctaatccaga accactttgt agatgaatat gatcccacca     360
tagaggattc ttacagaaaa caagtggtta gatggtga aacctgtttg ttggacatac     420

```
tggatacagc tggacaagaa gagtacagtg ccatgagaga ccaatacatg aggacaggcg    480
aaggcttcct ctgtgtattt gccatcaata atagcaagtc atttgcggat attaacctct    540
acagggagca gattaagcga gtaaaagact cggatgatgt acctatggtg ctagtgggaa    600
acaagtgtga tttgccaaca aggacagttg atacaaaaca agcccacgaa ctggccaaga    660
gttacgggat tccattcatt gaaacctcag ccaagaccag acagggtgtt gaagatgctt    720
tttacacact ggtaagagaa atacgccagt accgaatgaa aaaactcaac agcagtgatg    780
atgggactca gggttgtatg ggattgccat gtgtggtgat gtaacaagat acttttaaag    840
ttttgtcaga aaagagccac tttcaagctg cactgacacc ctggtcctga cttccctgga    900
ggagaagtat tcctgttgct gtcttcagtc tcacagagaa gctcctgcta cttccccagc    960
tctcagtagt ttagtacaat aatctctatt tgagaagttc tcagaataac tacctcctca   1020
cttggctgtc tgaccagaga atgcacctct tgttactccc tgttattttt ctgccctggg   1080
ttcttccaca gcacaaacac acctctgcca ccccaggttt ttcatctgaa aagcagttca   1140
tgtctgaaac agagaaccaa accgcaaacg tgaaattcta ttgaaaacag tgtcttgagc   1200
tctaaagtag caactgctgg tgattttttt tttcttttta ctgttgaact tagaactatg   1260
ctaatttttg gagaaatgtc ataaattact gttttgccaa gaatatagtt attattgctg   1320
tttggtttgt ttataatgtt atcggctcta ttctctaaac tggcatctgc tctagattca   1380
taaatacaaa aatgaatact gaattttgag tctatcctag tcttcacaac tttgacgtaa   1440
ttaaatccaa ctttcacagt gaagtgcctt tttcctagaa gtggtttgta gacttccttt   1500
ataatatttc agtggaatag atgtctcaaa aatccttatg catgaaatga atgtctgaga   1560
tacgtctgtg acttatctac cattgaagga aagctatatc tatttgagag cagatgccat   1620
tttgtacatg tatgaaattg gttttccaga ggcctgtttt ggggctttcc caggagaaag   1680
atgaaactga agcacatgaa ataatttcac ttaataattt ttacctaatc tccacttttt   1740
tcataggtta ctacctatac aatgtatgta atttgtttcc cctagcttac tgataaacct   1800
aatattcaat gaacttccat ttgtattcaa atttgtgtca taccagaaag ctctacattt   1860
gcagatgttc aaatattgta aaactttggt gcattgttat ttaatagctg tgatcagtga   1920
ttttcaaacc tcaaatatag tatattaaca aattacattt tcactgtata tcatggtatc   1980
ttaatgatgt atataattgc cttcaatccc cttctcaccc caccctctac agcttccccc   2040
acagcaatag gggcttgatt atttcagttg agtaaagcat ggtgctaatg gaccagggtc   2100
acagtttcaa aacttgaaca atccagttag catcacagag aaagaaattc ttctgcattt   2160
gctcattgca ccagtaactc cagctagtaa ttttgctagg tagctgcagt tagccctgca   2220
aggaaagaag aggtcagtta gcacaaaccc tttaccatga ctggaaaact cagtatcacg   2280
tatttaaaca tttttttttc tttagccat gtagaaactc taaattaagc caatattctc    2340
atttgagaat gaggatgtct cagctgagaa acgttttaaa ttctctttat tcataatgtt   2400
ctttgaaggg tttaaaacaa gatgttgata aatctaagct gatgagtttg ctcaaaacag   2460
gaagttgaaa ttgttgagac aggaatggaa aatataatta attgatacct atgaggattt   2520
ggaggcttgg cattttaatt tgcagataat accctggtaa ttctcatgaa aaatagactt   2580
ggataacttt tgataaaaga ctaattccaa aatggccact tgttcctgt ctttaatatc    2640 taaatactta ctgaggtcct ccatcttcta tattatgaat tttcatttat taagcaaatg   2700
tcatattacc ttgaaattca gaagagaaga aacatatact gtgtccagag tataatgaac   2760
```

-continued

```
ctgcagagtt gtgcttctta ctgctaattc tgggagcttt cacagtactg tcatcatttg    2820
taaatggaaa ttctgctttt ctgtttctgc tccttctgga gcagtgctac tctgtaattt    2880
tcctgaggct tatcacctca gtcatttctt ttttaaatgt ctgtgactgg cagtgattct    2940
ttttcttaaa aatctattaa atttgatgtc aaattaggga gaaagatagt tactcatctt    3000
gggctcttgt gccaatagcc cttgtatgta tgtacttaga gttttccaag tatgttctaa    3060
gcacagaagt ttctaaatgg ggccaaaatt cagacttgag tatgttcttt gaataccttc    3120
agaagttaca attagccggg catggtggcc cgtgcctgta gtcccagcta cttgagaggc    3180
tgaggcagga gaatcacttc aacccaggag gtggaggtta cagtgagcag agatcgtgcc    3240
actgcactcc agcctgggtg acaagagaga cttgtctcca aaaaaaagt tacacctagg     3300 tgtgaatttt ggcacaaagg agtgacaaac ttatagttaa aagctgaata acttcagtgt    3360
ggtataaaac gtggtttta ggctatgttt gtgattgctg aaaagaattc tagtttacct     3420
caaaatcctt ctctttcccc aaattaagtg cctggccagc tgtcataaat tacatattcc    3480
ttttggtttt tttaaaggtt acatgttcaa gagtgaaaat aagatgttct gtctgaaggc    3540
taccatgccg gatctgtaaa tgaacctgtt aaatgctgta tttgctccaa cggcttacta    3600
tagaatgtta cttaatacaa tatcatactt attacaattt ttactatagg agtgtaatag    3660
gtaaaattaa tctctatttt agtgggccca tgtttagtct ttcaccatcc tttaaactgc    3720
tgtgaatttt tttgtcatga cttgaaagca aggatagaga aacactttag agatatgtgg    3780
ggttttttta ccattccaga gcttgtgagc ataatcatat ttgctttata tttatagtca    3840
tgaactccta agttggcagc tacaaccaag aaccaaaaaa tggtgcgttc tgcttcttgt    3900
aattcatctc tgctaataaa ttataagaag caaggaaaat tagggaaaat attttatttg    3960
gatggtttct ataaacaagg gactataatt cttgtacatt ttttttcatc tttgctgttt    4020
ctttgagcag tctaatgtgc cacacaatta tctaaggtat ttgttttcta taagaattgt    4080
tttaaaagta ttcttgttac cagagtagtt gtattatatt tcaaaacgta agatgatttt    4140
taaaagcctg agtactgacc taagatggaa ttgtatgaac tctgctctgg agggagggga    4200
ggatgtccgt ggaagttgta agacttttat ttttttgtgc catcaaatat aggtaaaaat    4260
aattgtgcaa ttctgctgtt taaacaggaa ctattggcct ccttggccct aaatggaagg    4320
gccgatattt taagttgatt attttattgt aaattaatcc aacctagttc tttttaattt    4380
ggttgaatgt ttttctttgt taaatgatgt ttaaaaaata aaaactggaa gttcttggct    4440
tagtcataat tctt                                                     4454
```

<210> SEQ ID NO 5
<211> LENGTH: 570
<212> TYPE: DNA
<213> ORGANISM: Homo sapiens

<400> SEQUENCE: 5

```
atgactgagt acaaactggt ggtggttgga gcaggtggtg ttgggaaaag cgcactgaca     60
atccagctaa tccagaacca ctttgtagat gaatatgatc ccaccataga ggattcttac    120
agaaaacaag tggttataga tggtgaaacc tgtttgttgg acatactgga tacagctgga    180
caagaagagt acagtgccat gagagaccaa tacatgagga caggcgaagg cttcctctgt    240
gtatttgcca tcaataatag caagtcattt gcggatatta acctctacag ggagcagatt    300
aagcgagtaa aagactcgga tgatgtacct atggtgctag tgggaaacaa gtgtgatttg    360
ccaacaagga cagttgatac aaaacaagcc cacgaactgg ccaagagtta cgggattcca    420
```

```
ttcattgaaa cctcagccaa gaccagacag ggtgttgaag atgcttttta cacactggta    480
agagaaatac gccagtaccg aatgaaaaaa ctcaacagca gtgatgatgg gactcagggt    540
tgtatgggat tgccatgtgt ggtgatgtaa                                    570

<210> SEQ ID NO 6
<211> LENGTH: 189
<212> TYPE: PRT
<213> ORGANISM: Homo sapiens

<400> SEQUENCE: 6

Met Thr Glu Tyr Lys Leu Val Val Gly Ala Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
                100                 105                 110

Leu Val Gly Asn Lys Cys Asp Leu Pro Thr Arg Thr Val Asp Thr Lys
            115                 120                 125

Gln Ala His Glu Leu Ala Lys Ser Tyr Gly Ile Pro Phe Ile Glu Thr
        130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Val Met
            180                 185
```

PHARMACEUTICAL FORMULATIONS OF A PAN-RAF KINASE INHIBITOR AND PROCESSES FOR THEIR PREPARATION

RELATED APPLICATIONS

The present application claims priority from U.S. provisional patent application No. 61/970,595, filed on Mar. 26, 2014, and U.S. provisional patent application No. 62/048,527, filed on Sep. 10, 2014, both of which are hereby incorporated by reference.

The present application claims foreign priority from Uruguay patent application no. 36.046, filed on Mar. 25, 2015, and Pakistan patent application no. 162/2015, filed on Mar. 25, 2015.

SEQUENCE LISTING

This application contains a Sequence Listing which is submitted herewith in electronically readable format. The electronic Sequence Listing file was created on Mar. 19, 2015, is named "sequencelisting.txt" and has a size of 21 kb. The entire contents of the Sequence Listing in the electronic sequeneelisting.txt file are incorporated herein by this reference.

The present invention relates to pharmaceutical compositions comprising the pan-Raf kinase inhibitor (R)-2-(1-(6-amino-5-chloropyrimidine-4-carboxamido)ethyl)-N-(5-chloro-4-(trifluoromethyl)pyridin-2-yl)thiazole-5-carboxamide (Compound 1) or a pharmaceutically acceptable salt thereof and processes for their preparation. The present invention also relates to methods of treating cancer, comprising administering such compositions to a patient according to an intermittent dosing regimen, and to the use of such compositions in the manufacture of medicaments.

Compound 1 has the chemical structure (A):

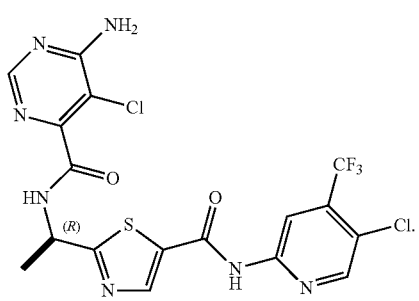

(A)

Compound 1 is a potent, small molecule class II pan-Raf kinase inhibitor being developed for the treatment of solid tumors, including locally advanced, metastatic, and/or unresectable melanoma and BRAF and NRAS mutation-positive cancers. The RAF kinases (A-RAF, BRAF, and C-RAF) are key components of the mitogen-activated protein kinase (MAPK) pathway that controls cell proliferation and survival signaling. (Downward J. Nature Reviews. Cancer 2003; 3(1):11-22; Wellbrock C, et al. Nature Reviews Molecular Cell Biology 2004; 5(10:875-85). The MAP kinase (MAPK) pathway is a central signal transduction pathway that is dysregulated in a large number of developmental disorders. The MAPK pathway, which is composed of RAS, RAF, MAPK or extracellular signal-regulated kinase kinase (MEK), and extracellular signal-regulated kinase (ERK), integrates signals from receptors on the cell surface including cancer-related receptor tyrosine kinases such as the epidermal growth factor receptor, mesenchymal-epithelial transition factor (MET), and vascular endothelial growth factor receptor (Avruch J., Biochim Biophys Acta 2007; 1773(8):1150-60). Genetic alterations in the MAPK pathway are among the most common in human cancers. Up to 60% of melanomas harbor BRAF mutations (Davies H., et al. Nature 2002; 417(6892):949-54) and KRAS mutations have been estimated in roughly 60%, 30%, and 15% of pancreatic, colon, and lung tumors, respectively (Vakiani E, et al. J Pathol 2011; 223(2):219-29). BRAF mutations are also found in 40% of papillary or anaplastic thyroid cancers (Kimura E T, et al. Cancer Res 2003; 63(7):1454-7) and in a small percentage of several other types of tumor (Vakiani E, et al.). A majority of reported BRAF mutations are a substitution of glutamic acid for valine at the amino acid position of 600 (the V600E mutation). The BRAF V600E mutation constitutively activates BRAF and downstream signal transduction in the MAPK pathway (Davies H., et al.).

Compound 1 is an inhibitor of wild-type and mutant Raf kinases and is currently in Phase I clinical trials in patients with relapsed or refractory solid tumors followed by a dose expansion in patients with BRAF and NRAS mutation-positive cancers. Compound 1, its preparation and its use in the treatment of Raf-mediated diseases is disclosed in WO 2009/006389, filed Jun. 30, 2008. Additionally, WO 2013/144923 discloses methods for the treatment of non-BRAFV600E mutant melanoma in patients comprising administering a Raf inhibitor and a MEK inhibitor. The above-mentioned patent applications are herein incorporated by reference.

The advancement of Compound 1 has been somewhat hampered by its physical characteristics, specifically its bioavailability. For example, Compound 1 has low aqueous solubility and a moderate log p. Both can adversely affect is oral bioavailability. Any improvement in the physical characteristics of Compound 1, would potentially offer a more beneficial therapy. Accordingly, it is an object of the present invention to provide a pharmaceutical composition comprising Compound 1 that is stable and which allows for rapid dissolution and enhanced oral bioavailability. Furthermore, it is believed that the efficacy of Compound 1 correlates with drug exposure. Accordingly, it is desirable to be able to administer Compound 1 at the highest possible dose i.e., the highest possible dose at which the side-effect profile is acceptable. A dosing regimen that achieves a higher exposure thereby would provide a meaningful benefit in the treatment of patients with Compound 1. For examples, the dosing regimen of the present invention provides effective treatment of cancer, NRAS and BRAF positive-mutated cancer.

SUMMARY OF THE INVENTION

The present invention provides pharmaceutical compositions as described herein with superior properties, including rapid dissolution and increased oral bioavailability. The present invention also provides processes for the preparation of said pharmaceutical compositions. Furthermore, the present invention provides an intermittent dosing regimen for the improved treatment of cancer. Accordingly, the present invention relates to the following:

1) A pharmaceutical composition comprising (1) a solid dispersion extrudate comprising Compound 1 and (2) one or more pharmaceutically acceptable excipients.

2) A process for preparing a pharmaceutical composition, which comprises the steps of:
   (i) extruding a mixture of Compound 1 or a pharmaceutically acceptable salt thereof and vinylpyrrolidinone-vinyl acetate copolymer to form a solid dispersion extrudate;
   (ii) blending the resulting solid dispersion extrudate with one or more pharmaceutically acceptable excipients.
3) A method for the treatment of NRAS or BRAF positive-mutated cancer in a patient in need of such treatment, comprising administering an effective amount of a pharmaceutical composition comprising Compound 1 or a pharmaceutically acceptable salt thereof and one or more pharmaceutically acceptable excipients, to the patient according to an intermittent dosing regimen, wherein the dosing regimen comprises administering the composition once or twice a week and the total amount of the composition administered each week is from about 400 mg to about 1000 mg.

DETAILED DESCRIPTION OF THE INVENTION

Figure 3:
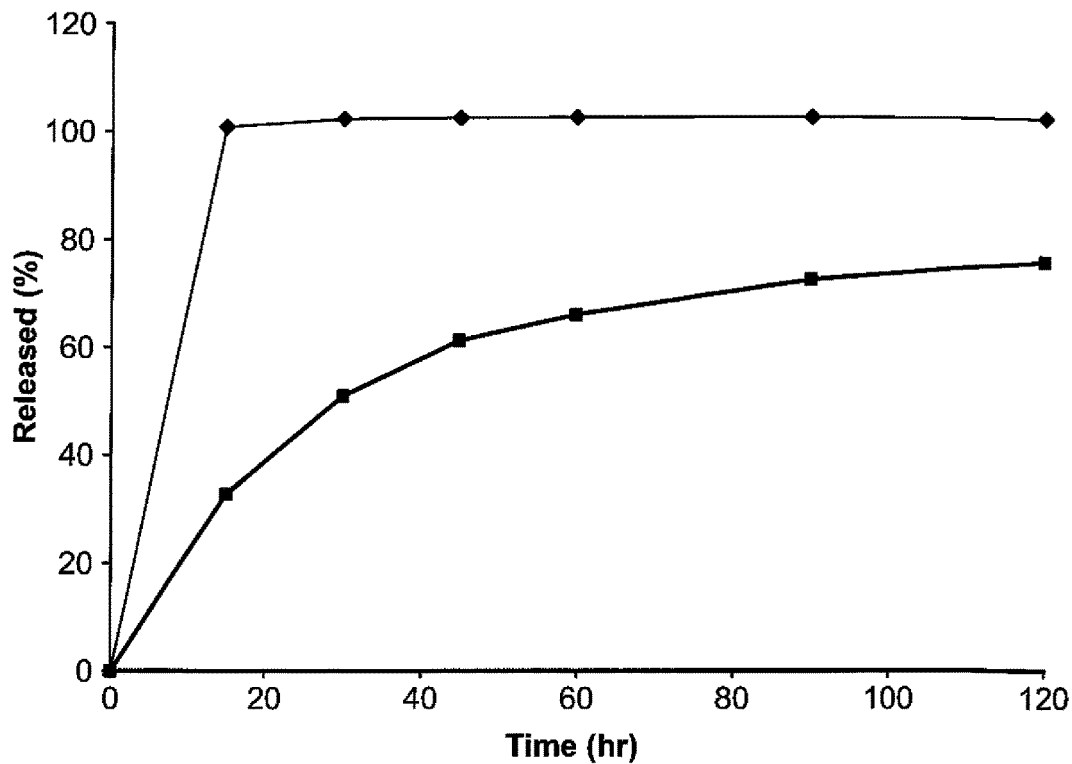

FIG. 3 is a dissolution profile for compositions of the invention used in preclinical bioavailability studies (Example 6). Diamond=tablet; Square=capsule.

Figure 4:
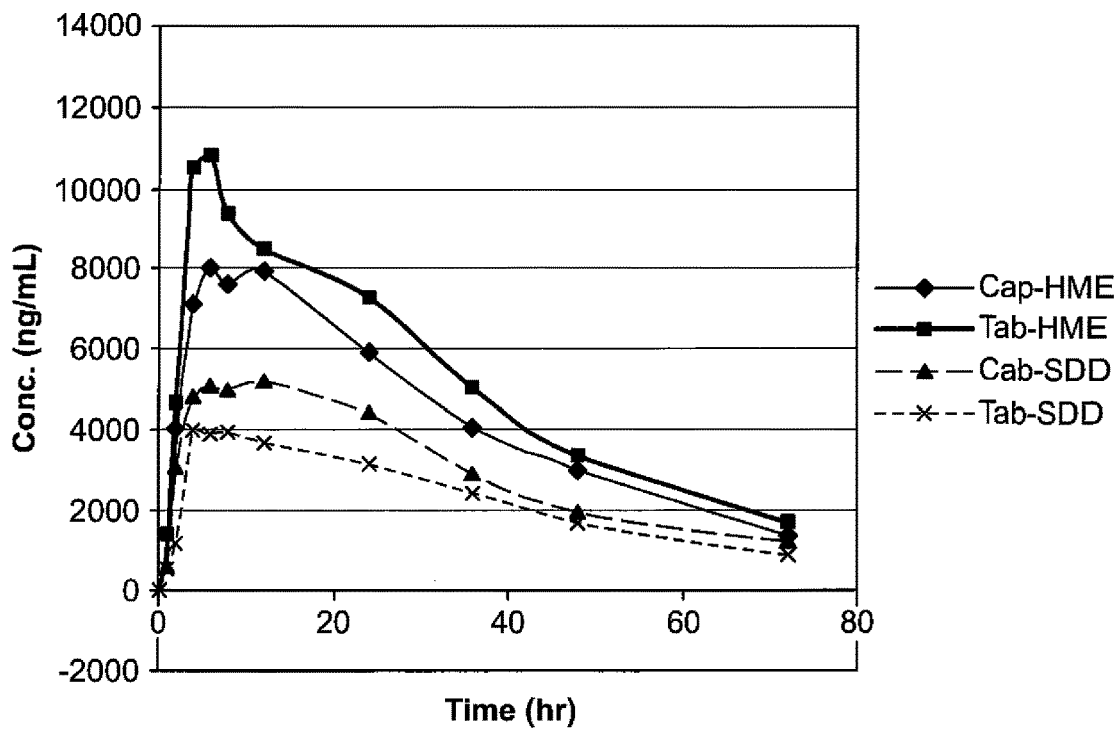

FIG. 4 is a graph which shows the mean plasma profiles over time for formulations of Compound 1 prepared by hot melt extrusion (HME) and spray drying (SDD) in tablet (Tab) and capsule (Cap) form (Example 6).

Figure 5:
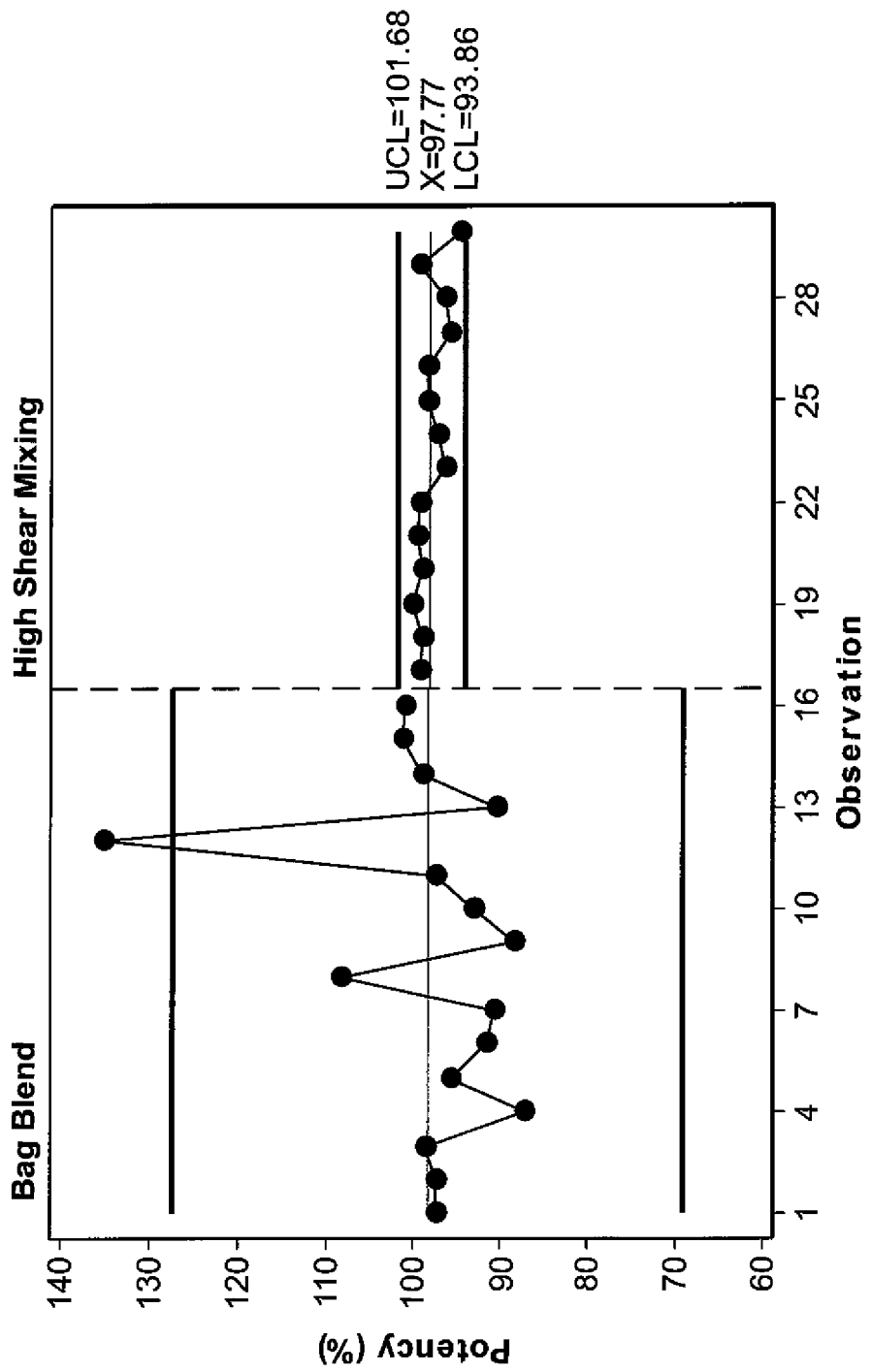

FIG. 5 is a graph which shows the potency difference as a function of the premixing process (bag blend vs. high shear mixing) (Example 7).

Figure 6:
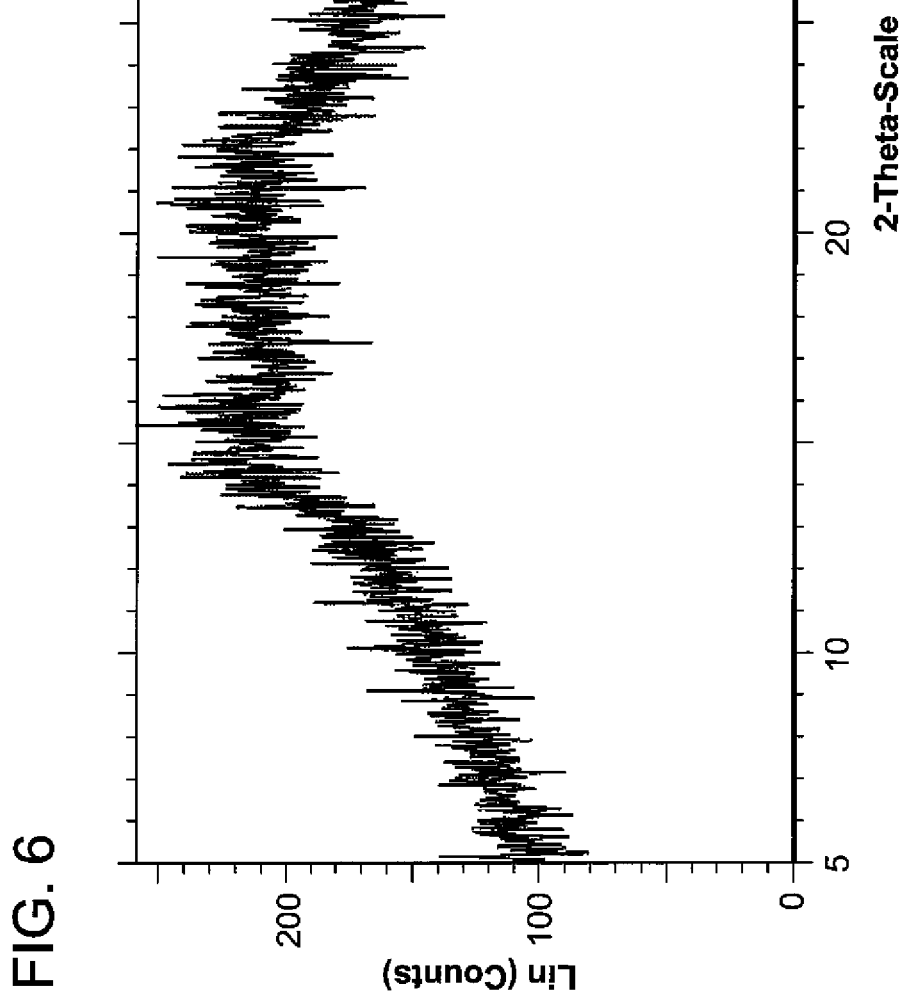

FIG. 6 is an XRPD spectrum of a solid dispersion extrudate of Compound 1 and copovidone produced according to Example 1, procedure 2.

Figure 7A:
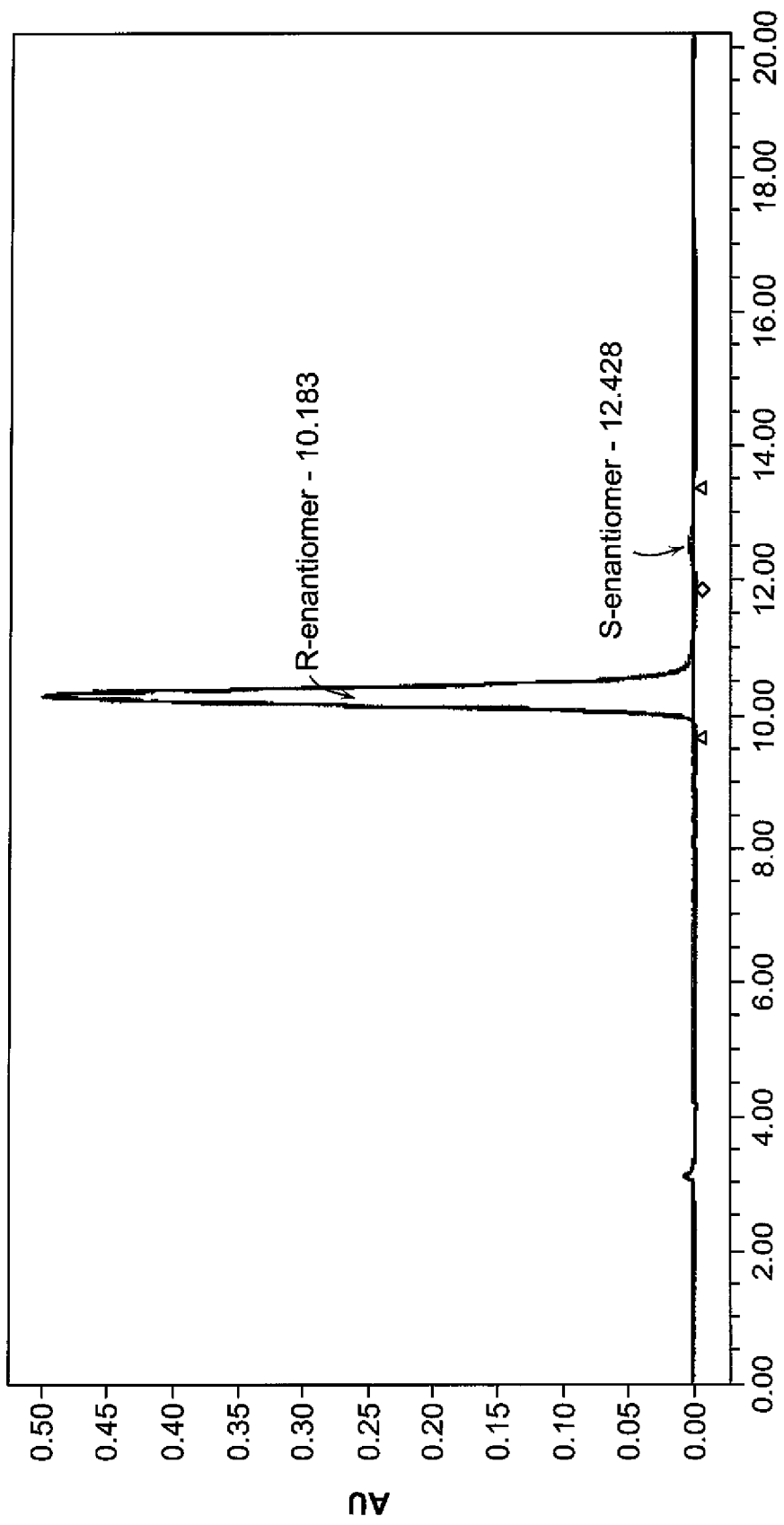

FIG. 7A is an HPLC trace of a solid dispersion extrudate of Compound 1 and copovidone produced according to Example 1, procedure 2.

Figure 7B:
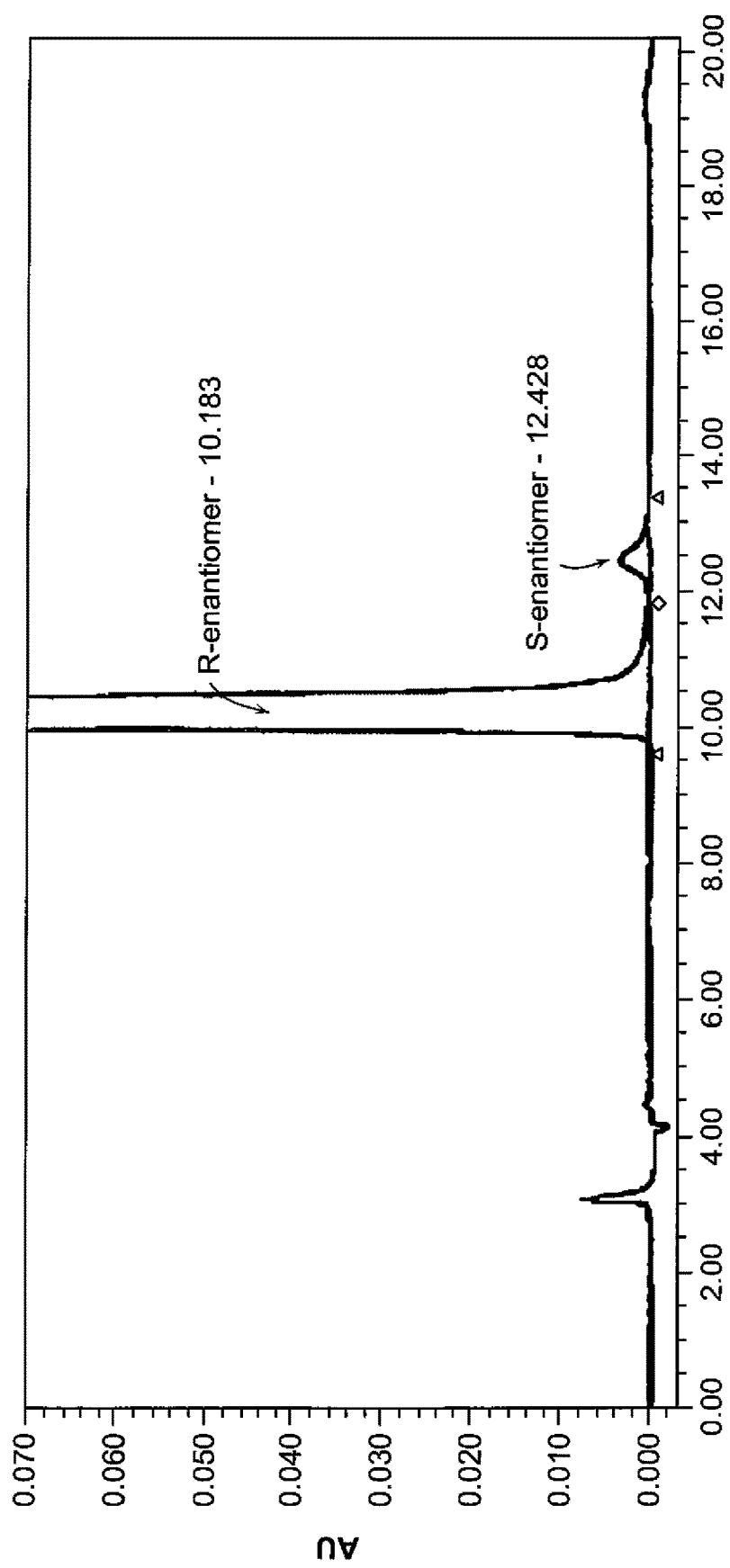

FIG. 7B is an HPLC trace of Compound 1 solid dispersion extrudate produced according to Example 1, procedure 2.

Figure 8:
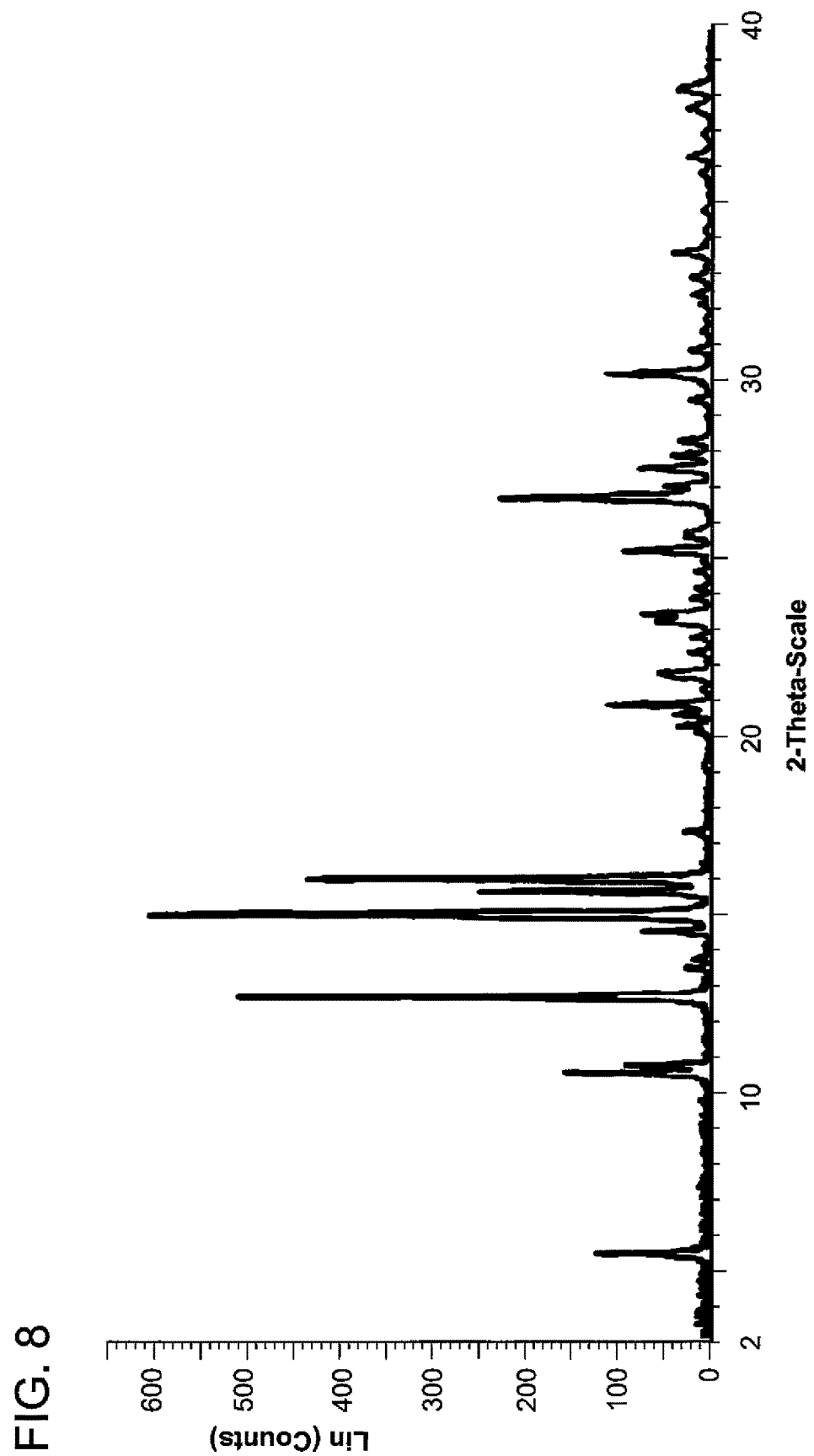

FIG. 8 is a representative XRPD pattern of crystalline Compound 1.

The present invention provides a process for the preparation of a pharmaceutical composition with improved absorption. Compound 1 exhibits a low solubility (<1 mg/ml) and a moderate log p (3.63), thus the bioavailability of Compound 1 is limited by its solubility. We have found that the dissolution property of Compound 1 can be improved by making amorphous solid dispersions prepared by hot melt extrusion. According to the process of the present invention, it is possible to provide, from Compound 1, a formulation wherein the dissolution rate and oral bioavailability of the drug are high. Furthermore, the solid dispersion extrudate of the present invention has superior stability at room temperature.

The pharmaceutical composition of the present invention has superior effects as a medicament in NRAS and/or BRAF positive-mutated cancers. The pharmaceutical composition of the present invention can be administered orally and safely to a patient.

The present invention provides a method for the treatment of cancer in a patient, wherein the cancer has an NRAS or BRAF positive-mutation, by intermittent administration of a pharmaceutical composition as described here, wherein the intermittent dosing regimen is a weekly administration and the amount administered each week is from about 400 mg to about 1000 mg. The intermittent dosing regimen provides a higher unit dose, which allows for the achievement of higher concentrations of Compound 1 and a higher degree of pathway inhibition for a window of time within the dosing interval, without compromising overall dose density.

It is believed, without being bound by theory, that the strong clinical benefits afforded by the pharmaceutical compositions disclosed herein result from improved bioavailability and higher exposures of Compound 1.

Definitions

As used herein, the term "Compound 1" means the compound (R)-2-(1-(6-amino-5-chloropyrimidine-4-carboxamido)ethyl)-N-(5-chloro-4-(trifluoromethyl)pyridin-2-yl)thiazole-5-carboxamide. Additional chemical names for Compound 1 are 6-amino-5-chloro-N-[(1R)-1-[5-[[[5-chloro-4-(trifluoromethyl)-2-pyridinyl]amino]carbonyl]-2-thiazolyl]ethyl]-4-pyrimidinecarboxamide and 6-amino-5-chloro-N-[(1R)-1-(5-{[5-chloro-4-(trifluoromethyl)pyridin-2-yl]carbamoyl}-1,3-thiazol-2-yl)ethyl]pyrimidine-4-carboxamide. The chemical structure of Compound 1 is:

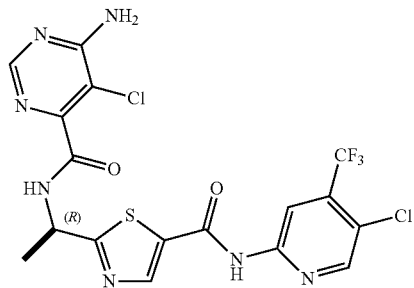

As used herein, "effective amount" means an amount of a therapeutic substance (e.g., a composition of the invention) that is (1) sufficient upon appropriate administration to a patient (a) to cause a detectable decrease in the severity of the disorder or disease state being treated; (b) to ameliorate or alleviate the patient's symptoms of the disease or disorder; or (c) to slow or prevent advancement of, or otherwise stabilize or prolong stabilization of, the disorder or disease state being treated (e.g., prevent additional tumor growth of a cancer); and (2) equal to or less than the maximum tolerated dose (MTD). In any form or composition, the clinically effective amount can be expressed as amount of therapeutic substance per patient BSA, e.g., as mg/m$^2$.

As used herein, "patient" means a human being diagnosed with, exhibiting symptoms of or otherwise believed to be afflicted with a disease, disorder or condition.

As used herein, the illustrative terms "include", "such as", "for example" and the like (and variations thereof, e.g., "includes" and "including", "examples"), unless otherwise specified, are intended to be non-limiting. That is, unless explicitly stated otherwise, such terms are intended to imply "but not limited to", e.g., "including" means including but not limited to.

The terms "about" and "approximately" as used herein, are interchangeable, and should generally be understood to refer to a range of numbers around a given number, as well as to all numbers in a recited range of numbers (e.g., "about 5 to 15" means "about 5 to about 15" unless otherwise stated). Moreover, all numerical ranges herein should be understood to include each whole integer within the range.

"Crospovidone" is a cross-linked homopolymer of vinyl pyrrolidone (VP). One brand of crospovidone is Polyplasdone® XL-10.

The term "vinylpyrrolidione-vinyl acetate copolymer" means a polymer comprising vinylpyrrolidone and vinyl acetate. Names and abbreviations for vinylpyrrolidione-vinyl acetate copolymer include, but are not limited to, copovidone, copovidonum, copolyvidone, copovidon, PVP-VAc-Copolymer. Copovidone is a vinylpyrrolidinone-vinyl acetate copolymer comprised of 6 parts of vinylpyrrolidone and 4 parts of vinyl acetate e.g., CAS 25086-89-9. Examples of copovidone commercial products are Kollidon® VA 64 and Kollidon® 64 Fine. Another example is "Plasdone S-630," a 60:40 random copolymer of N-vinyl pyrrolidinone and vinyl acetate.

"Eudragit®" is an anionic copolymer based on methacrylic acic and methyl methacrylate.

"HPMCAS" refers to hypromellose acetate succinate, a polymer containing acetyl and succinoyl groups. There are different types of HPMCAS, which dissolve at different pHs.

"Poloxamer" is a nonionic triblock copolymer composed of a central hydrophobic chain of polyoxypropylene (poly (propylene oxide)) flanked by two hydrophilic chains of polyoxyethylene.

"w/w" means by weight. For example, 40% w/w means that the mass of the substance is 40% of the total mass of the solution or mixture. For example, 40% extrudate w/w is 3400 g (1360 g Compound 1+2040 g copovidone) of a composition having a total mass of 8500 g.

As used herein, the term "substantially amorphous" refers to a solid material having little or no long range order in the position of its molecules. For example, a substantially amorphous material has less than about 30% crystallinity (e.g., less than about 25% crystallinity, less than about 20% crystallinity, less than about 15% crystallinity, less than about 10% crystallinity, less than about 5% crystallinity, less than about 4% crystallinity). It is also noted that the term 'substantially amorphous' includes the descriptor, 'amorphous', which refers to a material having no (0%) crystallinity.

As used herein, the term "crystalline" and related terms used herein, when used to describe a substance, component or product is substantially crystalline as determined by X-ray diffraction and/or FT-Raman microscopy.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt of Compound 1 that, upon administration to a recipient, is capable of providing, either directly or indirectly, Compound 1 or an active metabolite or residue thereof.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of Compound 1 include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of Compound 1. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Pharmaceutical Compositions

The present invention relates to pharmaceutical compositions comprising the pan-Raf kinase inhibitor Compound 1 or a pharmaceutically acceptable salt thereof. The present invention includes the following embodiments:

Embodiment [1]

A pharmaceutical composition comprising (1) a solid dispersion extrudate comprising Compound 1 or a pharmaceutically acceptable salt thereof and a vinylpyrrolidinone-vinyl acetate copolymer and (2) one or more pharmaceutically acceptable excipients.

Embodiment [2]

A pharmaceutical composition comprising (1) from about 10% to about 50% w/w of a solid dispersion extrudate comprising Compound 1 or a pharmaceutically acceptable salt thereof and a vinylpyrrolidinone-vinyl acetate copolymer and (2) from about 50% to about 90% w/w of one or more pharmaceutically acceptable excipients comprising a filler, disintegrant, glidant and lubricant.

Embodiment [3]

A pharmaceutical compositions comprising (1) from about 10% to about 50% w/w of a solid dispersion extrudate comprising Compound 1 or a pharmaceutically acceptable salt thereof and a vinylpyrrolidinone-vinyl acetate copolymer and (2) from about 50% to about 90% w/w of one or more pharmaceutically acceptable excipients comprising a filler, disintegrant, glidant, lubricant, film-coating agent, colorant, and plasticizer.

Embodiment [4]

A pharmaceutical composition comprising (1) from about 20% to about 40% w/w of a solid dispersion extrudate comprising Compound 1 or a pharmaceutically acceptable salt thereof and a vinylpyrrolidinone-vinyl acetate copolymer and (2) from about 60% to about 80% w/w of one or more pharmaceutically acceptable excipients comprising a filler, disintegrant, glidant and lubricant.

Embodiment [5]

A pharmaceutical composition comprising (1) from about 20% to about 40% w/w of a solid dispersion extrudate comprising Compound 1 or a pharmaceutically acceptable salt thereof and a vinylpyrrolidinone-vinyl acetate copolymer and (2) from about 60% to about 80% w/w of one or more pharmaceutically acceptable excipients comprising a filler, disintegrant, glidant, lubricant, film-coating agent, colorant, and plasticizer.

Embodiment [6]

A pharmaceutical composition comprising (1) from about 40% to about 50% w/w of a solid dispersion extrudate comprising Compound 1 or a pharmaceutically acceptable salt thereof and a vinylpyrrolidinone-vinyl acetate copolymer and (2) from about 60% to about 50% w/w of one or more pharmaceutically acceptable excipients comprising a filler, disintegrant, glidant and lubricant.

Embodiment [7]

A pharmaceutical composition comprising (1) from about 40% to about 50% w/w of a solid dispersion extrudate comprising Compound 1 or a pharmaceutically acceptable salt thereof and a vinylpyrrolidinone-vinyl acetate copolymer and (2) from about 60% to about 50% w/w of one or more pharmaceutically acceptable excipients comprising a filler, disintegrant, glidant, lubricant, film-coating agent, colorant, and plasticizer.

Embodiment [8]

A pharmaceutical composition in the form of a 5 mg tablet or capsule comprising about 10% w/w of a solid dispersion extrudate comprising Compound 1 or a pharmaceutically acceptable salt thereof and a vinylpyrrolidinone-vinyl acetate copolymer and (2) about 90% w/w of one or more pharmaceutically acceptable excipients. In one aspect, the form is tablet. In one aspect, the form is capsule.

Embodiment [9]

A pharmaceutical composition in the form of a 20 mg tablet or capsule comprising about 20% w/w of a solid dispersion extrudate comprising Compound 1 or a pharmaceutically acceptable salt thereof and a vinylpyrrolidinone-vinyl acetate copolymer and (2) about 80% w/w of one or more pharmaceutically acceptable excipients. In one aspect, the form is tablet. In one aspect, the form is capsule.

Embodiment [10]

A pharmaceutical composition in the form of a 70 mg tablet or capsule comprising about 32% w/w/of a solid dispersion extrudate comprising Compound 1 or a pharmaceutically acceptable salt thereof and a vinylpyrrolidinone-vinyl acetate copolymer and (2) about 68% of one or more pharmaceutically acceptable excipients. In one aspect, the form is tablet. In one aspect, the form is capsule.

Embodiment [11]

A pharmaceutical composition in the form of a 100 mg tablet or capsule comprising about 40% w/w of a solid dispersion extrudate comprising Compound 1 or a pharmaceutically acceptable salt thereof and a vinylpyrrolidinone-vinyl acetate copolymer and (2) about 60% w/w of one or more pharmaceutically acceptable excipients. In one aspect, the form is tablet. In one aspect, the form is capsule.

The percentage by weight (w/w) of solid dispersion in the pharmaceutical compositions described herein is important for the disintegration rate of the composition. In one aspect, a pharmaceutical composition prepared at about 40% w/w solid dispersion exhibited rapid dissolution, achieving full release in less than 10 minutes.

Embodiment [12]

The pharmaceutical composition of any one of embodiments [1] through [11], wherein the solid dispersion extrudate comprises Compound 1.

Embodiment [13]

The pharmaceutical composition of any one of embodiments [1] through [11], wherein the solid dispersion extrudate comprises the pharmaceutically acceptable salt of Compound 1.

Embodiment [14]

The pharmaceutical composition of any one of embodiments [1] through [13], wherein the vinylpyrrolidinone-vinyl acetate copolymer is copovidone. In one aspect, the copovidone is Kollidon® VA 64. In one aspect, the copovidone is Kollidon® VA 64 Fine.

Embodiment [15]

The pharmaceutical composition of any one of embodiments [1] through [14], wherein the solid dispersion extrudate is amorphous.

The amorphous character of the solid dispersion extrudate can be detected using analytical methods, including but not limited to, microscopic methods (scanning electronic microscopy (SEM), polarized light microscopy (PLM), hot stage microscopy (HSM)), thermal methods (differential scanning calorimetry (DSC) modulated DSC (mDSC), diffraction methods such as X-ray powder diffraction (XRPD), and spectroscopic methods (FT-Infrared (IR), FT-Ramen, solid state NMR (ssNMR) and confocal raman microscopy (CRM)). In one aspect, the amorphous character of the solid dispersion extrudate is detected by X-ray powder diffraction (XRPD). In one aspect, the solid dispersion extrudate exhibits no residual crystalline character. FIG. 6 is an XRPD spectrum of a solid dispersion extrudate produced according to Example 1, procedure 1. The XRPD spectrum shows the amorphous character of the solid dispersion extract.

Embodiment [16]

The pharmaceutical composition of any one of embodiments [1] through [15], wherein the glass transition temperature (TG) of the solid dispersion extrudate is from about 45° C. to about 120° C.

Embodiment [17]

The pharmaceutical composition of any one of embodiments [1] through [16], wherein the glass transition temperature (TG) of the solid dispersion extrudate is from about 60° C. to about 110° C.

Embodiment [18]

The pharmaceutical composition of any one of embodiments [1] through [17], wherein the solid dispersion extrudate comprises <about 3% w/w of the S-enantiomer of 2-(1-(6-amino-5-chloropyrimidine-4-carboxamido)ethyl)-N-(5-chloro-4-(trifluoromethyl)pyridin-2-yl)thiazole-5-carboxamide.

In one aspect, the total amount of impurities, including the S-enantiomer of 2-(1-(6-amino-5-chloropyrimidine-4-carboxamido)ethyl)-N-(5-chloro-4-(trifluoromethyl)pyridin-2-yl)thiazole-5-carboxamide of the solid dispersion extrudate is less than or equal to about 3.0% w/w or more than or equal to about 97.0% w/w of the desired R-enantiomer, Compound 1. In one aspect, the total amount of the S-enantiomer is ≤about 3%, ≤about 2.7%, ≤about 2.5%, ≤about 2.3%, ≤about 2.1%, ≤about 1.9%, ≤about 1.7%, ≤about 1.5%, ≤about 1.3%, ≤about 1.1%, ≤about 0.9%, ≤about 0.8%, ≤about 0.7%, ≤about 0.5%, ≤about 0.3%, ≤about 0.1%. FIGS. 7A and 7B are HPLC traces of a solid dispersion extrudate produced according to the method described in Example 1, procedure 2. Optimization of the conditions of the extrusion process reduces formation of the S-enantiomer.

Embodiment [19]

The pharmaceutical composition of any one of embodiments [1] through [18], wherein the amount of Compound 1 is from about 3% to about 17% w/w.

Embodiment [20]

The pharmaceutical composition of any one of embodiments [1] through [19], wherein the amount of is from about 7% to about 17% w/w.

Embodiment [21]

The pharmaceutical composition of any one of embodiments [1] through [20], wherein the amount of Compound 1 is from about 8% to about 16% w/w.

Embodiment [22]

The pharmaceutical composition of any one of embodiments [1] through [8] or [12] through [19], wherein the composition is in the form of a 5 mg tablet or capsule, wherein the amount of Compound 1 is about 4% w/w. In one aspect, the form is tablet. In one aspect, the form is capsule.

Embodiment [23]

The pharmaceutical composition of any one of embodiments [1] through [7], [9], or [12] through [21], wherein the composition is in the form of a 20 mg tablet or capsule, wherein the amount of Compound 1 is about 8% w/w. In one aspect, the form is tablet. In one aspect, the form is capsule.

Embodiment [24]

The pharmaceutical composition of any one of embodiments [1] through [7], [10], or [12] through [21], wherein the composition is in the form of a 70 mg tablet or capsule, wherein the amount of Compound 1 is about 13% w/w. In one aspect, the form is tablet. In one aspect, the form is capsule.

Embodiment [25]

The pharmaceutical composition of any one of embodiments [1] through [7] or [11] through [21], wherein the composition is in the form of a 100 mg tablet or capsule, wherein the amount of Compound 1 is about 16% w/w. In one aspect, the form is tablet. In one aspect, the form is capsule.

Embodiment [26]

The pharmaceutical composition of any one of embodiments [1] through [25], wherein the amount of vinylpyrrolidinone-vinyl acetate copolymer is from about 5% to about 25% w/w. In one aspect, the copolymer is copovidone. In one aspect, the amount of copovidone is from about 5% to about 25% w/w.

Embodiment [27]

The pharmaceutical composition of any one of embodiments [1] through [26], wherein the amount of vinylpyrrolidinone-vinyl acetate copolymer is from about 12% to about 24% w/w. In one aspect, the copolymer is copovidone. In one aspect, the amount of copovidone is from about 12% to about 24% w/w.

Embodiment [28]

The pharmaceutical composition of any one of embodiments [1] through [27], wherein the amount of vinylpyrrolidinone-vinyl acetate copolymer is from about 11% to about 24% w/w. In one aspect, the copolymer is copovidone. In one aspect, the amount of copovidone is from about 11% to about 24% w/w.

Embodiment [29]

The pharmaceutical composition of any one of embodiments [1] through [8], [12] through [19], [22], or [26], wherein the composition is in the form of a 5 mg tablet or capsule, wherein the amount of vinylpyrrolidinone-vinyl acetate copolymer is about 6% w/w. In one aspect, the copolymer is copovidone. In one aspect, the amount of copovidone is about 6% w/w. In one aspect, the form is tablet. In one aspect, the form is capsule.

Embodiment [30]

The pharmaceutical composition of any one of embodiments [1] through [7], [9], [12] through [21], [23], or [26] through [28], wherein the composition is in the form of a 20 mg tablet or capsule, wherein the amount of vinylpyrrolidinone-vinyl acetate copolymer about 12% w/w. In one aspect, the copolymer is copovidone. In one aspect, the amount of copovidone is about 12% w/w. In one aspect, the form is tablet. In one aspect, the form is capsule.

Embodiment [31]

The pharmaceutical composition of any one of embodiments [1] through [7], [10], [12] through [21], [24], or [26] through [28], wherein the composition is in the form of a 70 mg tablet or capsule, wherein the amount of vinylpyrrolidinone-vinyl acetate copolymer about 19% w/w. In one aspect, the copolymer is copovidone. In one aspect, the amount of copovidone is about 19% w/w. In one aspect, the form is tablet. In one aspect, the form is capsule.

Embodiment [32]

The pharmaceutical composition of any one of embodiments [1] through [7], [11] through [21], or [25] through [28], wherein the composition is in the form of a 100 mg tablet or capsule, wherein the amount of vinylpyrrolidinone-vinyl acetate copolymer is about 24% w/w. In one aspect, the copolymer is copovidone. In one aspect, the amount of copovidone is about 24% w/w. In one aspect, the form is tablet. In one aspect, the form is capsule.

Embodiment [33]

The pharmaceutical composition of any one of embodiments [1] through [32], wherein one or more pharmaceutically acceptable excipients comprises a disintegrant, wherein the disintegrant comprises croscarmellose sodium. Croscarmellose sodium serves as a disintegrant for immediate release. Disintegration is a function of the type of superdisintegrant and solid dispersion loading within the formulation.

Embodiment [34]

The pharmaceutical composition of any one of embodiments [1] through [33], wherein one or more pharmaceutically acceptable excipients comprises a disintegrant, wherein the disintegrant comprises croscarmellose sodium and wherein the amount of croscarmellose sodium is from about 4% to about 9% w/w.

Embodiment [35]

The pharmaceutical composition of any one of embodiments [1] through [34], wherein one or more pharmaceutically acceptable excipients comprises a disintegrant, wherein the disintegrant comprises croscarmellose sodium and wherein the amount of croscarmellose sodium is from about 5% to about 8% w/w.

Embodiment [36]

The pharmaceutical composition of any one of embodiments [1] through [9], [12] through [23], [26] through [30], or [33] through [35], wherein the composition is in the form of a 5 mg or 20 mg tablet or capsule, wherein one or more pharmaceutically acceptable excipients comprises a disintegrant, wherein the disintegrant comprises croscarmellose sodium and wherein the amount of croscarmellose sodium is about 5% w/w. In one aspect, the form is tablet. In one aspect, the form is capsule.

Embodiment [37]

The pharmaceutical composition of any one of embodiments [1] through [8], [12] through [19], [22], [26] through [29], or [33] through [35], wherein the composition is in the form of a 5 mg tablet or capsule, wherein one or more pharmaceutically acceptable excipients comprises a disintegrant, wherein the disintegrant comprises croscarmellose sodium and wherein the amount of croscarmellose sodium is about 5% w/w. In one aspect, the form is tablet. In one aspect, the form is capsule.

Embodiment 1381

The pharmaceutical composition of any one of embodiments [1] through [7], [9], [12] through [21], [23], [26] through [28], [30], or [33] through [36], wherein the composition is in the form of a 20 mg tablet or capsule, wherein one or more pharmaceutically acceptable excipients comprises a disintegrant, wherein the disintegrant comprises croscarmellose sodium and wherein the amount of croscarmellose sodium is about 5% w/w. In one aspect, the form is tablet. In one aspect, the form is capsule.

Embodiment [39]

The pharmaceutical composition of any one of embodiments [1] through [7], [10] through [21], [24] through [28], or [31] through [35], wherein the composition is in the form of a 70 or 100 mg tablet or capsule, wherein one or more pharmaceutically acceptable excipients comprises a disintegrant, wherein the disintegrant is croscarmellose sodium and wherein the amount of croscarmellose sodium is about 8% w/w. In one aspect, the form is tablet. In one aspect, the form is capsule.

Embodiment [40]

The pharmaceutical composition of any one of embodiments [1] through [7], [11] through [21], [25] through [28], [32] through [35], or [39], wherein the composition is in the form of a 100 mg tablet or capsule, wherein one or more pharmaceutically acceptable excipients comprises a disintegrant, wherein the disintegrant is croscarmellose sodium and wherein the amount of croscarmellose sodium is about 8% w/w. In one aspect, the form is tablet. In one aspect, the form is capsule.

Embodiment [41]

The pharmaceutical composition of any one of embodiments [1] through [7], [10], [12] through [21], [24], [26] through [28], [31], [33] through [35], or [39], wherein the composition is in the form of a 70 mg tablet or capsule, wherein one or more pharmaceutically acceptable excipients comprises a disintegrant, wherein the disintegrant is croscarmellose sodium and wherein the amount of croscarmellose sodium is about 8% w/w. In one aspect, the form is tablet. In one aspect, the form is capsule.

Embodiment [42]

The pharmaceutical composition of any one of embodiments [1] through [41], wherein one or more pharmaceutically acceptable excipients comprises a glidant, wherein the glidant comprises colloidal silicon dioxide. In one aspect, colloidal silicon dioxide aids the flow property of the formulation blend (blended powder).

Embodiment [43]

The pharmaceutical composition of any one of embodiments [1] through [42], wherein one or more pharmaceutically acceptable excipients comprises a glidant, wherein the glidant comprises colloidal silicon dioxide and wherein the amount of colloidal silicon dioxide is about 0.5% to about 6% w/w.

Embodiment [44]

The pharmaceutical composition of any one of embodiments [1] through [43], wherein one or more pharmaceutically acceptable excipients comprises a glidant, wherein the glidant comprises colloidal silicon dioxide and wherein the amount of colloidal silicon dioxide is about 3% to about 6% w/w.

Embodiment [45]

The pharmaceutical composition of any one of embodiments [1] through [44], wherein one or more pharmaceutically acceptable excipients comprises a glidant, wherein the glidant comprises colloidal silicon dioxide and wherein the amount of colloidal silicon dioxide is from about 3.5% to about 4.5% w/w.

Embodiment [46]

The pharmaceutical composition of any one of embodiments [1] through [45], wherein one or more pharmaceutically acceptable excipients comprises a glidant, wherein the glidant comprises colloidal silicon dioxide and wherein the amount of colloidal silicon dioxide is about 4.5% w/w.

Embodiment [47]

The pharmaceutical composition of any one of embodiments [1] through [43], wherein one or more pharmaceutically acceptable excipients comprises a glidant, wherein the glidant comprises colloidal silicon dioxide and wherein the amount of colloidal silicon dioxide is from about 0.5% to about 5% w/w.

Embodiment [48]

The pharmaceutical composition of any one of embodiments [1] through [43] or [47], wherein one or more pharmaceutically acceptable excipients comprises a glidant, wherein the glidant comprises colloidal silicon dioxide and wherein the amount of colloidal silicon dioxide is from about 0.5% to about 2% w/w.

Embodiment [49]

The pharmaceutical composition of any one of embodiments [1] through [43] or [47] through [48], wherein one or more pharmaceutically acceptable excipients comprises a glidant, wherein the glidant comprises colloidal silicon dioxide and wherein the amount of colloidal silicon dioxide is about 0.5% w/w. In one aspect, the amount of colloidal silicon dioxide provides increased stability. In one aspect, the amount of colloidal silicon dioxide provides increased hardness of the tablet.

Embodiment [50]

The pharmaceutical composition of any one of embodiments [1] through [9], [11] through [23], [25] through [30], [32] through [40], or [42] through [47], wherein the composition is in the form of a 5, 20, or 100 mg tablet or capsule, wherein one or more pharmaceutically acceptable excipients comprises a glidant, wherein the glidant comprises colloidal silicon dioxide and wherein the amount of colloidal silicon dioxide is about 4.5% w/w. In one aspect, the form is tablet. In one aspect, the form is capsule.

Embodiment [51]

The pharmaceutical composition of any one of embodiments [1] through [8], [10] through [22], [24] through [29], [31] through [37], or [39] through [49], wherein the composition is in the form of a 5, 70, or 100 mg tablet or capsule, wherein one or more pharmaceutically acceptable excipients comprises a glidant, wherein the glidant comprises colloidal silicon dioxide and wherein the amount of colloidal silicon dioxide is about 0.5% w/w. In one aspect, the form is tablet. In one aspect, the form is capsule.

Embodiment [52]

The pharmaceutical composition of any one of embodiments [1] through [51], wherein one or more pharmaceutically acceptable excipients comprises a filler, wherein the filler comprises microcrystalline cellulose.

Embodiment [53]

The pharmaceutical composition of any one of embodiments [1] through [52], wherein one or more pharmaceutically acceptable excipients comprises a filler, wherein the filler comprises microcrystalline cellulose and wherein the amount of microcrystalline cellulose is from about 40% to about 81% w/w.

Embodiment [54]

The pharmaceutical composition of any one of embodiments [1] through [53], wherein one or more pharmaceutically acceptable excipients comprises a filler, wherein the filler comprises microcrystalline cellulose and wherein the amount of microcrystalline cellulose is from about 46% to about 81% w/w.

Embodiment [55]

The pharmaceutical composition of any one of embodiments [1] through [53], wherein one or more pharmaceutically acceptable excipients comprises a filler, wherein the filler comprises microcrystalline cellulose and wherein the amount of microcrystalline cellulose is from about 40% to about 80% w/w.

Embodiment [56]

The pharmaceutical composition of any one of embodiments [1] through [55], wherein one or more pharmaceutically acceptable excipients comprises a filler, wherein the filler comprises microcrystalline cellulose and wherein the amount of microcrystalline cellulose is from about 51% to about 74% w/w.

Embodiment [57]

The pharmaceutical composition of any one of embodiments [1] through [55], wherein one or more pharmaceutically acceptable excipients comprises a filler, wherein the filler comprises microcrystalline cellulose and wherein the amount of microcrystalline cellulose is from about 47% to about 70% w/w.

Embodiment [58]

The pharmaceutical composition of any one of embodiments [1] through [8], [12] through [19], [22], [26], [29], [33] through [37], [42] through [47], or [50] through [55], wherein the composition is in the form of a 5 mg tablet or capsule, wherein one or more pharmaceutically acceptable excipients comprises a filler, wherein the filler comprises microcrystalline cellulose and wherein the amount of microcrystalline cellulose is about 80% w/w. In one aspect, the form is tablet. In one aspect, the form is capsule.

Embodiment [59]

The pharmaceutical composition of any one of embodiments [1] through [7], [9], [12] through [21], [23], [26] through [28], [30], [33] through [36], [38], [42] through [47], or [50] through [56], wherein the composition is in the form of a 20 mg tablet or capsule, wherein one or more pharmaceutically acceptable excipients comprises a filler, wherein the filler comprises microcrystalline cellulose and wherein the amount of microcrystalline cellulose is from about 70% to about 74% w/w. In one aspect, the form is tablet. In one aspect, the form is capsule.

Embodiment [60]

The pharmaceutical composition of any one of embodiments [1] through [7], [9], [12] through [21], [23], [26] through [28], [30], [33] through [36], [38], [42] through [47], or [50] through [57], wherein the composition is in the form of a 20 mg tablet or capsule, wherein one or more pharmaceutically acceptable excipients comprises a filler, wherein the filler comprises microcrystalline cellulose and wherein the amount of microcrystalline cellulose is about 70% w/w. In one aspect, the form is tablet. In one aspect, the form is capsule.

Embodiment [61]

The pharmaceutical composition of any one of embodiments [1] through [7], [9], [12] through [21], [23], [26] through [28], [30], [33] through [36], [38], [42] through [47], or [50] through [56], wherein the composition is in the form of a 20 mg tablet or capsule, wherein one or more pharmaceutically acceptable excipients comprises a filler, wherein the filler comprises microcrystalline cellulose and wherein the amount of microcrystalline cellulose is about 74% w/w. In one aspect, the form is tablet. In one aspect, the form is capsule.

Embodiment [62]

The pharmaceutical composition of any one of embodiments [1] through [7], [10], [12] through [21], [24], [26] through [28], [31], [33] through [35], [39], [42] through [49], or [51] through [57], wherein the composition is in the form of a 70 mg tablet or capsule, wherein one or more pharmaceutically acceptable excipients comprises a filler, wherein the filler comprises microcrystalline cellulose and wherein the amount of microcrystalline cellulose is about 59% w/w. In one aspect, the form is tablet. In one aspect, the form is capsule.

Embodiment [63]

The pharmaceutical composition of any one of embodiments [1] through [7], [11] through [21], [25] through [28], [32] through [35], [39] through [40], or [42] through [57], wherein the composition is in the form of a 100 mg tablet or capsule, wherein one or more pharmaceutically acceptable excipients comprises a filler, wherein the filler comprises microcrystalline cellulose and wherein the amount of microcrystalline cellulose is from about 47% to about 51% w/w. In one aspect, the form is tablet. In one aspect, the form is capsule.

Embodiment [64]

The pharmaceutical composition of any one of embodiments [1] through [7], [11] through [21], [25] through [28], [32] through [35], [39] through [40], [42] through [49], [52] through [55], or [57], wherein the composition is in the form of a 100 mg tablet or capsule, wherein one or more pharmaceutically acceptable excipients comprises a filler, wherein the filler comprises microcrystalline cellulose and wherein the amount of microcrystalline cellulose is about 47% w/w. In one aspect, the form is tablet. In one aspect, the form is capsule.

Embodiment [65]

The pharmaceutical composition of any one of embodiments [1] through [7], [11] through [21], [25] through [28], [32] through [35], [39] through [40], [42] through [49], or [52] through [57], wherein the composition is in the form of a 100 mg tablet or capsule, wherein one or more pharmaceutically acceptable excipients comprises a filler, wherein the filler comprises microcrystalline cellulose and wherein the amount of microcrystalline cellulose is about 51% w/w. In one aspect, the form is tablet. In one aspect, the form is capsule.

Embodiment [66]

The pharmaceutical composition of any one of embodiments [1] through [65], wherein one or more pharmaceutically acceptable excipients comprises a lubrican$_t$, wherein the lubricant comprises magnesium stearate. In one aspect, magnesium stearate provides lubrication of the formulation during compression.

Embodiment [67]

The pharmaceutical composition of any one of embodiments [1] through [66], wherein one or more pharmaceutically acceptable excipients comprises a lubricant, wherein the lubricant comprises magnesium stearate and wherein the amount of magnesium stearate is from about 0.3% to about 0.7% w/w.

Embodiment [68]

The pharmaceutical composition of any one of embodiment [1] through [67], wherein one or more pharmaceutically acceptable excipients comprises a lubricant, wherein the lubricant comprises magnesium stearate and wherein the amount of magnesium stearate is from about 0.4% to about 0.5% w/w.

Embodiment [69]

The pharmaceutical composition of any one of embodiments [1] through [68], wherein one or more pharmaceutically acceptable excipients comprises a lubricant, wherein the lubricant comprises magnesium stearate and wherein the amount of magnesium stearate is about 0.5% w/w.

Embodiment [70]

The pharmaceutical composition of any one of embodiments [I] through [69], wherein one or more pharmaceutically acceptable excipients comprises a lubricant, wherein the lubricant comprises magnesium stearate and wherein the composition is in the form of a 5, 20, 70, or 100 mg tablet or capsule, wherein the amount of magnesium stearate is about 0.5% w/w. In one aspect, the form is tablet. In one aspect, the form is capsule.

Embodiment [71]

The pharmaceutical composition of any one of embodiments [1] through [9], [11] through [23], [25] through [30], [32] through [40], [42] through [47], or [48] through [70], wherein one or more pharmaceutically acceptable excipients comprises a lubricant, wherein the lubricant comprises magnesium stearate and wherein the composition is in the form of a 5, 20, or 100 mg tablet or capsule, wherein the amount of magnesium stearate is about 0.5% w/w. In one aspect, the form is tablet. In one aspect, the form is capsule.

Embodiment [72]

The pharmaceutical composition of any one of embodiments [1] through [7], [9] through [21], [23] through [28], [30] through [36], [38] through [57], or [59] through [70], wherein one or more pharmaceutically acceptable excipients comprises a lubricant, wherein the lubricant comprises magnesium stearate and wherein the composition is in the form of a 20, 70, or 100 mg tablet or capsule, wherein the amount of magnesium stearate is about 0.5% w/w. In one aspect, the form is tablet. In one aspect, the form is capsule.

Embodiment [73]

The pharmaceutical composition of any one of embodiments [1] through [72] may further be film coated.

Embodiment [74]

The pharmaceutical composition of any one of embodiments [1] through [73], wherein the amount of film-coating agent by weight based on a core tablet is from about 1% to about 10% w/w.

Embodiment [75]

The pharmaceutical composition of any one of embodiments [1] through [74], wherein the amount of film-coating agent by weigh based on a core tablet is from about 1.5% to about 7% w/w.

Embodiment [76]

The pharmaceutical composition of any one of embodiments [1] through [75], wherein the amount of film-coating agent by weight based on a core tablet from about 2% to about 5% w/w.

Embodiment [77]

The pharmaceutical composition of any one of embodiments [1] through [76], wherein the film coating enveloping the core tablet of the film-coated tablet contains at least one or more pharmaceutically acceptable film-forming agents.

Embodiment [78]

The pharmaceutical composition of any one of embodiments [1] through [77], wherein the film coating enveloping the core tablet of the film-coated tablet contains at least one or more pharmaceutically acceptable film-forming agents, wherein the film-forming agent comprises hypromellose.

Embodiment [79]

The pharmaceutical composition of any one of embodiments [1] through [78], wherein the film coating of the film-coated tablet may contain one or more plasticisers and/or one or more colored pigments.

Embodiment [80]

The pharmaceutical composition of any one of embodiments [1] through [79], wherein film coating of the film-coated tablet may contain one or more plasticisers and/or one or more colored pigments, wherein the plasticiser comprises polyethylene glycol.

Embodiment [81]

The pharmaceutical composition of any one of embodiments [1] through [80], wherein film coating of the film-coated tablet may contain one or more plasticisers and/or one or more colored pigments, and wherein the colored pigments comprise titanium dioxide and ferric oxide.

Embodiment [82]

The pharmaceutical composition of any one of any one of embodiments [1] through [81], wherein the film coating of the film-coated tablets comprises from about 20% to about 95% w/w of film forming agent.

Embodiment [83]

The pharmaceutical composition of any one of embodiments [1] through [82], wherein the film coating of the film-coated tablets comprises from about 50% to about 90% w/w of film forming agent.

Embodiment [84]

The pharmaceutical composition of any one of embodiments [1] through [83], wherein the film coating of the film-coated tablets comprises from about 5% to about 40% w/w of plasticizer.

Embodiment [85]

The pharmaceutical composition of any one of embodiments [1] through [84], wherein the film coating of the film-coated tablets comprises from about 8% to about 30% w/w of plasticizer.

Embodiment [86]

The pharmaceutical composition of any one of embodiments [1] through [85], wherein the film coating of the film-coated tablets comprises from about 0.1% to about 10% w/w of colored pigment.

Embodiment [87]

The pharmaceutical composition of any one of embodiments [1] through [86], wherein the film coating of the film-coated tablets comprises from about 0.3% to about 5% w/w of colored pigment.

Film coats may be prepared from a premix film coating agent, wherein the premix film coating agent comprises the trade name OPADRY®. Examples of film coating agents include OPADRY® Red 03F45081 (1008 g) (manufactured by COLORCON® JAPAN; containing hypromellose 2910, macrogol 6000, titanium oxide and red ferric oxide) and OPADRY® Yellow 03F42240 (2016 g) (manufactured by COLORCON® JAPAN; containing hypromellose 2910, macrogol 6000, titanium oxide and yellow ferric oxide).

Embodiment [88]

A pharmaceutical composition which is:

| Pharmaceutical Composition Formulation | (% w/w) |
|---|---|
| solid dispersion extrudate | 10.0 |
| microcrystalline cellulose | 80.0 |
| croscarmellose sodium | 5.0 |
| colloidal silicon dioxide | 4.5 |
| magnesium stearate | 0.5 |
| solid dispersion extrudate | 20.0 |
| microcrystalline cellulose | 70.0 |
| croscarmellose sodium | 5.0 |
| colloidal silicon dioxide | 4.5 |
| magnesium stearate | 0.5 |
| solid dispersion extrudate | 40 |
| microcrystalline cellulose | 47.0 |
| croscarmellose sodium | 8.0 |
| colloidal silicon dioxide | 4.5 |
| Magnesium stearate | 0.5 |
| Solid Dispersion Extrudate | 20.0 |
| microcrystalline cellulose | 74.0 |
| croscarmellose sodium | 5.0 |
| colloidal silicon dioxide | 0.5 |
| magnesium stearate | 0.5 |
| total core tablet | 100.0 |
| OPADRY ® Red (% of core tablet weight) | 4.2 |
| Solid Dispersion Extrudate | 32.4 |
| microcrystalline cellulose | 58.6 |
| croscarmellose sodium | 8.0 |
| colloidal silicon dioxide | 0.5 |
| magnesium stearate | 0.5 |
| total core tablet | 100.0 |
| OPADRY ® Yellow (% of core tablet weight) | 3.3 |
| Solid Dispersion Extrudate | 40.0 |
| microcrystalline cellulose | 51.0 |
| roscarmellose sodium | 8.0 |
| colloidal silicon dioxide | 0.5 |
| magnesium stearate | 0.5 |
| total core tablet | 100.0 |
| OPADRY ® Red (% of core tablet weight) | 1.12 |
| OPADRY ® Yellow (% of core tablet weight) | 2.24 |

Embodiment [89]

The pharmaceutical composition of any one of embodiments [1] through [88], wherein the pharmaceutical composition is substantially amorphous. In one aspect, the substantially amorphous pharmaceutical composition comprises an amount of crystalline Compound 1 or a pharmaceutically acceptable salt thereof. In one aspect, the amount of crystalline Compound 1 is less than about 30%, less than about 29%, less than about 28%, less than about 27%, less than about 26%, less than about 25%, less than about 20%, less than about 15%, less than about 10%, less than about 5%, less than about 4%. In one aspect, the substantially amorphous pharmaceutical composition is produced upon re-crystallization of Compound 1 or a pharmaceutically acceptable salt thereof in a pharmaceutical composition originally comprising amorphous solid dispersion extrudate.

The amorphous character of a pharmaceutical composition can be detected using analytical methods, including but not limited to, microscopic methods (scanning electronic microscopy (SEM), polarized light microscopy (PLM), hot stage microscopy (HSM)), thermal methods (differential scanning calorimetry (DSC) modulated DSC (mDSC), diffraction methods (XRPD), and spectroscopic methods (FT-Infrared (IR), FT-Ramen, solid state NMR (ssNMR) and confocal raman microscopy (CRM)). In one aspect, the amorphous character of a pharmaceutical composition is detected by X-ray powder diffraction (XRPD).

In one aspect, the amount of crystalline substance in a substantially amorphous pharmaceutical composition can be determined using a calibration curve based on samples of variable crystalline content (high and low regions). In one aspect, the amount of crystalline Compound 1 or a pharmaceutically acceptable salt thereof in a substantially amorphous pharmaceutical composition of the invention may affect the solubility of the composition. In one aspect, the amount of crystalline Compound 1 or a pharmaceutically acceptable salt thereof in a substantially amorphous pharmaceutical composition of the invention may affect the bioavailability of the composition. In one aspect, less than about 30% of crystalline Compound 1 or a pharmaceutically acceptable salt thereof in a substantially amorphous pharmaceutical composition does not reduce the solubility and/or bioavailability of the composition. In another aspect, less than about 29%, less than about 28%, less than about 27%, less than about 26%, less than about 24%, less than about 25%, less than about 20%, less than about 15%, less than about 10%, less than about 5%, less than about 4% of crystalline Compound 1 or a pharmaceutically acceptable salt thereof in a substantially amorphous pharmaceutical composition does not significantly reduce the solubility and/or bioavailability of the composition.

Embodiment [90]

A solid dispersion extrudate comprising (1) Compound 1 or a pharmaceutically acceptable salt thereof and (2) a vinylpyrrolidinone-vinyl acetate copolymer.

Embodiment [91]

The solid dispersion extrudate of embodiment [90], comprising (1) from about 30% to about 50% w/w of Compound 1 or a pharmaceutically acceptable salt thereof and (2) from about 70% to about 50% w/w of a vinylpyrrolidinone-vinyl acetate copolymer.

Embodiment [92]

The solid dispersion extrudate of any one of embodiments [90] through [91], comprising (1) from about 35% to about 45% w/w of Compound 1 or a pharmaceutically acceptable salt thereof and (2) from about 65% to about 55% w/w of a vinylpyrrolidinone-vinyl acetate copolymer.

Embodiment [93]

The solid dispersion extrudate of any one of embodiments [90] through [92], comprising (1) about 40% w/w of Compound 1 or a pharmaceutically acceptable salt thereof and (2) about 60% w/w of a vinylpyrrolidinone-vinyl acetate copolymer.

Embodiment [94]

The solid dispersion of any one of embodiments [90] through [93], wherein the solid dispersion extrudate comprises Compound 1. In one aspect, Compound 1 is present as substantially pure. "Substantially pure" means greater than ninety-five percent pure.

Embodiment [95]

The solid dispersion of any one of embodiments [90] through [93], wherein the solid dispersion extrudate comprises a pharmaceutically acceptable salt of Compound 1.

Embodiment [95A]

The solid dispersion of any one of embodiments [90] through [95], wherein the vinylpyrrolidinone-vinyl acetate copolymer is copovidone.

Compound 1 or a pharmaceutically acceptable salt thereof used in this invention, may be in crystalline form, amorphous form or substantially amorphous form prior to formulation of the solid dispersion. FIG. 8 is a representative XRPD pattern of Compound 1 as a crystalline form.

It will be understood that any of the above embodiments may be combined to form additional embodiments.

Process for Preparing Pharmaceutical Compositions

The present invention relates to processes for the preparation of pharmaceutical compositions comprising the pan-Raf kinase inhibitor Compound 1 or a pharmaceutically acceptable salt thereof. Processes for the preparation of the pharmaceutical compositions of the invention are explained in the following.

Specifically, the processes for the preparation of the pharmaceutical compositions of the invention generally involve an extrusion process followed by a formulation process. Formation of an inactive chiral impurity was observed and determined to be directly related to the thermal production technique employed, necessitating a significant amount of work for the development of the extrusion process. Incorporation of processing additives such as poloxamer and polysorbate failed to show any significant reduction in the level of chiral impurity formation. Additionally, the processing additives appeared to compromise amorphous stability of the solid dispersion. Process optimization studies ultimately achieved a reduction of impurity formation through control of the extrusion conditions related to melt residence time.

Figure 1A:
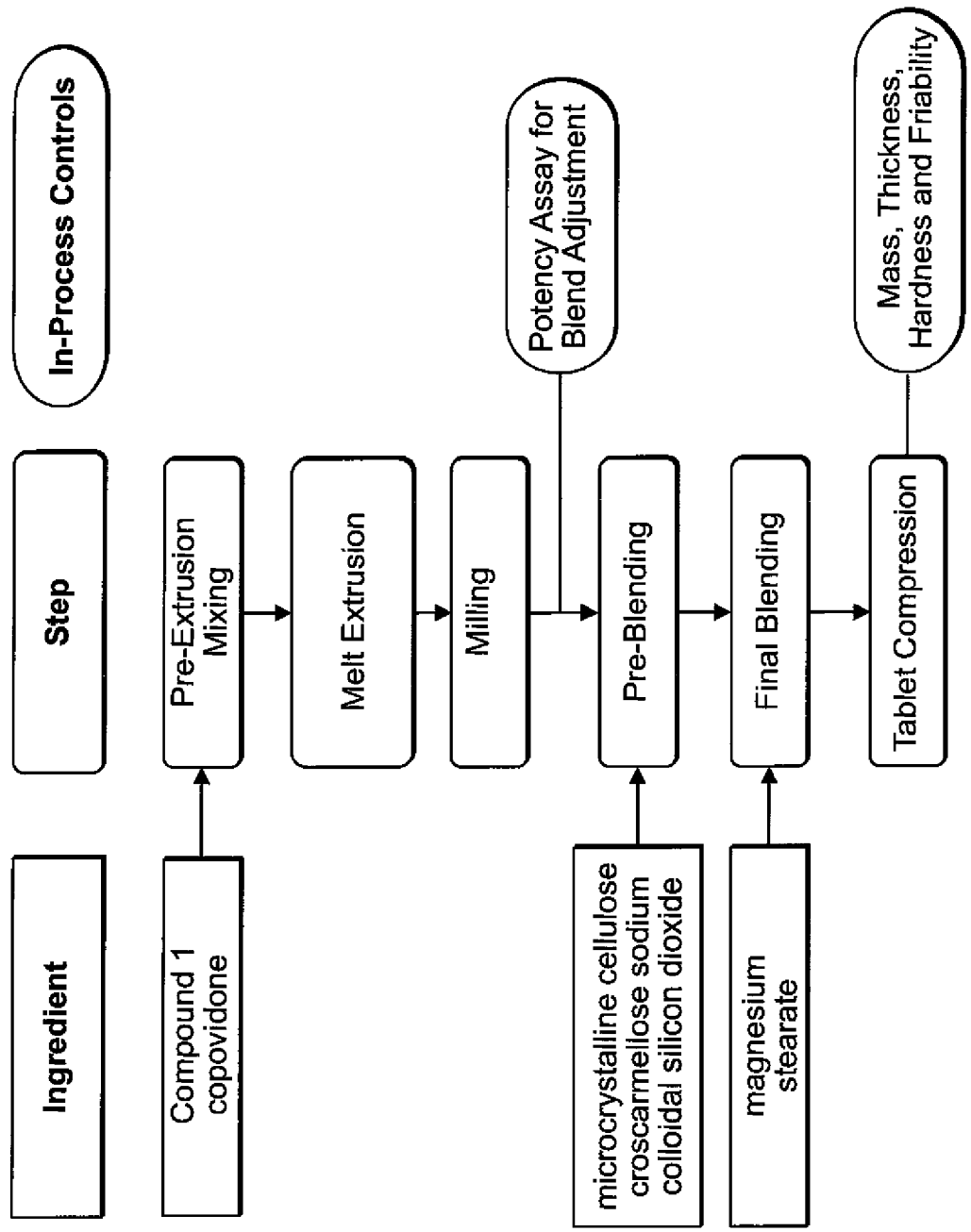
FIG. 1A is a flow diagram illustrating a representative process for the preparation of pharmaceutical compositions of the invention corresponding to tablets produced according to Example 1, 2, or 3.
Figure 1B:
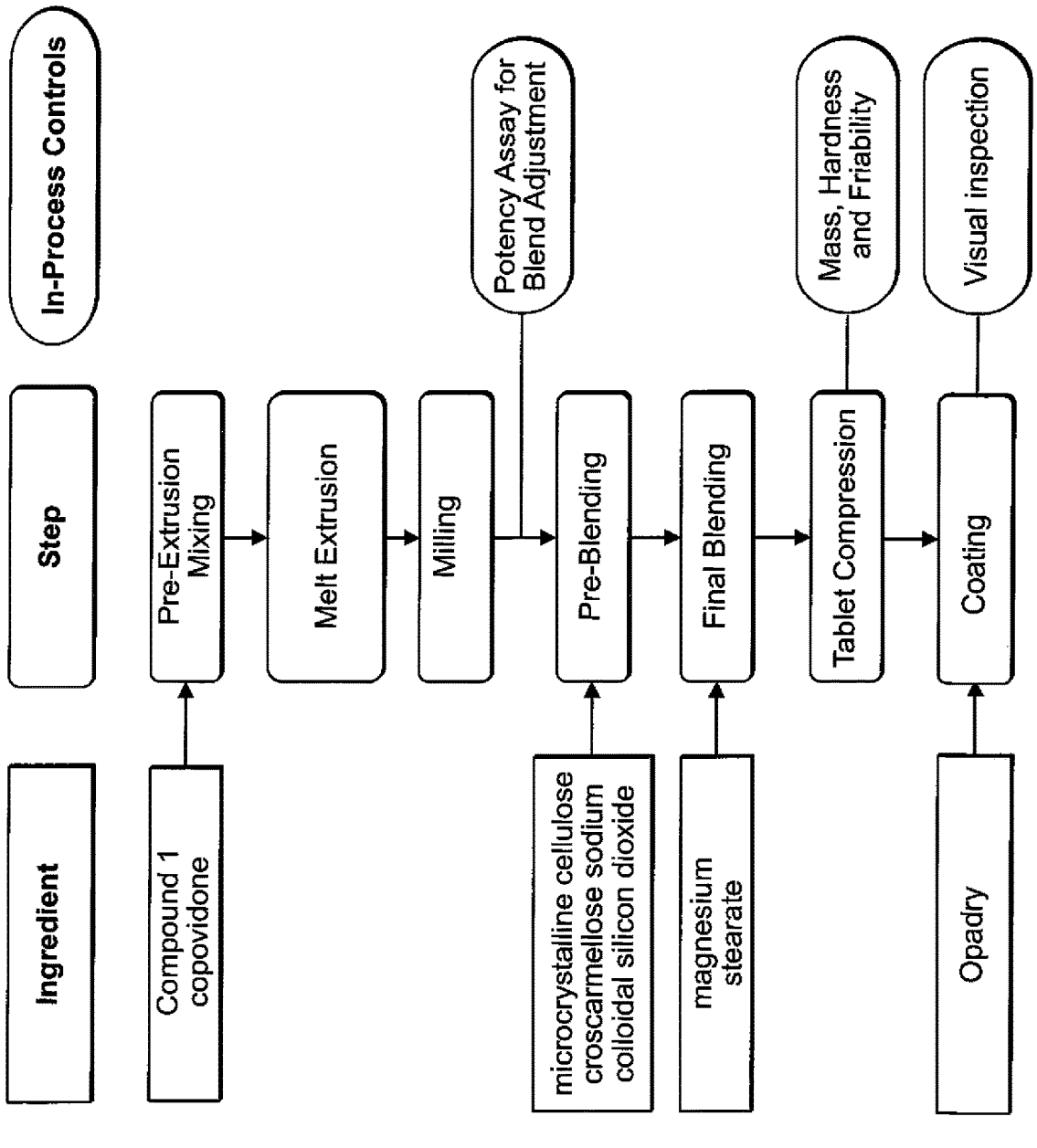
FIG. 1B is a flow diagram illustrating a representative process for the preparation of pharmaceutical compositions of the invention corresponding to tablets produced according to Examples 1, 4, 5, and 6.

The extrusion process involves the addition of vinylpyrrolidinone-vinyl acetate copolymer e.g., Kollidon® VA 64 to Compound 1 to form a solid dispersion extrudate. The formulation process involves the addition of microcrystalline cellulose, croscamellose sodium, colloidal silicon dioxide, and magnesium sterarate to the solid dispersion extrudate produced by the extrusion process to form a pharmaceutical composition of the invention. FIG. 1A is a flow diagram illustrating a representative process for the preparation of the pharmaceutical compositions of the invention according to Example 1, 2, and 3. In FIG. 1, pre-extrusion mixing, melt extrusion, and milling are steps in the extrusion process and pre-blending and final blending are steps in the formulation process. FIG. 1B is a flow diagram illustrating a representative process for the preparation of the pharmaceutical compositions of the invention produced according to Example 1, 4, 5, and 6. In FIG. 1B, pre-extrusion mixing, melt extrusion, and milling are steps in the extrusion process and pre-blending, final blending, tablet compression and coating are steps in the formulation process.

Compound 1 and a vinylpyrrolidinone-vinyl acetate copolymer e.g., copovidone are ingredients of the extrusion process. Microcrystalline cellulose, croscamellose sodium, colloidal silicon dioxide, and magnesium sterarate are ingredients of the formulation process to be added to the resulting solid dispersion extrudate produced by the extrusion process. OPADRY® as film-coating agent is an ingredient of the formulation process to be added to core tablets with the final blended powder.

Specifically, in the extrusion process, Compound 1 and vinylpyrrolidinone-vinyl acetate copolymer e.g., copovidone are accurately weighed, screened and mixed using high shear mixing to form a pre-extrusion powder mixture.

A suitable hot melt extruder (e.g. twin screw, Leistritz Nano-16 mm or Micro-18 mm) is set up with the appropriate supporting equipment, including a cooling conveyor (e.g., Domer model 220M060600D0169 or Nara TBC-309-DC) and feeder with auger (e.g., K-Tron Gravimeteric Feeder e.g., with dual flight 20 mm auger). Example processing parameters are as follows: feed rate: 2.0 kg/hr; screw speed: 250 rpm; and barrel temperature: 170, 140, 90, 50° C. or 1.0 kg/hr; screw speed: 275 rpm; and barrel temperature: 175, 140, 90, 50° C. Compound 1 exhibits a relatively high melting point at 204° C. and thermal gravimetric analysis (TGA) showed Compound 1 to be relatively stable at elevated temperatures below 200° C.

The powder mixture is fed into the hot melt extruder, and the resulting solid dispersion extrudate is cooled and milled using a suitable impact mill with hammer forward configuration (e.g., Fizmill L1A hammer mill) or multi pin rotor (e.g., NARA Sample mill SAM). The milled extrudate may be screened using a suitable screen (e.g., 20 mesh operated at 9,000 rpm) to remove oversize material and then screened through a second suitable screen (e.g., 60 mesh). The resulting solid dispersion extrudate is taken forward to the formulation process. Alternatively, only part of the resulting solid dispersion extrude is taken forward to the formulation process.

In one aspect of the formulation process e.g., FIG. 1A, the ingredients are added sequentially to the solid dispersion extrudate: microcrystalline cellulose (e.g., Avicel PH 102, FMC Biopolymer), croscarmellose sodium (Ac-Di-Sol®, FMC Biopolymer), and may be screened using a suitable screen (e.g., 18-mesh). Colloidal silicon dioxide (Aerosil 200, Evonik) is added and may be screened using a suitable screen (e.g., 40-mesh) to produce a pre-blend, which is blended e.g., for about 20 minutes using a diffusion class blender. Magnesium stearate (Mallinckrodt) is accurately weighed, may be screened with a suitable screen (e.g., 30-mesh) and blended with the pre-blend to produce the final blend. Blend e.g, for 20 minutes using a diffusion class blender. In one aspect, the final blend is compressed on a tablet press into tablets. In another aspect, the final blend is loaded into a capsule.

In another aspect of the formulation process e.g, FIG. 1B, the ingredients are added sequentially to the solid dispersion extrudate: microcrystalline cellulose (e.g., Avicel PH 101, FMC Biopolymer), croscarmellose sodium (Ac-Di-Sol®, FMC Biopolymer) and colloidal silicon dioxide (Aerosil 200, Evonik) are added to produce a pre-blend, which is blended e.g., for about 15 minutes using a diffusion class blender. Magnesium stearate (Mallinckrodt) is accurately weighed, may be screened with a suitable screen (e.g., seive size 1.0 mm) and blended with the pre-blend to produce the final blend. Blend e.g, for 5 minutes using a diffusion class blender. The final blend is compressed on a tablet press into core tablets. The core tablets are charged into a suitable film coating machine (e.g. Driacoater Vario 500/600) and are coated with the spray suspension with premix film coating agent (e.g. OPADRY®, Colorcon).

The present invention includes the following embodiments:

Embodiment [96]

A process for preparing a pharmaceutical composition, which comprises the steps of:
(i) extruding a mixture of Compound 1 or a pharmaceutically acceptable salt thereof and vinylpyrrolidinone-vinyl acetate copolymer to form a solid dispersion extrudate;
(ii) blending the resulting solid dispersion extrudate with one or more pharmaceutically acceptable excipients.

Embodiment [97]

A process for preparing a pharmaceutical composition, which comprises the steps of:
(i) extruding a mixture of Compound 1 or a pharmaceutically acceptable salt thereof and vinylpyrrolidinone-vinyl acetate copolymer to form a solid dispersion extrudate;
(ii) blending the resulting solid dispersion extrudate with a filler, disintegrant, and glidant to form a pre-blend; and
(iii) blending a lubricant with the resulting pre-blend.

Embodiment [98]

The process of any one of embodiments [96] through [97], wherein the process further comprises the step of (iv-A) compressing the pharmaceutical composition resulting from steps (i), (ii), and (iii) into tablet form or loading the pharmaceutical composition from steps (i), (ii), and (iii) into capsule form.

Embodiment [99]

The process of any one of embodiments [96] through [98], wherein the process further comprises the step of (iv-A) compressing the pharmaceutical composition resulting from steps (i), (ii), and (iii) into tablet form. In one aspect, tablet form provides improved bioavailability.

Embodiment [100]

The process of any one of embodiments [96] through [99], wherein the process further comprises the step of (v) coating the pharmaceutical composition resulting from step (iv) into a film coated tablet form. In one aspect, the film coated tablet form provides improved bioavailability.

Embodiment [101]

The process of any one of embodiments [96] through [98], wherein the process further comprises the step of (iv-B) loading the pharmaceutical composition resulting from steps (i), (ii), and (iii) into capsule form.

Embodiment [102]

The process of any one of embodiments [96] through [101], wherein the mixture in step (i) is Compound 1 and vinylpyrrolidinone-vinyl acetate copolymer.

Embodiment [103]

The process of any one of embodiments [96] through [101], wherein the mixture in step (i) is the pharmaceutically acceptable salt of Compound 1 and vinylpyrrolidinone-vinyl acetate copolymer.

Embodiment [104]

The process of any one of embodiments [96] through [103], wherein the vinylpyrrolidinone-vinyl acetate copolymer is copovidone. In one aspect, the copovidone is Kollidon® VA 64. In one aspect, the vinylpyrrolidinone-vinyl acetate copolymer is pre-dried. In one aspect, copovidone is pre-dried at 60° C. for about 8 hours.

Embodiment [105]

The process of any one of embodiments [96] through [104], wherein the amount of Compound 1 is from about 3% to about 17% w/w.

Embodiment [106]

The process of any one of embodiments [96] through [105], wherein the amount of Compound 1 is from about 7% to about 17% w/w.

Embodiment [107]

The process of any one of embodiments [96] through [106], wherein the amount of Compound 1 is from about 8% to about 16% w/w.

Embodiment [108]

The process of any one of embodiments [96] through [105] for preparing a composition comprising a 5 mg tablet or capsule, wherein the amount of Compound 1 is about 4% w/w. In one aspect, the form is tablet. In one aspect, the form is capsule.

Embodiment [109]

The process of any one of embodiments [96] through [107] for preparing a composition comprising a 20 mg tablet or capsule, wherein the amount of Compound 1 is about 8% w/w. In one aspect, the form is tablet. In one aspect, the form is capsule.

Embodiment [110]

The process of any one of embodiments [96] through [107] for preparing a composition comprising a 70 mg tablet or capsule, wherein the amount of Compound 1 is about 13% w/w. In one aspect, the form is tablet. In one aspect, the form is capsule.

Embodiment [111]

The process of any one of embodiments [96] through [107] for preparing a composition comprising a 100 mg tablet or capsule, wherein the amount of Compound 1 is about 16% w/w. In one aspect, the form is tablet. In one aspect, the form is capsule.

Embodiment [112]

The process of any one of embodiments [96] through [111], wherein the amount of vinylpyrrolidinone-vinyl acetate copolymer is from about 5% to about 25% w/w. In one aspect, the copolymer is copovidone. In one aspect, the amount of copovidone is from about 5% to about 25% w/w.

Embodiment [113]

The process of any one of embodiments [96] through [112], wherein the amount of vinylpyrrolidinone-vinyl acetate copolymer in is from about 12% to about 24% w/w. In one aspect, the copolymer is copovidone. In one aspect, the amount of copovidone is from about 12% to about 24% w/w.

Embodiment [114]

The process of any one of embodiments [96] through [105], [108], or [112] through [113], for preparing a composition comprising a 5 mg tablet or capsule, wherein the amount of vinylpyrrolidinone-vinyl acetate copolymer is about 6% w/w. In one aspect, the copolymer is copovidone. In one aspect, the amount of copovidone is about 6% w/w. In one aspect, the form is tablet. In one aspect, the form is capsule.

Embodiment [115]

The process of any one of embodiments [96] through [107], [109], or [112] through [113], for preparing a composition comprising a 20 mg tablet or capsule, wherein the amount of vinylpyrrolidinone-vinyl acetate copolymer about 12% w/w. In one aspect, the copolymer is copovidone. In one aspect, the amount of copovidone is about 12% w/w. In one aspect, the form is tablet. In one aspect, the form is capsule.

Embodiment [116]

The process of any one of embodiments [96] through [107], [110], or [112] through [113], for preparing a composition comprising a 70 mg tablet or capsule, wherein the amount of vinylpyrrolidinone-vinyl acetate copolymer about 19% w/w. In one aspect, the copolymer is copovidone. In one aspect, the amount of copovidone is about 19% w/w. In one aspect, the form is tablet. In one aspect, the form is capsule.

Embodiment [117]

The process of any one of embodiments [96] through [107] or through [113], for preparing a composition comprising a 100 mg tablet or capsule, wherein the amount of vinylpyrrolidinone-vinyl acetate copolymer is about 24% w/w. In one aspect, the copolymer is copovidone. In one aspect, the amount of copovidone is about 24% w/w. In one aspect, the form is tablet. In one aspect, the form is capsule.

Embodiment [118]

The process of any one of embodiments [96] through [117], wherein the process further comprises the step of (i-A) cooling and milling the resulting extrudate prior to step (ii).

Embodiment [119]

The process of any one of embodiments [96] through [118], wherein the process further comprises the step of (i-A) cooling and milling the resulting extrudate prior to step (ii) and the step of (i-B) screening the milled extrudate after step (i-A) and prior to step (ii).

Embodiment [120]

The process of any one of embodiments [96] through [119], wherein the process further comprises before step (i) providing a mixture wherein high shear mixing is used to prepare the mixture of Compound 1 or a pharmaceutically acceptable salt thereof and vinylpyrrolidinone-vinyl acetate copolymer.

High shear mixing can minimize potency variations (FIG. 5).

Embodiment [121]

The process of any one of embodiments [96] through [120], wherein the extruding is carried out in an extruder operating at a screw speed of from about 225 rpm to about 350 rpm.

Embodiment [122]

The process of any one of embodiments [96] through [121], wherein the extruding is carried out in an extruder operating at a screw speed of about 250 rpm.

Embodiment [123]

The process of any one of embodiments [96] through [121], wherein the extruding is carried out in an extruder operating at a screw speed of about 275 rpm.

Embodiment [124]

The process of any one of embodiments [96] through [123], wherein the extruding is carried out in an extruder after the mixture is fed into the extruder at a feed rate of from about 0.5 kg/hr to about 2.5 kg/hr. The feeding section of the extruder transfers the feed stock into the barrel of the extruder.

Embodiment [125]

The process of any one of embodiments [96] through [124], wherein the extruding is carried out in an extruder after the mixture is fed into the extruder at a feed rate of from about 1.0 kg/hr to about 2.0 kg/hr.

Embodiment [126]

The process of any one of embodiments [96] through [125], wherein the extruding is carried out in an extruder after the mixture is fed into the extruder at a feed rate of about 1.0 kg/hr.

Embodiment [127]

The process of any one of embodiments [96] through [126], wherein the extruding is carried out in an extruder operating with a barrel temperature comprising a gradient temperature profile ranging from about room temperature to about 180° C. In one aspect, implementation of a gradient temperature profile yields a significant reduction in chiral impurity levels during manufacture. For example, increasing the temperature provides a decrease in residual crystalline form of the extrudate.

Embodiment [128]

The process of any one of embodiments [96] through [127], wherein the extruding is carried out in an extruder operating with a barrel temperature comprising a gradient temperature profile ranging from about 50° C. to about 170° C.

Embodiment [129]

The process of any one of embodiments [96] through [128], wherein the extruding is carried out in an extruder operating with a barrel temperature comprising a gradient temperature profile comprising four temperature zones from (1) about 50° C., (2) about 90° C., (3) about 140° C. and (4) about 170° C. to about 175° C. In one aspect, lower barrel temperatures yields compositions with lower chiral impurity levels.

Embodiment [130]

The process of any one of embodiments [96] through [129], wherein the extruding is carried out in an extruder operating with a barrel temperature comprising a gradient temperature profile comprising four temperature zones from (1) about 50° C., (2) about 90° C., (3) about 140° C. and (4) about 170° C. In one aspect, lower barrel temperatures yields compositions with lower chiral impurity levels.

Embodiment [131]

The process of any one of embodiments [96] through [129], wherein the extruding is carried out in an extruder operating with a barrel temperature comprising a gradient temperature profile comprising four temperature zones from (1) about 50° C., (2) about 90° C., (3) about 140° C. and (4) about 175° C. In one aspect, lower barrel temperatures yields compositions with lower chiral impurity levels.

Embodiment [132]

The process of any one of embodiments [96] through [131], wherein the solid dispersion extrudate in step (i) is amorphous. For example, the solid dispersion extrudate is amorphous as detected by XRPD (FIG. 6). In another aspect, the amorphous character of the solid dispersion extrudate can be detected using differential scanning calorimety (DSC).

Embodiment [133]

The process of any one of embodiments [96] through [132], wherein the loading of extrudate is from about 10% to about 50% w/w.

Embodiment [134]

The process of any one of embodiment [96] through [133], wherein the loading of the extrudate is from about 10% to about 40% w/w.

Embodiment [135]

The process of any one of embodiment [96] through [134], wherein, the loading of extrudate is about from about 40% to about 50% w/w. In one aspect, the loading of the extrudate is important for disintegration rate. In one aspect, a tablet form prepared at about 40% solid dispersion exhibits rapid dissolution, and achieves full release in less than 10 minutes.

Embodiment [136]

The process of any one of embodiments [96] through [105], [108], [112] through [114], [118] through [134] for preparing a composition comprising a 5 mg tablet or capsule comprising about 10% w/w of a solid dispersion extrudate comprising Compound 1 or a pharmaceutically acceptable salt thereof and a vinylpyrrolidinone-vinyl acetate copolymer and (2) about 90% w/w of one or more pharmaceutically acceptable excipients. In one aspect, the form is tablet. In one aspect, the form is capsule.

Embodiment [137]

The process of any one of embodiments [96] through [107], [109], [112] through [113], [115], or [118] through [134] for preparing a composition comprising a 20 mg tablet or capsule comprising about 20% w/w of a solid dispersion extrudate comprising Compound 1 or a pharmaceutically acceptable salt thereof and a vinylpyrrolidinone-vinyl acetate copolymer and (2) about 80% w/w of one or more pharmaceutically acceptable excipients. In one aspect, the form is tablet. In one aspect, the form is capsule.

Embodiment [138]

The process of any one of embodiments [96] through [107], [110], [112] through [113], [116], or [118] through [134], for preparing a composition comprising a 70 mg tablet or capsule comprising about 32% w/w of a solid dispersion extrudate comprising Compound 1 or a pharmaceutically acceptable salt thereof and a vinylpyrrolidinone-vinyl acetate copolymer and (2) about 68% w/w of one or more pharmaceutically acceptable excipients. In one aspect, the form is tablet. In one aspect, the form is capsule.

Embodiment [139]

The process of any one of embodiments [96] through [107], through [113] or [117] through [135] for preparing a composition of a 100 mg tablet or capsule comprising about 40% w/w of a solid dispersion extrudate comprising Compound 1 or a pharmaceutically acceptable salt thereof and a vinylpyrrolidinone-vinyl acetate copolymer and (2) about 60% w/w of one or more pharmaceutically acceptable excipients. In one aspect, the form is tablet. In one aspect, the form is capsule.

Embodiment [140]

The process of any one of embodiments [96] through [139], wherein one or more pharmaceutically acceptable excipients comprises a disintegrant and wherein the disintegrant comprises croscarmellose sodium. In one aspect, carscarmellose sodium serves as a disintegrant for immediate release. In one aspect, disintegration is a function of the type of superdisintegrant and solid dispersion loading within the formulation.

Embodiment [141]

The process of any one of embodiments [96] through [140], wherein one or more pharmaceutically acceptable excipients comprises a disintegrant and wherein the disintegrant is carscarmellose sodium and the amount of croscarmellose sodium is from about 4% to about 9% w/w.

Embodiment [142]

The process of any one of embodiments [96] through [141], wherein one or more pharmaceutically acceptable excipients comprises a disintegrant and wherein the disintegrant is carscarmellose sodium and the amount of croscarmellose sodium is from about 5% to about 8% w/w.

Embodiment [143]

The process of any one of embodiments [96] through [109], through [115], [118] through [134], [136] through [137], or [140] through [142] for preparing a composition comprising a 5 mg or 20 mg tablet or capsule, wherein one or more pharmaceutically acceptable excipients comprises a disintegrant and wherein the disintegrant is croscarmellose sodium and the amount of croscarmellose sodium is about 5% w/w. In one aspect, the form is tablet. In one aspect, the form is capsule.

Embodiment [144]

The process of any one of embodiments [96] through [107], [110], [112] through [113], [116], [118] through [134], [138], or [140] through [142], for preparing a composition comprising a 70 mg tablet or capsule, wherein one or more pharmaceutically acceptable excipients comprises a disintegrant and wherein the disintegrant is croscaramellose sodium and the amount of croscarmellose sodium is about 8% w/w. In one aspect, the form is tablet. In one aspect, the form is capsule.

Embodiment [145]

The process of any one of embodiments [96] through [107], through [113], [117] through [135], or [139] through [142], for preparing a composition comprising a 100 mg tablet or capsule, wherein one or more pharmaceutically acceptable excipients comprises a disintegrant and wherein the disintegrant is croscaramellose sodium and the amount of croscarmellose sodium is about 8% w/w. In one aspect, the form is tablet. In one aspect, the form is capsule.

Embodiment [146]

The process of any one of embodiments [96] through [145], wherein one or more pharmaceutically acceptable excipients comprises a glidant and wherein the glidant comprises colloidal silicon dioxide. In one aspect, the colloidal silicon dioxide aids the flow property of the formulation blend.

Embodiment [147]

The process of any one of embodiments [96] through [146], wherein one or more pharmaceutically acceptable excipients comprises a glidant and wherein the glidant is colloidal silicon dioxide and the amount of colloidal silicon dioxide is from about 0.5% to about 6% w/w.

Embodiment [148]

The process of any one of embodiments [96] through [147], wherein one or more pharmaceutically acceptable excipients comprises a glidant and wherein the glidant is colloidal silicon dioxide and the amount of colloidal silicon dioxide is from about 3% to about 6% w/w.

Embodiment [149]

The process of any one of embodiments [96] through [146], wherein one or more pharmaceutically acceptable excipients comprises a glidant and wherein the glidant is colloidal silicon dioxide and the amount of colloidal silicon dioxide is from about 3.5% to about 4.5% w/w.

Embodiment [150]

The process of any one of embodiments [96] through [146], wherein one or more pharmaceutically acceptable excipients comprises a glidant and wherein the glidant is colloidal silicon dioxide and the amount of colloidal silicon dioxide is from about 0.5% to about 5% w/w.

Embodiment [151]

The process of any one of embodiments [96] through [146], wherein one or more pharmaceutically acceptable excipients comprises a glidant and wherein the glidant is colloidal silicon dioxide and the amount of colloidal silicon dioxide is from about 0.5% to about 2% w/w.

Embodiment [152]

The process of any one of embodiments [96] through [109], through [115], [117] through [137], [139] through [143], or [145] through [150], for preparing a composition comprising a 5, 20, or 100 mg tablet or capsule, wherein one or more pharmaceutically acceptable excipients comprises a glidant and wherein the amount of colloidal silicon dioxide is about 4.5% w/w. In one aspect, the form is capsule. In one aspect, the form is tablet.

Embodiment [153]

The process of any one of embodiments [96] through [107], through [113], [115] through [135], [135] through

31

[151], for preparing a composition comprising a 20, 70 or 100 mg tablet or capsule, wherein one or more pharmaceutically acceptable excipients comprises a glidant and wherein the amount of colloidal silicon dioxide is about 0.5% w/w. In one aspect, the form is capsule. In one aspect, the form is tablet.

Embodiment [154]

The process of any one of embodiments [96] through [153], wherein one or more pharmaceutically acceptable excipients comprises a filler and wherein the filler is microcrystalline cellulose.

Embodiment [155]

The process of any one of embodiments [54] through [154], wherein one or more pharmaceutically acceptable excipients comprises a filler and wherein the filler is microcrystalline cellulose and the amount of microcrystalline cellulose is from about 46% to about 81% w/w.

Embodiment [156]

The process of any one of embodiments [96] through [155], wherein one or more pharmaceutically acceptable excipients comprises a filler and wherein the filler is microcrystalline cellulose and the amount of microcrystalline cellulose is from about 40% to about 80% w/w.

Embodiment [157]

The process of any one of embodiments [96] through [156], wherein one or more pharmaceutically acceptable excipients comprises a filler and wherein the filler is microcrystalline cellulose and the amount of microcrystalline cellulose is from about 51% to about 74% w/w.

Embodiment [158]

The process of any one of embodiments [96] through [157], wherein one or more pharmaceutically acceptable excipients comprises a filler and wherein the filler is microcrystalline cellulose and the amount of microcrystalline cellulose is from about 47% to about 70% w/w.

Embodiment [159]

The process of any one of embodiments [96] through [105], [108], [112] through [114], [118] through [133], [136], [140] through [143], [146] through [152], or [154] through [156] for preparing a composition comprising a 5 mg tablet or capsule, wherein one or more pharmaceutically acceptable excipients comprises a filler and wherein the filler is microcrystalline cellulose and the amount of microcrystalline cellulose is about 80% w/w. In one aspect, the form is tablet. In one aspect, the form is capsule.

Embodiment [160]

The process of any one of embodiments [96] through [107], [109], [112] through [113], [115], [118] through [134], [137], [140] through [143], or [146] through [158], for preparing a composition comprising a 20 mg tablet or capsule, wherein one or more pharmaceutically acceptable excipients comprises a filler and wherein the filler is microcrystalline cellulose and the amount of microcrystalline cellulose is from about 74% to about 70% w/w. In one aspect, the form is tablet. In one aspect, the form is capsule.

Embodiment [161]

The process of any one of embodiments [96] through [107], [109], [112] through [113], [115], [118] through [134], [137], [140] through [143], or [146] through [158], for preparing a composition comprising a 20 mg tablet or capsule, wherein one or more pharmaceutically acceptable excipients comprises a filler and wherein the filler is microcrystalline cellulose and the amount of microcrystalline cellulose is about 70% w/w. In one aspect, the form is tablet. In one aspect, the form is capsule.

Embodiment [162]

The process of any one of embodiments [96] through [107], [109], [112] through [113], [115], [118] through [134], [137], [140] through [143], or [146] through [158], for preparing a composition comprising a 20 mg tablet or capsule, wherein one or more pharmaceutically acceptable excipients comprises a filler and wherein the filler is microcrystalline cellulose and the amount of microcrystalline cellulose is about 74% w/w. In one aspect, the form is tablet. In one aspect, the form is capsule.

Embodiment [163]

The process of any one of embodiments [96] through [107], [110], [112] through [113], [116], [118] through [134], [138], [140] through [142], [144], or through [151], or [154] through [158], for preparing a composition comprising a 70 mg tablet or capsule, wherein one or more pharmaceutically acceptable excipients comprises a filler and wherein the filler is microcrystalline cellulose and the amount of microcrystalline cellulose is about 59% w/w. In one aspect, the form is tablet. In one aspect, the form is capsule.

Embodiment [164]

The process of any one of embodiments [96] through [107], through [113], [117] through [135], [139] through [142], [145] through [151], [153] through [156], or [158], for preparing a composition comprising a 100 mg tablet or capsule, wherein one or more pharmaceutically acceptable excipients comprises a filler and wherein the filler is microcrystalline cellulose and the amount of microcrystalline cellulose is about 47% w/w. In one aspect, the form is tablet. In one aspect, the form is capsule.

Embodiment [165]

The process of any one of embodiments [96] through [164], wherein one or more pharmaceutically acceptable excipients comprises a lubricant and wherein the lubricant comprises magnesium stearate. In one aspect, the magnesium stearate provides lubrication of the formulation during compression.

Embodiment [166]

The process of any one of embodiments [96] through [165], wherein one or more pharmaceutically acceptable excipients comprises a lubricant and wherein the lubricant is magnesium stearate and the amount of magnesium stearate is from about 0.3% to about 0.7% w/w.

Embodiment [167]

The process of any one of embodiments [96] through [166], wherein one or more pharmaceutically acceptable excipients comprises a lubricant and wherein the lubricant is magnesium stearate and the amount of magnesium stearate is from about 0.4% to about 0.5% w/w.

Embodiment [168]

The process of any one of embodiments [96] through [167], wherein one or more pharmaceutically acceptable excipients comprises a lubricant and wherein the lubricant is magnesium stearate and the amount of magnesium stearate is about 0.5% w/w.

Embodiment [169]

The process of any one of embodiments [96] through [107], through [113], [118] through [135], [137] through [143], [146] through [158], or [160] through [168], for preparing a composition comprising a 20, 70, or 100 mg tablet or capsule, wherein one or more pharmaceutically acceptable excipients comprises a lubricant and wherein the lubricant is magnesium stearate and the amount of magnesium stearate is about 0.5% w/w. In one aspect, the form is tablet. In one aspect, the form is capsule.

Embodiment [170]

The process of embodiment any one of embodiments [96] through [109], [111] through [114], [116] through [135], [137] through [151], [153] through [156], [158], or [165] through [168], for preparing a composition comprising a 5, 20, or 100 mg tablet or capsule, wherein one or more pharmaceutically acceptable excipients comprises a lubricant and wherein the lubricant is magnesium stearate and the amount of magnesium stearate is about 0.5% w/w. In one aspect, the form is tablet. In one aspect, the form is capsule.

Embodiment [171]

The process of any one of embodiments [96] through [170], wherein one or more pharmaceutically acceptable excipients comprises a film coating agent. In one aspect, the film coating agent comprises OPADRY®.

Embodiment [172]

The process of any one of embodiments [96] through [171], wherein one or more pharmaceutically acceptable excipients comprises a film coating agent and wherein the film coating agent comprises OPADRY® and wherein the amount of OPADRY® is from about 0.5% to about 5% w/w.

Embodiment [173]

The process of any one of embodiments [96] through [172], wherein one or more pharmaceutically acceptable excipients comprises a film coating agent and wherein the film coating agent comprises OPADRY® and the amount of OPADRY® is from about 3.3% to about 4.2% w/w.

Embodiment [174]

The process of any one of embodiments [96] through [173] for preparing a composition comprising a 20 mg tablet, wherein one or more pharmaceutically acceptable excipients comprises a film coating agent and wherein the film coating agent is OPADRY® and the amount of OPADRY® is about 4.2% w/w.

Embodiment [175]

The process of any one of embodiments [96] through [173] for preparing a composition comprising a 70 mg tablet, wherein one or more pharmaceutically acceptable excipients comprises a film coating agent and wherein the film coating agent is OPADRY® and the amount of OPADRY® is about 3.3% w/w.

Embodiment [176]

The process of any one of embodiments [96] through [173] for preparing a composition comprising a 100 mg tablet, wherein one or more pharmaceutically acceptable excipients comprises a film coating agent and wherein the film coating agent is OPADRY® and the amount of OPADRY® is about 3.4% w/w.

Embodiment [177]

A process for preparing a pharmaceutical composition, which comprises the steps of:
(i) extruding a mixture of Compound 1 or a pharmaceutically acceptable salt thereof and vinylpyrrolidinone-vinyl acetate copolymer to form a solid dispersion extrudate;
(ii) blending the resulting solid dispersion extrudate with filler, disintegrant, and glidant to form a pre-blend; and
(iii) blending a lubricant with the resulting pre-blend;
wherein the pharmaceutical composition prepared comprises:
from about 3% to about 17% w/w Compound 1 or a pharmaceutically acceptable salt thereof;
from about 5% to about 25% w/w vinylpyrrolidinone-vinyl acetate copolymer;
from about 4% to about 9% w/w disintegrant;
from about 3% to about 6% w/w glidant;
from about 46% to about 81% w/w filler; and
from about 0.3% to about 0.7% w/w lubricant.

Embodiment [178]

A process for preparing a pharmaceutical composition, which comprises the steps of: (i) extruding a mixture of Compound 1 and copovidone to form a solid dispersion extrudate;
(ii) blending the resulting solid dispersion extrudate with filler, disintegrant, and glidant to form a pre-blend; and
(iii) blending a lubricant with the resulting pre-blend;
wherein the pharmaceutical composition prepared comprises:
from about 3% to about 17% w/w Compound 1;
from about 5% to about 25% w/w copovidone;
from about 4% to about 9% w/w croscarmellose;
from about 3% to about 6% w/w glidant;
from about 46% to about 81% w/w filler; and
from about 0.3% to about 0.7% w/w lubricant.

Embodiment [179]

A process for preparing a pharmaceutical composition, which comprises the steps of:
(i) extruding a mixture of Compound 1 or a pharmaceutically acceptable salt thereof and vinylpyrrolidinone-vinyl acetate copolymer to form a solid dispersion extrudate;
(ii) blending the resulting solid dispersion extrudate with filler, disintegrant, and glidant to form a pre-blend; and
(iii) blending a lubricant with the resulting pre-blend;
(iv) compressing the resulting final blend to form core tablets;
(v) coating the core tablets with a film-coating agent;
wherein the pharmaceutical composition prepared comprises:
from about 3% to about 17% w/w Compound 1 or a pharmaceutically acceptable salt thereof;
from about 5% to about 25% w/w vinylpyrrolidinone-vinyl acetate copolymer;
from about 4% to about 9% w/w disintegrant;
from about 0.1% to about 5% w/w glidant;
from about 40% to about 80% w/w filler; and
from about 0.3% to about 0.7% w/w lubricant
from about 0.5% to about 5% w/w film-coating agent.

Embodiment [180]

A process for preparing a pharmaceutical composition, which comprises the steps of:
(i) extruding a mixture of Compound 1 and copovidone to form a solid dispersion extrudate;
(ii) blending the resulting solid dispersion extrudate with filler, disintegrant, and glidant to form a pre-blend; and
(iii) blending a lubricant with the resulting pre-blend;
(iv) compressing the resulting final blend to form core tablets;
(v) coating the core tablets with a film-coating agent;
wherein the pharmaceutical composition prepared comprises:
from about 3% to about 17% w/w Compound 1;
from about 5% to about 25% w/w copovidone;
from about 4% to about 9% w/w croscarmellose;
from about 3% to about 6% w/w glidant;
from about 46% to about 81% w/w filler; and
from about 0.3% to about 0.7% w/w lubricant
from about 0.5% to about 5% w/w coating agent.

Embodiment [181]

A pharmaceutical composition prepared by the process of any of embodiments [96] through [180].

Embodiment [182]

A pharmaceutical composition prepared by a process comprising the steps of:
(i) extruding a mixture of Compound 1 or a pharmaceutically acceptable salt thereof and vinylpyrrolidinone-vinyl acetate copolymer to form a solid dispersion extrudate;
(ii) blending the resulting solid dispersion extrudate with one or more pharmaceutically acceptable excipients.

Embodiment [183]

A pharmaceutical composition prepared by a process comprising the steps of:
(i) extruding a mixture of Compound 1 or a pharmaceutically acceptable salt thereof and vinylpyrrolidinone-vinyl acetate copolymer to form a solid dispersion extrudate;
(ii) blending the resulting solid dispersion extrudate with filler, disintegrant, and glidant to form a pre-blend; and
(iii) blending a lubricant with the resulting pre-blend.

Embodiment [184]

A pharmaceutical composition prepared by a process comprising the steps of:
(i) extruding a mixture of Compound 1 and copovidone to form a solid dispersion extrudate;
(ii) blending the resulting solid dispersion extrudate with filler, disintegrant, and glidant to form a pre-blend; and
(iii) blending a lubricant with the resulting pre-blend;
wherein the pharmaceutical composition prepared comprises:
from about 3% to about 17% w/w Compound 1;
from about 5% to about 25% w/w copovidone;
from about 4% to about 9% w/w croscarmellose;
from about 3% to about 6% w/w glidant;
from about 46% to about 81% w/w filler; and
from about 0.3% to about 0.7% w/w lubricant.

Embodiment [185]

The pharmaceutical composition of any one of embodiments or [184], wherein the pharmaceutical composition is substantially amorphous. In one aspect, the substantially amorphous pharmaceutical composition comprises an amount of crystalline Compound 1 or a pharmaceutically acceptable salt thereof. In one aspect, the amount of crystalline Compound 1 is less than about 30%, less than about 29%, less than about 28%, less than about 27%, less than about 26%, less than about 25%, less than about 20%, less than about 15%, less than about 10%, less than about 5%, less than about 4%.

Embodiment [186]

A pharmaceutical composition comprising as an active ingredient Compound 1 or a pharmaceutically acceptable salt thereof, wherein the active ingredient is in a solid dispersion form comprising vinylpyrrolidinone-vinyl acetate copolymer.

Embodiment [187]

The pharmaceutical composition of embodiment [186], wherein the copolymer is copovidone.

Embodiment [188]

The pharmaceutical composition of embodiments [186] or [187], wherein the pharmaceutical composition is substantially amorphous. In one aspect, the substantially amorphous pharmaceutical composition comprises an amount of crystalline Compound 1 or a pharmaceutically acceptable salt thereof. In one aspect, the amount of crystalline Compound 1 is less than about 30%, less than about 29%, less than about 28%, less than about 27%, less than about 26%, less than about 25%, less than about 20%, less than about 15%, less than about 10%, less than about 5%, less than about 4%.

Embodiment [188A]

A method of improving the absorption of Compound 1 or a pharmaceutically acceptable salt thereof, by combining with a vinylpyrrolidinone-vinyl acetate copolymer to form an amorphous system.

Embodiment [188B]

The method of embodiment [188A], wherein the vinylpyrrolidinone-vinyl acetate copolymer is copovidone.

It will be understood that any of the above embodiments may be combined to form additional embodiments.

Utility of the Pharmaceutical Compositions of the Invention

The MAP kinase pathway is a central signal transduction pathway that is dysregulated in a large number of cancers and developmental disorders. Normally, binding of a growth factor to its receptor switches on RAS, which, in turn, activates one or more of the RAF kinase family members, ARAF, BRAF and CRAF (Raf-1). RAF kinases perpetuate the signal by phosphorylating and activating MEK, another kinase that phosphorylates a third kinase, ERK. ERK then phosphorylates a number of key growth-, survival-, or differentiation-promoting targets.

Of the proteins in the cascade, RAF kinases have the most complex regulatory mechanisms, including the ability to form dimers. RAF dimerization is acknowledged to be a required step for RAF signaling in multiple cellular contexts including normal RAS-dependent RAF activation. Furthermore in some oncogenic settings, RAF dimerization contributes to the pathogenic role of the pathway. Specifically, RAF signals as a dimer in settings where oncogenic mutations affect NRAS as well as in settings where there are point mutations of the BRAF protein that do not target the amino acid V600 of K601.

RAF dimerization has also been found to alter the therapeutic response and disease progression in patients treated with type-1 BRAF ATP-competitive inhibitors (such as vemurafenib). In these settings there is inhibitor-induced RAF heterodimerization that leads to the inadvertent activation of the downstream pathway. This phenomenon is known as paradoxical activation of the MAP kinase pathway and is thought to be the mechanism by which type-1 BRAF inhibitors induce certain adverse events, including the formation of squamous cell carcinomas (SCC). It is for this reason that treatment with type-1 BRAF inhibitors may be contraindicated in cancer settings where mutations in the RAS family or the V600 or K601 BRAF mutations occur.

Type-1 BRAF ATP-competitive inhibitors have been developed to target BRAF V600* mutations (such as V600E) that occur in melanoma, thyroid, colon cancer and NSCLC. These type-1 BRAF inhibitors have demonstrated clinical benefit for patients with this mutation. The responses observed in these patients can be explained by differences in RAF signaling. In these settings, BRAF functions as a RAF monomer rather than as a RAF dimer. This RAF monomer, signals independent of upstream growth stimuli and leads to constitutive activation of the BRAT monomeric protein. As discussed above, type-1 BRAF inhibitors may be withheld for cancers in the RAF dimer setting. Whereas, a pan-RAF inhibitor such as Compound 1 could in principle work in settings of RAF dimerization in distinct mutant contexts, e.g., BRAF and NRAS.

Preclinical models have suggested that a higher maximum tolerated dose of Compound 1 may achieve better stasis or tumor regression. Pharmacodynamic effects of Compound 1 in melanoma tumor tissues further support this hypothesis. Accordingly, it has now been discovered that the pharmaceutical compositions of the present invention comprising Compound 1 can be administered so as to achieve a higher maximum tolerated dose, and thus a higher effective amount, if it is administered using an intermittent dosing regimen.

Accordingly, the present invention relates to methods of treating cancer in settings of RAF dimerization in the context of BRAF and NRAS positive-mutated cancers, comprising administering such pharmaceutical compositions described herein to a patient according to an intermittent dosing regimen and to the use of such pharmaceutical compositions described herein in the manufacture of medicaments.

The present invention includes the following embodiments:

Embodiment [189]

A method for the treatment of cancer in a patient in need of such treatment, comprising administering an effective amount of a pharmaceutical composition as described herein, for example, the pharmaceutical compositions described in embodiments [1] through [89] or [181] through [188] to the patient according to an intermittent dosing regimen, wherein the dosing regimen comprises administering the composition once or twice a week and the amount of the composition administered each week is from about 400 mg to about 1000 mg.

Embodiment [190]

A method for the treatment of cancer in a patient in need of such treatment, comprising administering an effective amount of a pharmaceutical composition, wherein the pharmaceutical composition comprises (1) a solid dispersion extrudate comprising Compound 1 or a pharmaceutically acceptable salt thereof and a vinylpyrrolidinone-vinyl acetate copolymer and (2) one or more pharmaceutically acceptable excipients, to the patient according to an intermittent dosing regimen, wherein the dosing regimen comprises administering the composition once or twice a week and the amount of the composition administered each week is from about 400 mg to about 1000 mg.

Embodiment [191]

The method of embodiment [190], wherein the pharmaceutical composition comprises (1) a solid dispersion extrudate comprising Compound 1 and a vinylpyrrolidinone-vinyl acetate copolymer and (2) one or more pharmaceutically acceptable excipients.

Embodiment [192]

The method of embodiment [191], wherein the pharmaceutical composition comprises (1) a solid dispersion extrudate comprising Compound 1 and copovidone and (2) one or more pharmaceutically acceptable excipients.

Embodiment [193]

The method of any one of embodiments [189] through [192], wherein the dosing regimen comprises administering to the patient the composition once a week with a rest period of 6 days between each administration.

Embodiment [194]

The method of any one of embodiments [189] through [193], wherein the dosing regimen comprises administering the composition in a single dose. For example, the amount of the composition to be administered for the week is administered a single dose on days 1, 8, 15, and 22 of a 28-day cycle.

Embodiment [195]

The method of any one of embodiments [189] through [194], wherein the dosing regimen comprises administering the composition in a split dose. For example, "administering the composition in a split dose" means administering at one time point half of the composition to be administered for the week and administering at a later time point the remaining half of the composition. In one aspect, the two half doses are administered on the same day e.g., days 1, 8, 15, and 22 of a 28-day cycle. In one aspect, the two half doses are administered at different time points that are about 12 hours apart. In one aspect, the two half doses are administered at different time points that are 12 hours apart.

Embodiment [196]

The method of embodiment [195], wherein dosing regimen comprises administering the composition in a split dose on two different days. For example, the two half doses are administered on two different days e.g., days 1 and 2, days 8 and 9, days 15 and 16, and days 22 and 23 of a 28-day cycle.

Embodiment [197]

The method of any one of embodiments [189] through [196], wherein the amount of the composition administered each week is from about 800 mg to about 1000 mg.

Embodiment [198]

The method of any one of embodiments [189] through [196], wherein the amount of the composition administered each week is from about 400 mg to about 900 mg.

Embodiment [199]

The method of any one of embodiments [189] through [196], wherein the amount administered each week is from about 500 mg to about 900 mg.

Embodiment [200]

The method of any one of embodiments [189] through [196], wherein the amount administered each week is from about 600 mg to about 800 mg.

Embodiment [201]

The method of any one of embodiments [189] through [196], wherein the amount administered each week is from about 400 mg to about 600 mg.

Embodiment [202]

The method of any one of embodiments [189] through [196], wherein the amount administered each week is from about 400 mg to about 700 mg.

Embodiment [203]

The method of any one of embodiments [189] through [196], wherein the amount administered each week is from about 600 mg to about 700 mg.

Embodiment [204]

The method of any one of embodiments [189] through [196], wherein the amount administered each week is about 300 mg.

Embodiment [205]

The method of any one of embodiments [189] through [196], wherein the amount administered each week is about 400 mg.

Embodiment [206]

The method of any one of embodiments [189] through [196], wherein the amount administered each week is about 500 mg.

Embodiment [207]

The method of any one of embodiments [189] through [196], wherein the amount administered each week is about 600 mg.

Embodiment [208]

The method of any one of embodiments [189] through [196], wherein the amount administered each week is about 700 mg.

Embodiment [209]

The method of any one of embodiments [189] through [196], wherein the amount administered each week is about 800 mg.

Embodiment [210]

The method of any one of embodiments [189] through [196], wherein the amount administered each week is about 900 mg.

Embodiment [211]

The method of any one of embodiments [189] through [196], wherein the cancer is a solid tumor cancer.

Embodiment [212]

The method of any one of embodiments [189] through [196], wherein the cancer is relapsed.

Embodiment [213]

The method of any one of embodiments [189] through [196], wherein the cancer is refractory.

Embodiment [214]

The method any one of embodiments [189] through [213], wherein the cancer is BRAF and/or NRAS positive cancer.

As used herein, "BRAF" refers to B-Raf proto-oncogene, serine/threonine kinase, the gene associated with the mRNA sequence assigned as GenBank Accession No. NM_004333, SEQ ID NO:1 (open reading frame is SEQ ID NO:2, nucleotides 62 to 2362 of SEQ ID NO:1), encoding GenPept Accession No. NP_004324, SEQ ID NO:3). Other names for BRAF include rafB1 and Noonan Syndrome 7 (NS7). BRAF functions as a serine/threonine kinase, has a role in regulating the MAP kinase/ERKs signaling pathway and can be found on chromosome 7q.

As used herein, "NRAS" refers to neuroblastoma RAS viral (v-ras) oncogene homolog, the gene associated with the mRNA sequence assigned as GenBank Accession No. NM_002524, SEQ ID NO:4 (open reading frame is SEQ ID NO:5, nucleotides 255 to 824 of SEQ ID NO:4), encoding GenPept Accession No. NP_002515, SEQ ID NO:6). Other names for NRAS include Autoimmune Lymphoproliferative Syndrome type IV (ALPS4), NRAS1, and Noonan Syndrome 6 (NS6). NRAS functions as an oncogene with GTPase activity and can be found on chromosome 1p. NRAS interacts with the cell membrane and various effector proteins, such as Raf and RhoA, which carry out its signaling function through the cytoskeleton and effects on cell adhesion (Fotiadou et al. (2007) *Mol. Cel. Biol.* 27:6742-6755).

As used herein, the phrase "BRAF positive cancer," "BRAF mutation-positive cancer," "BRAF positive-mutation cancer," or "BRAF positive-mutation cancer" means the cancer has one or more mutations in BRAF gene. As used herein "NRAS positive cancer," "NRAS mutation-positive cancer," "NRAS positive-mutated cancer," or "NRAS positive mutation cancer" means the cancer has one or more mutations in NRAS gene. In one aspect, the cancer is BRAF wild type and has one or more mutations in NRAS gene. In one aspect, the cancer is NRAS wild type and has one or more mutations in BRAF gene. In one aspect, the cancer has one or more mutations in both BRAF gene and NRAS gene.

Embodiment [215]

The method of any one of embodiments [189] through [214], wherein the cancer is BRAF mutation-positive cancer.

Embodiment [216]

The method of any one of embodiments [189] through [215], wherein the one or more BRAF mutation is in exon 15 or 11.

Embodiment [217]

The method of any one of embodiments [189] through [216], wherein the one or more BRAF mutation is in codon 464-469, 600 or 601.

Embodiment [218]

The method of any one of embodiments [189] through [217], wherein the BRAF mutation is V600 mutation. In one aspect, the V600 mutation is V600E, V600G, V600A, or V600K; V600E, V600D, or V600K; or V600E, V600D, V600M, V600G, V600A, V600R, or V600K. In one aspect, the BRAF mutation is V600E. In one aspect, the BRAF mutation is V600D. In one aspect, the BRAF mutation is V600K. "V600E mutation" means substitution of glutamic acid for valine at the amino acid position of 600. "V600K mutation" means substitution of lysine for valine at the amino acid position of 600. "V600D mutation" means substitution of aspartic acid for valine at the amino acid position of 600. "V600G mutation" means substitution of glycine for valine at the amino acid position of 600. "V600A mutation" means substitution of alanine for valine at the amino acid position of 600. "V600M mutation" means substitution of methionine for valine at the amino acid position of 600. "V600R mutation" means substitution of arginine for valine at the amino acid position of 600.

Embodiment [219]

The method of any one of embodiments [189] through [218], wherein the one or more BRAF mutation is non-V600E mutation. In one aspect, one or more non-V600E mutation is G466A, G466V, N581S, D594H, R146W, L613F, D565_splice, S394*, P367R, G469A, G469V, G469*, G466V, G464V, G397S, S113I, A762E, G469L, D594N, G596S, G596R, D594N, D594H, or G327_splice. In one aspect, one or more non-V600E mutations are G469R, R95T, A621_splice, V639I, Q609H, G464V, or G466V. The asterisk "*" means a stop codon.

Embodiment [220]

The method of any one of embodiments [189] through [219], wherein the cancer is NRAS mutation-positive cancer.

Embodiment [221]

The method of any one of embodiments [189] through [220], wherein one or more NRAS mutation is in exon 3 or exon 4.

Embodiment [222]

The method of any one of embodiments [189] through [221], wherein one or more NRAS mutation is in codon 59, 61, 117, or 146.

Embodiment [223]

The method of any one of embodiments [189] through [222], wherein NRAS mutation is Q61. In one aspect, NRAS mutation is Q61R, Q61K, Q61L, Q61H, or Q61P. In one aspect, NRAS mutation is Q61R.

Embodiment [224]

The method of any one of embodiments [189] through [223], wherein the cancer is skin, ocular, gastrointestinal, thyroid, breast, ovarian, lung, brain, laryngeal, cervical, lymphatic system, genitourinary tract, or bone cancer.

Embodiment [225]

The method of any one of embodiments [189] through [224], wherein the cancer is skin cancer.

Embodiment [226]

The method of any one of embodiments [189] through [224], wherein the cancer is ocular cancer.

Embodiment [227]

The method of any one of embodiments [189] through [224], wherein the cancer is thyroid cancer.

Embodiment [228]

The method of any one of embodiments [189] through [224], wherein the cancer is breast cancer.

Embodiment [229]

The method of any one of embodiments [189] through [224], wherein the cancer is ovarian cancer.

Embodiment [230]

The method of any one of embodiments [189] through [224], wherein the cancer is lung cancer.

Embodiment [231]

The method of any one of embodiments [189] through [224], wherein the cancer is brain cancer.

Embodiment [232]

The method of any one of embodiments [189] through [224], wherein the cancer is laryngeal cancer.

Embodiment [233]

The method of any one of embodiments [189] through [224], wherein the cancer is gastrointestinal cancer.

Embodiment [234]

The method of any one of embodiments [189] through [224], wherein the cancer is cervical cancer.

Embodiment [235]

The method of any one of embodiments [189] through [224], wherein the cancer is lymphatic system cancer.

Embodiment [236]

The method of any one of embodiments [189] through [224], wherein the cancer is genitourinary tract cancer.

Embodiment [237]

The method of any one of embodiments [189] through [224], wherein the cancer is bone cancer. In one aspect, the bone cancer is multiple myeloma.

Embodiment [238]

The method of any one of embodiments [189] through [225], wherein the cancer is skin cancer. In one aspect, the skin cancer is melanoma. In one aspect, the melanoma is locally advanced, metastatic and/or unresectable melanoma. In one aspect, the melanoma is locally advanced. In one aspect, the melanoma is metastatic. In aspect, the melanoma is unresectable melanoma. In one aspect, the melanoma is BRAF mutation-positive melanoma. In one aspect, the melanoma is BRAF mutation-positive cutaneous melanoma. In one aspect, BRAF mutation is selected from V600E, V600K, and V600D mutation. In one aspect, BRAF mutation is V600E. In one aspect, BRAF mutation is V600K. In one aspect, BRAF mutation is V600D. In one aspect, the melanoma is NRAS mutation-positive melanoma. In one aspect, the melanoma is NRAS mutation-positive cutaneous melanoma. In one aspect, the melanoma is BRAF/NRAS mutation negative cutaneous melanoma (wild type). In one aspect, the melanoma is of cutaneous, uveal, or mucosal origin. In one aspect, the melanoma is of cutaneous origin. In one aspect, the melanoma is of uveal origin. In one aspect, the melanoma is of mucosal origina.

Embodiment [239]

The method any one of embodiments [189] through [224], wherein the cancer is ocular cancer. In one aspect, the ocular cancer is ocular melanoma.

Embodiment [240]

The method of any one of embodiments [189] through [224], wherein the cancer is brain cancer. In one aspect, the brain cancer is glioma, neuroblastoma or astrocytoma. In one aspect, the brain cancer is glioma. In one aspect, the brain cancer is neuroblastoma. In one aspect, the cancer is astrocytoma.

Embodiment [241]

The method of any one of embodiments [189] through [224], wherein the cancer is genitourinary tract cancer. In one aspect, the genitourinary tract cancer is bladder or prostate cancer. In one aspect, the cancer is bladder cancer. In one aspect, the cancer is prostate cancer.

Embodiment [242]

The method of any one of embodiments [189] through [224], wherein the cancer is papillary thyroid cancer.

Embodiment [243]

The method of any one of embodiments [189] through [224], wherein the cancer is a gastrointestinal cancer. In one aspect, the gastrointestinal cancer is esophageal, stomach, colorectal, liver, renal, pancreatic, or gallbladder cancer. In one aspect the gastrointestinal cancer is esophageal cancer. In one aspect the gastrointestinal cancer is stomach cancer. In one aspect the gastrointestinal cancer is colorectal cancer. In one aspect the gastrointestinal cancer is liver cancer. In one aspect the gastrointestinal cancer is renal cancer. In one aspect, the gastrointestinal cancer is pancreatic cancer. In one aspect the gastrointestinal cancer is gallbladder cancer.

Embodiment [244]

A method for the treatment of melanoma in a patient in need of such treatment, comprising administering an effective amount of a pharmaceutical composition according to any one of embodiments [1] through [89] or [181] through [188] to the patient according to an intermittent dosing regimen, wherein the dosing regimen comprises administering the composition once weekly and the amount of the composition administered each week is from about 400 mg to about 700 mg, wherein the melanoma is BRAF wild type and has a mutation in NRAS gene. In one aspect, NRAS mutation is in exon 3 or 4. In one aspect, NRAS mutation is Q61. In one aspect, the melanoma is relapsed and/or refractory.

Embodiment [245]

A method for the treatment of melanoma in a patient in need of such treatment, comprising administering an effective amount of a pharmaceutical composition according to any one of embodiments [1] through [89] or [181] through [188] to the patient according to an intermittent dosing regimen, wherein the dosing regimen comprises administering the composition once weekly and the amount of the composition administered each week is from about 400 mg to about 700 mg, wherein the melanoma has a mutation in BRAF gene. In one aspect, BRAF mutation is in exon 15 or 11. In one aspect, BRAF mutation is V600. In one aspect, BRAF mutation is V600E. In one aspect, the melanoma is relapsed and/or refractory.

Embodiment [246]

A method for the treatment of colorectal cancer in a patient in need of such treatment, comprising administering an effective amount of a pharmaceutical composition according to any one of embodiments [1] through [89] or [181] through [188] to the patient according to an intermittent dosing regimen, wherein the dosing regimen comprises administering the composition once weekly and the amount of the composition administered each week is from about 400 mg to about 700 mg, wherein the colorectal cancer has a mutation in BRAF gene. In one aspect, BRAF mutation is in exon 15 or 11. In one aspect, the BRAF mutation is V600. In one aspect, BRAF mutation is V600E.

Embodiment [247]

A method for the treatment of non-small cell lung cancer in a patient in need of such treatment, comprising administering an effective amount of a pharmaceutical composition according to any one of embodiments [1] through [89] or [181] through [188] to the patient according to an intermittent dosing regimen, wherein the dosing regimen comprises administering the composition once weekly and the amount of the composition administered each week is from about 400 mg to about 700 mg, wherein the non-small cell lung cancer has a mutation in BRAF gene. In one aspect, BRAF mutation is non-V600E. In one aspect, BRAF mutation is in exon 15 or 11. In one aspect, the BRAF mutation is V600. In one aspect, BRAF mutation is V600E.

Embodiment [248]

A method for the treatment of colorectal cancer in a patient in need of such treatment, comprising administering an effective amount of a pharmaceutical composition according to any one of embodiments [1] through [89] or [181] through [188] to the patient according to an intermittent dosing regimen, wherein the dosing regimen comprises administering the composition once weekly and the amount of the composition administered each week is from about 400 mg to about 700 mg, wherein the colorectal cancer has a mutation in NRAS gene. In one aspect, NRAS mutation is in exon 3 or 4. In one aspect, NRAS mutation is in codon 59, 61, 117, or 146.

Embodiment [249]

A method for the treatment of thyroid cancer in a patient in need of such treatment, comprising administering an effective amount of a pharmaceutical composition according to any one of embodiments [1] through [89] or [181] through [188] to the patient according to an intermittent dosing regimen, wherein the dosing regimen comprises administering the composition once weekly and the amount of the composition administered each week is from about 400 mg to about 700 mg, wherein the thyroid cancer has a mutation in BRAF gene. In one aspect, the BRAF mutation is in exon 15 or 11. In one aspect, the BRAF mutation is V600. In one aspect, the BRAF mutation is V600E.

Embodiment [250]

The method of any one of embodiments [189] through [249], wherein the patient is naïve to prior therapy with one or more RAF and/or MEK inhibitors.

Embodiment [251]

The method of any one of embodiments [189] through [249], wherein the patient's response to previous treatment with RAF inhibitors and/or MEK inhibitors has 1) relapsed following an objective response, 2) failed to demonstrate an objective response, and/or 3) could not tolerate such a regimen due to unacceptable toxicity.

Embodiment [252]

The method of any one of embodiments [189] through [249], wherein the patient has received at least one line of prior anticancer therapy. In one aspect, the method is for treating a patient after failure of at least one standard chemotherapy.

Embodiment [253]

The method any one of embodiments [189] through [249], wherein the patient is naïve to any prior anticancer treatment except for treatment with ipilimumab, anti-PD-1, and/or anti-PDL-1 mAbs.

Embodiment [254]

A method for determining whether to treat a patient with a pharmaceutical composition of any one of embodiments [1] through [89] or [181] through [188] comprising:
  a) measuring at least one characteristic of at least one or more BRAF and/or NRAS markers associated with gene mutation in a patient sample comprising tumor cells;
  b) identifying whether the at least one characteristic measured in step a) is informative for outcome upon treatment with the pharmaceutical composition; and
  c) determining to treat the patient with the pharmaceutical composition if the informative characteristic indicates that the tumor cells comprise at least one marker gene with a BRAF and/or NRAS mutational status that

Embodiment [255]

The method of embodiment [254], wherein the at least one characteristic is sequence.

Embodiment [256]

The method of embodiment [254] or [255], wherein the mutational status of at least one of the BRAF and/or NRAS markers is mutant.

Embodiment [257]

The method of any one of embodiments [254] through [256], wherein the mutational status of the BRAE marker is mutant.

Embodiment [258]

The method of any one of embodiments [254] through [257], wherein the BRAF mutation is in exon 15 or 11.

Embodiment [259]

The method of any one of embodiments [254] through [258], wherein the one or more BRAF mutation is in codon 464-469, 600 or 601.

Embodiment [260]

The method of any one of embodiments [254] through [259], wherein the BRAF mutation is V600 mutation. In one aspect, the V600 mutation is V600E, V600G, V600A, or V600K; V600E, V600D, or V600K; or V600E, V600D, V600M, V600G, V600A, V600R, or V600K. In one aspect, the BRAF mutation is V600E.

Embodiment [261]

The method of any one of embodiments [254] through [260], wherein the BRAF mutation is a non-V600E mutation.

Embodiment [262]

The method of any one of embodiments [254] through [261], wherein the mutational status of the NRAS marker is mutant.

Embodiment [263]

The method of any one of embodiments [254] through [262], wherein the one or more NRAS mutation is in exon 3 or exon 4.

Embodiment [264]

The method of any one of embodiments [254] through [263], wherein the one or more NRAS mutation is in codon 59, 61, 117, or 146.

Embodiment [265]

The method of any one of embodiments [254] through [264], wherein the NRAS mutation is Q61. In one aspect, the NRAS mutation is Q61R, Q61K, Q61L, Q61H, or Q61P. In one aspect, the NRAS mutation is Q61R.

Embodiment [266]

A method for determining an increased likelihood of pharmacological effectiveness of treatment by a pharmaceutical composition as described herein in an patient diagnosed with cancer (particularly a cancer selected from those cancers described herein), said method comprising
  subjecting a nucleic acid sample from a cancer (tumor) sample from the patient to BRAF or NRAS mutational testing or PCR, wherein the presence of at least one mutation in BRAF or NRAS gene, such as e.g., one or more of those mutations described herein, indicates an increased likelihood of pharmacological effectiveness of the treatment.

Embodiment [267]

A method of treating a patient having cancer (particularly a cancer described herein), said method comprising:
  i) obtaining a nucleic acid sample from a cancer sample from said patient;
  ii) subjecting the sample to BRAF or NRAS mutational testing or PCR and identifying the presence of at least one mutation in BRAF or NRAS gene (such as e.g., one or more of those mutations described herein); and
  iii) administering an effective amount of a pharmaceutical composition as described herein to the patient in whose sample the presence of at least one mutation in BRAF or NRAS gene (such as e.g., one or more of those mutations described herein) is identified.

It will be understood that any of the above embodiments may be combined to form additional embodiments.

General Procedures

In some embodiments, a mutation in a marker can be identified by sequencing a nucleic acid, e.g., a DNA, RNA, cDNA or a protein correlated with the marker gene, e.g., a genotype marker gene, e.g., BRAF or NRAS. There are several sequencing methods known in the art to sequence nucleic acids. A nucleic acid primer can be designed to bind to a region comprising a potential mutation site or can be designed to complement the mutated sequence rather than the wild type sequence. Primer pairs can be designed to bracket a region comprising a potential mutation in a marker gene. A primer or primer pair can be used for sequencing one or both strands of DNA corresponding to the marker gene. A primer can be used in conjunction with a probe, e.g., a nucleic acid probe, e.g., a hybridization probe, to amplify a region of interest prior to sequencing to boost sequence amounts for detection of a mutation in a marker gene. Examples of regions which can be sequenced include an entire gene, transcripts of the gene and a fragment of the gene or the transcript, e.g., one or more of exons or untranslated regions or a portion of a marker comprising a mutation site. Examples of mutations to target for primer selection and sequence or composition analysis can be found in public databases which collect mutation information, such as Database of Genotypes and Phenotypes (dbGaP) maintained by the National Center for Biotechnology Information (Bethesda, Md.) and Catalogue of Somatic Mutations in Cancer (COSMIC) database maintained by the Wellcome Trust Sanger Institute (Cambridge, UK).

Sequencing methods are known to one skilled in the art. Examples of methods include the Sanger method, the SEQUENOM™ method and Next Generation Sequencing (NGS) methods. The Sanger method, comprising using electrophoresis, e.g., capillary electrophoresis to separate primer-elongated labeled DNA fragments, can be automated for high-throughput applications. The primer extension sequencing can be performed after PCR amplification of regions of interest. Software can assist with sequence base calling and with mutation identification. SEQUENOM™ MASSARRAY® sequencing analysis (San Diego, Calif.) is a mass-spectrometry method which compares actual mass to expected mass of particular fragments of interest to identify mutations. NGS technology (also called "massively parallel sequencing" and "second generation sequencing") in general provides for much higher throughput than previous methods and uses a variety of approaches (reviewed in Zhang et al. (2011) *J. Genet. Genomics* 38:95-109 and Shendure and Hanlee (2008) *Nature Biotech.* 26:1135-1145). NGS methods can identify low frequency mutations in a marker in a sample. Some NGS methods (see, e.g., GS-FLX Genome Sequencer (Roche Applied Science, Branford, Conn.), Genome analyzer (Illumina, Inc. San Diego, Calif.) SOLID™ analyzer (Applied Biosystems, Carlsbad, Calif.), Polonator G.007 (Dover Systems, Salem, N.H.), HELISCOPE™ (Helicos Biosciences Corp., Cambridge, Mass.)) use cyclic array sequencing, with or without clonal amplification of PCR products spatially separated in a flow cell and various schemes to detect the labeled modified nucleotide that is incorporated by the sequencing enzyme (e.g., polymerase or ligase). In one NGS method, primer pairs can be used in PCR reactions to amplify regions of interest. Amplified regions can be ligated into a concatenated product. Clonal libraries are generated in the flow cell from the PCR or ligated products and further amplified ("bridge" or "cluster" PCR) for single-end sequencing as the polymerase adds a labeled, reversibly terminated base that is imaged in one of four channels, depending on the identity of the labeled base and then removed for the next cycle. Software can aid in the comparison to genomic sequences to identify mutations. Another NGS method is exome sequencing, which focuses on sequencing exons of all genes in the genome. As with other NGS methods, exons can be enriched by capture methods or amplification methods.

In some embodiments, DNA, e.g., genomic DNA corresponding to the wild type or mutated marker can be analyzed both by in situ and by in vitro formats in a biological sample using methods known in the art. DNA can be directly isolated from the sample or isolated after isolating another cellular component, e.g., RNA or protein. Kits are available for DNA isolation, e.g., QIAAMP® DNA Micro Kit (Qiagen, Valencia, Calif.). DNA also can be amplified using such kits.

In another embodiment, mRNA corresponding to the marker can be analyzed both by in situ and by in vitro formats in a biological sample using methods known in the art. Many expression detection methods use isolated RNA. For in vitro methods, any RNA isolation technique that does not select against the isolation of mRNA can be utilized for the purification of RNA from tumor cells (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155). RNA can be isolated using standard procedures (see e.g., Chomczynski and Sacchi (1987) *Anal. Biochem.* 162:156-159), solutions (e.g., trizol, TRI REAGENT® (Molecular Research Center, Inc., Cincinnati, Ohio; see U.S. Pat. No. 5,346,994) or kits (e.g., a QIAGEN® Group RNEASY® isolation kit (Valencia, Calif.) or LEUKOLOCK™ Total RNA Isolation System, Ambion division of Applied Biosystems, Austin, Tex.).

Additional steps may be employed to remove DNA from RNA samples. Cell lysis can be accomplished with a non-ionic detergent, followed by microcentrifugation to remove the nuclei and hence the bulk of the cellular DNA. DNA subsequently can be isolated from the nuclei for DNA analysis. In one embodiment, RNA is extracted from cells of the various types of interest using guanidinium thiocyanate lysis followed by CsCl centrifugation to separate the RNA from DNA (Chirgwin et al. (1979) *Biochemistry* 18:5294-99). Poly(A)+RNA is selected by selection with oligo-dT cellulose (see Sambrook et al. (1989) *Molecular Cloning—A Laboratory Manual* (2nd ed.), Cold Spring Harbor Laboratory, Cold Spring Harbor, N.Y.). Alternatively, separation of RNA from DNA can be accomplished by organic extraction, for example, with hot phenol or phenol/chloroform/isoamyl alcohol. If desired, RNAse inhibitors may be added to the lysis buffer. Likewise, for certain cell types, it may be desirable to add a protein denaturation/digestion step to the protocol. For many applications, it is desirable to enrich mRNA with respect to other cellular RNAs, such as transfer RNA (tRNA) and ribosomal RNA (rRNA). Most mRNAs contain a poly(A) tail at their 3' end. This allows them to be enriched by affinity chromatography, for example, using oligo(dT) or poly(U) coupled to a solid support, such as cellulose or SEPHADEX® medium (see Ausubel et al. (1994) *Current Protocols In Molecular Biology*, vol. 2, Current Protocols Publishing, New York). Once bound, poly(A)+mRNA is eluted from the affinity column using 2 mM EDTA/0.1% SDS.

A characteristic of a marker of the invention in a sample, e.g., after obtaining a sample (e.g., a tumor biopsy) from a test subject, can be assessed by any of a wide variety of well known methods for detecting or measuring the characteristic, e.g., of a marker or plurality of markers, e.g., of a nucleic acid (e.g., RNA, mRNA, genomic DNA, or cDNA) and/or translated protein. Non-limiting examples of such methods include immunological methods for detection of secreted, cell-surface, cytoplasmic, or nuclear proteins, protein purification methods, protein function or activity assays, nucleic acid hybridization methods, optionally including "mismatch cleavage" steps (Myers, et al. (1985) *Science* 230:1242) to digest mismatched, i.e. mutant or variant, regions and separation and identification of the mutant or variant from the resulting digested fragments, nucleic acid reverse transcription methods, and nucleic acid amplification methods and analysis of amplified products. These methods include gene array/chip technology, RT-PCR, TAQMAN® gene expression assays (Applied Biosystems, Foster City, Calif.), e.g., under GLP approved laboratory conditions, in situ hybridization, immunohistochemistry, immunoblotting, FISH (flourescence in situ hybridization), FACS analyses, northern blot, southern blot, INFINIUM® DNA analysis Bead Chips (Illumina, Inc., San Diego, Calif.), quantitative PCR, bacterial artificial chromosome arrays, single nucleotide polymorphism (SNP) arrays (Affymetrix, Santa Clara, Calif.) or cytogenetic analyses.

Examples of techniques for detecting differences of at least one nucleotide between two nucleic acids include, but are not limited to, selective oligonucleotide hybridization, selective amplification, or selective primer extension. For example, oligonucleotide probes can be prepared in which the known polymorphic nucleotide is placed centrally (allele- or mutant-specific probes) and then hybridized to target DNA under conditions which permit hybridization only if a perfect match is found (Saiki et al. (1986) *Nature* 324:163); Saiki et al (1989) *Proc. Natl Acad. Sci USA* 86:6230; and Wallace et al. (1979) *Nucl. Acids Res.* 6:3543). Such allele specific oligonucleotide hybridization techniques can be used for the simultaneous detection of several nucleotide changes in different polymorphic or mutated regions of NRAS. For example, oligonucleotides having nucleotide sequences of specific allelic variants or mutants are attached to a solid support, e.g., a hybridizing membrane and this support, e.g., membrane, is then hybridized with labeled sample nucleic acid. Analysis of the hybridization signal thus can reveal the identity of the nucleotides of the sample nucleic acid.

EXPERIMENTAL PROCEDURES

The following examples are given for the purpose of illustrating the present invention and shall not be construed as being limitations on the scope of the invention.

Manufacture of multi-component pharmaceutical dosage forms with pharmaceutically acceptable polymeric compositions as described herein.

Example 1: Experimental Procedure for Preparation of Solid Dispersion Extrudate

TABLE A

| Solid Dispersion Extrudate Formulation | Procedure 1 Weight (g) for Example 2 and 3A | Procedure 2 Weight (g) for Example 3B | Procedure 3 Weight (g) for Example 4, 5 and 6 | (% w/w) |
|---|---|---|---|---|
| Solid Dispersion Extrudate | | | | |
| Compound 1 | 1200 g × 3 batches = 3600 g | 2000 g × 2 batches = 4000 g | 4400 g | 40 |
| copovidone | 1800 g × 3 batches = 5400 g | 3000 g × 2 batches = 6000 g | 6600 g | 60 |

Procedure 1:

1,200 grams of Compound 1 and 1,800 grams of copovidone (e.g., Kollidon VA64, BASF) were accurately weighed, screened with a suitable sieve (e.g. 12 mesh) and mixed using a high shear mixer (e.g., Vector GMX-25 high share mixer) operated at 325 rpm 25 rpm for about five minutes to form a pre-extrusion blended powder.

A suitable twin screw hot melt extruder (e.g. Leistritz ZSE-18HP) was set up with appropriate supporting equipment, including a cooling conveyor (e.g., Domer Cooling Conveyor) and feeder with auger (e.g., K-Tron Gravimeteric Feeder). The processing parameters were as follows:
Feed rate: 1.0 kg/hr (Range: 0.5~1.5 kg/hr);
Screw speed: 250 rpm (Range: 225~275 rpm);
Barrel temperature: zone1: 50±5° C., zone2: 90±5° C., zone3: 140±5° C., zone4: 170±5° C., Die heater: 165±10° C.

Three batches of the pre-extrusion blended powder were fed into the Hot Melt Extruder, and the resulting extrudate was cooled and milled using a suitable impact mill with hammer forward configuration (e.g., Fizmill model L1A) operated at 9,000±1,000 rpm. The milled extrudate was passed through a suitable screen (e.g., 60 mesh) manually.

Procedure 2:

2,000 grams of Compound 1 and 3,000 grams of copovidone (e.g., Kollidon VA64, BASF) were accurately weighed, screened with a suitable sieve (e.g. 12 mesh) and mixed using high shear mixing (e.g. POWREX VG-50 high share vertical granulator) operated at 325 rpm±25 rpm for about ten minutes to form a pre-extrusion blended powder.

A suitable twin screw hot melt extruder (e.g. Leistritz ZSE-18HP) was set up with appropriate supporting equipment, including a cooling conveyor (e.g., Darner End Drive Conveyor) and feeder with auger (e.g., K-Tron Gravimeteric Feeder). Processing parameters were as follows:
Feed rate: 1.0 kg/hr (Range: 0.5~1.5 kg/hr);
Screw speed: 250 rpm (Range: 225~275 rpm);
Barrel temperature: zone1: 50±5° C., zone2: 90±5° C., zone3: 140±5° C., zone4: 170±5° C., Die heater: 165±10° C.;

Two batches of the pre-extrusion blended powder were fed into the Hot Melt Extruder, and the resulting extrudate was cooled and milled using a suitable impact mill with hammer forward configuration (e.g., Fizmill model M5A) operated at 6,000 rpm±100 rpm. The milled extrudate was passed through a suitable screen (e.g., 60 mesh) manually or using automatic sieve shaker (e.g., Kason sieve shaker).

Procedure 3:

4,400 grams of Compound 1 and 6,600 grams of copovidone (e.g., Kollidon VA64, BASF) were accurately weighed and mixed using high shear mixing (e.g. Diosna P100 high share vertical granulator) operated at 200 rpm for about ten minutes to form a pre-extrusion blended powder.

A suitable twin screw hot melt extruder (e.g. Leistritz ZSE-1811P) was set up with appropriate supporting equipment, including a cooling conveyor (e.g., Nara TBC-309-DC) and feeder with auger (e.g., K-Tron Gravimeteric Feeder). Processing parameters were as follows:
Feed rate: 1.0 kg/hr (Range: 0.5~1.5 kg/hr);
Screw speed: 275 rpm (Range: 250~300 rpm);
Barrel temperature: zone1: 50±10° C., zone2: 90±10° C., zone3: 140±10° C., zone4: 175±10° C., Die heater: 175±10° C.;

The pre-extrusion blended powder was fed into the Hot Melt Extruder, and the resulting extrudate was cooled and milled using a suitable pulverizer with multi pin rotor and suitable screen (e.g., NARA Sample mill SAM with 0.5 mm screen) operated at 10,000 rpm.

Example 2: Experimental Procedure for Composition of Compound 1, 20 mg Tablet

TABLE B

| 20 mg Tablet Formulation | |
|---|---|
| Pharmaceutical Composition Formulation | (% w/w) |
| Solid Dispersion Extrudate | 20.0 |
| microcrystalline cellulose | 70.0 |
| croscarmellose sodium | 5.0 |
| colloidal silicon dioxide | 4.5 |
| magnesium stearate | 0.5 |

1,700 grams of the sieved Extrudate (from Procedure 1), 5,950 grams of microcrystalline cellulose (e.g., Avicel PH 102, FMC Biopolymer), 425.0 grams of croscarmellose sodium (Ac-Di-Sol®, FMC Biopolymer) and 382.5 grams of colloidal silicon dioxide were accurately weighed. The extrudate, croscarmellose sodium and approximately half of the microcrystalline cellulose were charged into a diffusion mixer (e.g. Bohle LM40 Bin Blender). The colloidal silicon dioxide was combined with the remaining microcrystalline cellulose and screened through a suitable screen (e.g. 40 mesh) and charged into the mixer. And then the powders were blended for 10 minutes at 25 rpm to produce the pre-blend powder. 42.5 grams of magnesium stearate (Mallinckrodt) were accurately weighed, screened with a suitable screen (e.g., 30 mesh) and blended with the pre-blend for 5 minutes at 25 rpm to produce the final blended powder. The final blended powder was compressed by a rotary tablet-making machine (e.g., Stokes B2 16 station tablet press) using 9 mm round punch to produce tablets which weight is 250 mg.

Example 3: Experimental Procedures for Composition of Compound 1,100 mg Tablet

TABLE C 100 mg Tablet Formulation

| Pharmaceutical Composition Formulation | (% w/w) |
| --- | --- |
| Solid Dispersion Extrudate | 40 |
| microcrystalline cellulose | 47.0 |
| croscarmellose sodium | 8.0 |
| colloidal silicon dioxide | 4.5 |
| Magnesium stearate | 0.5 |

3,400 grams of the sieved Extrudate (from Procedure 1), 3,995 grams of Microcrystalline cellulose (e.g., Avicel PH 102, FMC Biopolymer), 680.0 grams of croscarmellose sodium (Ac-Di-Sol®, FMC Biopolymer) and 382.5 grams of colloidal silicon dioxide were accurately weighed. The extrudate, croscarmellose sodium and approximately half of the microcrystalline cellulose were charged into a diffusion mixer (e.g. Bohle LM40 Bin Blender). The colloidal silicon dioxide was combined with the remaining microcrystalline cellulose and screened through a suitable screen (e.g. 40 mesh) and charged into the mixer. And then the powders were blended for 10 minutes at 25 rpm to produce the pre-blend powder. 42.5 grams of Magnesium stearate (Mallinckrodt) was accurately weighed, screened with a suitable screen (e.g., 30 mesh) and blended with the pre-blend for 5 minutes at 25 rpm to produce the final blended powder. The final blended powder was compressed by a rotary tablet-making machine (e.g., Stokes B2 16 station tablet press) 8 mm by 18 mm caplet punch to produce tablets which weight is 625 mg.

TABLE D 100 mg Tablet Formulation

| Pharmaceutical Composition Formulation | (% w/w) |
| --- | --- |
| Solid Dispersion Extrudate | 40 |
| microcrystalline cellulose | 47.0 |
| croscarmellose sodium | 8.0 |
| colloidal silicon dioxide | 4.5 |
| Magnesium stearate | 0.5 |

6,600 grams of the sieved Extrudate (from Procedure 2), 7,755 grams of microcrystalline cellulose (e.g., Avicel PH 102, FMC Biopolymer), 1,320 grams of croscarmellose sodium (Ac-Di-Sol®, FMC Biopolymer) and 742.5 grams of colloidal silicon dioxide (e.g., Aerosil 200, Evonik) were accurately weighed. The extrudate and the croscarmellose sodium were charged into a diffusion mixer (e.g. Showa Kagaku Kikai Kosakusho TM-60S). The colloidal silicon dioxide was combined with the microcrystalline cellulose and screened through a suitable screen (e.g. 30 mesh) and charged into the mixer. And then the powders were blended for 5 minutes at 15 rpm to produce the pre-blended powder. 82.5 grams of Magnesium stearate (Mallinckrodt) was accurately weighed, screened with a suitable screen (e.g., 30 mesh), and blended with the pre-blended powder for 2 minutes at 15 rpm to produce the final blended powder. The final blended powder was compressed by a rotary tablet-making machine (e.g. Kikusui Seisakusho, Ltd AQUARIUS) using 8 mm by 18 mm caplet punch to produce tablets which weight was 625 mg.

Example 4: Experimental Procedures for Composition of Compound 1, 20 mg Film Coated Tablet

TABLE E 20 mg Film Coated Tablet Formulation

| Pharmaceutical Composition Formulation | (% w/w) |
| --- | --- |
| Solid Dispersion Extrudate | 20.0 |
| microcrystalline cellulose | 74.0 |
| croscarmellose sodium | 5.0 |
| colloidal silicon dioxide | 0.5 |
| magnesium stearate | 0.5 |
| total core tablet | 100.0 |
| OPADRY ® Red (% of core tablet weight) | 4.2 |

2,000 grams of the extrudate (from Procedure 3), 7,400 grams of microcrystalline cellulose (e.g., Avicel PH 101, FMC Biopolymer), 500.0 grams of croscarmellose sodium (Ac-Di-Sol®, FMC Biopolymer) and 50.0 grams of colloidal silicon dioxide were accurately weighed. The colloidal silicon dioxide and a part of the microcrystalline cellulose were charged into a diffusion mixer (e.g. Bohle LM40 Bin Blender with 10 L mixing container) and blended for 5 min at 6 rpm. The powders were screened through a suitable screen (e.g. seive size 0.5 mm) and charged into a suitable diffusion mixer (e.g. Bohle LM40 Bin Blender with 40 L mixing container). The extrudate, croscarmellose sodium and the remaining microcrystalline cellulose were charged into the mixer. The powders were blended for 15 min at 6 rpm to produce the pre-blend powder. 50.0 grams of magnesium stearate (Mallinckrodt) were accurately weighed, screened with a suitable screen (e.g., seive size 1.0 mm) and blended with the pre-blend for 5 minutes at 6 rpm to produce the final blended powder. The final blended powder was compressed by a rotary tablet-making machine (e.g., Korsch XL 100) using 9 mm round punch to produce core tablets which weight is 250 mg. Subsequently, 840.0 gram of OPADRY® RED 03F45081 and 6,160 grams of purified water were added into a tank and the spray suspension was prepared by stirring. The core tablets were charged into a suitable film coating machine (e.g. Driacoater Vario 500/600) and were coated with the spray suspension until the coating amount per tablet reached 10.5 mg.

Example 5: Experimental Procedures for Composition of Compound 1, 70 mg Film Coated Tablet

TABLE F

| 70 mg Film Coated Tablet Formulation | |
|---|---|
| Pharmaceutical Composition Formulation | (% w/w) |
| Solid Dispersion Extrudate | 32.4 |
| microcrystalline cellulose | 58.6 |
| croscarmellose sodium | 8.0 |
| colloidal silicon dioxide | 0.5 |
| magnesium stearate | 0.5 |
| total core tablet | 100.0 |
| OPADRY ® Yellow (% of core tablet weight) | 3.3 |

3,241 grams of the extrudate (from. Procedure 3), 5,859 grams of microcrystalline cellulose (e.g., Avicel PH 101, FMC Biopolymer), 800.0 grams of croscarmellose sodium (Ac-Di-Sol®, FMC Biopolymer) and 50.0 grams of colloidal silicon dioxide were accurately weighed. The colloidal silicon dioxide and a part of the microcrystalline cellulose were charged into a diffusion mixer (e.g. Bohle LM40 Bin Blender with 10 L mixing container) and blended for 5 min at 6 rpm. The powders were screened through a suitable screen (e.g. seive size 0.5 mm) and charged into a suitable diffusion mixer (e.g. Bohle LM40 Bin Blender with 40 L mixing container). The extrudate, croscarmellose sodium and the remaining microcrystalline cellulose were charged into the mixer. The powders were blended for 15 min at 6 rpm to produce the pre-blend powder. 50.0 grams of magnesium, stearate (Mallinckrodt) were accurately weighed, screened with a suitable screen (e.g., seive size 1.0 mm) and blended with the pre-blend for 5 min at 6 rpm to produce the final blended powder. The final blended powder was compressed by a rotary tablet-making machine (e.g., Korsch XL 100) using a 9 mm by 14 mm oblong punch to produce core tablets which weighed 540 mg. Subsequently, 667.0 gram of OPADRY® Yellow 03F42240 and 4,889 grams of purified water were added into a tank and the spray suspension was prepared by stirring. The core tablets were charged into a suitable film coating machine (e.g. Driacoater Vario 500/600) and were coated with the spray suspension until the coating amount per tablet reached 18.0 mg.

Example 6: Experimental Procedures for Composition of Compound 1, 100 mg Film Coated Tablet

TABLE G

| 100 mg Film Coated Tablet Formulation | |
|---|---|
| Pharmaceutical Composition Formulation | (% w/w) |
| Solid Dispersion Extrudate | 40.0 |
| microcrystalline cellulose | 51.0 |
| croscarmellose sodium | 8.0 |
| colloidal silicon dioxide | 0.5 |
| magnesium stearate | 0.5 |
| total core tablet | 100.0 |
| OPADRY ® Red (% of core tablet weight) | 1.12 |
| OPADRY ® Yellow (% of core tablet weight) | 2.24 |

4,000 grams of the extrudate (from Procedure 3), 5,100 grams of microcrystalline cellulose (e.g., Avicel PH 101, FMC Biopolymer), 800.0 grams of croscarmellose sodium (Ac-Di-Sol®, FMC Biopolymer) and 50.0 grams of colloidal silicon dioxide were accurately weighed. The colloidal silicon dioxide and a part of the microcrystalline cellulose were charged into a diffusion mixer (e.g. Bohle LM40 Bin Blender with 10 L mixing container) and blended for 5 min 6 rpm. The powders were screened through a suitable screen (e.g. seive size 0.5 mm) and charged into a suitable diffusion mixer (e.g. Bohle LM40 Bin Blender with 40 L mixing container). The extrudate, croscarmellose sodium and the remaining microcrystalline cellulose were charged into the mixer. The powders were blended for 15 min at 6 rpm to produce the pre-blend powder. 50.0 grams of magnesium stearate (Mallinckrodt) were accurately weighed, screened with a suitable screen (e.g., seive size 1.0 mm) and blended with the pre-blend for 5 min at 6 rpm to produce the final blended powder. The final blended powder was compressed by a rotary tablet-making machine (e.g., Korsch XL 100) using a 9 mm by 16 mm oval punch to produce core tablets which weight is 625 mg. Subsequently, 224.0 grams of OPADRY® RED 03F45081, 448.0 grams of OPADRY® Yellow 03F42240 and 4,928 grams of purified water were added into a tank and the spray suspension was prepared by stirring. The core tablets were charged into a suitable film coating machine (e.g. Driacoater Vario 500/600) and were coated with the spray suspension until the coating amount per tablet reached 21.0 mg.

Example 7: Hot Melt Extrusion Solid Dispersion Carrier Development

Due to the limited solubility of Compound 1, an extensive amount of development work was required to produce the pharmaceutical composition of the present invention. Preformulation studies, including significant testing related to solubility, dissolution, and stability led to the initial identification of solid dispersion as a strategy for formulation development. Following the pre-formulation work, several different types of solid dispersions were evaluated. For example, complexes with resins were tried in an effort to combine slow release of drug substance without precipitation, and compositions comprising many different types of polymers (solid-based and non-solid based), surfactants, and plasticizers were also prepared, and dissolution characteristics and stability were studied. These solid dispersions were initially prepared by solvent evaporation. Later, hot melted extrusion was tried to avoid the use of solvents in manufacture.

Melt extrusion was identified as the preferred method of manufacture for solid dispersion of Compound 1 due to the improved oral bioavailability provided by the material. Further feasibility studies were carried out to investigate additional polymer types and other excipients. Optimization of polymer type and drug load during hot melt extrusion was critical in order to avoid racemization and crystallization of drug substance. Critical process parameters such as feed rate and zone temperature were also found to have a significant impact on critical product attributes (amorphous nature, chiral purity) of the solid dispersion.

Studies indicated that high levels of a chiral impurity (the S-enantiomer of Compound 1) were observed when hot melt extrusion was used for production of the solid dispersion extrudates of Compound 1. Incorporation of processing additives such as poloxamer and polysorbate failed to show any significant reduction in the level of chiral impurity formation. Table E shows the results of one study that was carried out to evaluate the potency, chiral purity, non-sink dissolution, and glass transition values of several solid dispersion compositions. Copovidone (Kollidon® VA 64) was selected as the primary polymer for dispersion due to the low level of formation of chiral impurity. The amount of Compound 1 (the desired R-isomer) was measured by high performance liquid chromatography.

TABLE E

Potency, Chiral Purity, Non-Sink Dissolution and Glass Transition (TG) Values of Screening Study Batches

| Batch Number | Composition | Potency (%) | Chiral Impurity (%) | Glass Transition (° C.) | Non-Sink AUC0→6 (µg · hr/ml) |
|---|---|---|---|---|---|
| 1 | Compound 1:Copovidone (45:55) | 99.2 | 9.49 | 111 | 366.102 |
| 2 | Compound 1:Copovidone (45:55) | 97.0 | 4.37 | 111 | 3,375.595 |
| 3 | Compound 1:Copovidone:Tween 80 (45:55:10) | NA | NA | NA | NA |
| 4 | Compound 1:Copovidone:Tween 80 (30:60:10) | 99.2 | 7.61 | 84 | 6,216.536 |
| 5 | Compound 1:Copovidone:Tween 80 (40:50:10) | 99.2 | 6.07 | 81 | 4,613.41 |
| 6 | Compound 1:Copovidone:Tween 80 (40:50:10) | 99.3 | 17.91 | 85 | NA |
| 7 | Compound 1:Eudragit ® L100-55:Triethyl Citrate (20:64:16) | 99.3 | 50.54 | 61 | 8,794.975 |
| 8 | Compound 1:Eudragit ® L100-55:Triethyl Citrate (40:54:6) | 98.8 | 50.45 | 86 | 4,409.724 |
| 9 | Compound 1:HPMCAS-M (20:80) | 100.8 | 49.29 | 93 | 4,489.699 |
| 10 | Compound 1:HPMCAS-M (40:60) | 97.0 | 45.62 | 92 | 4,088.841 |
| 11 | Compound 1:Eudragit ® E PO (30:70) | 94.5 | 48.14 | NA | 11,687.956* |
| 12 | Compound 1:Copovidone:Poloxamer 407 (40:50:10) | 96.8 | 5.68 | 109 | 3,130.347 |
| 13 | Compound 1:Copovidone:Sodium Lauryl Sulfate (40:56:4) | 98.4 | 49.32 | NA | 5,253.017 |
| 14 | Compound 1:Copovidone:Tween 80 (5:85:10) | 101.2 | 15.45 | NA | 10,726.54 |

*Dissolution testing conducted in simulated gastric fluid
NT = not tested
HPMCAS-M = hypromellose acetate succinate Non-sink dissolution testing was performed using a modified centrifuge method with biosimilar media. Briefly, approximately 4.0 mg of Compound 1 equivalent solid dispersion was accurately weighed and dispersed into a centrifuge vial with 0.5% w/w bile salt (NaTC, POPC), pH 6.5 phosphate media and stored under shaking at 250 rpm. At predetermined time points the centrifuge vial was spun at 13,000 rpm and 25 microliters of supernatant sampled without replacement for analysis by HPLC. The remaining material was briefly vortex mixed prior to returning to the incubated shaker system maintained at 37° C. in order to re-suspend material.

Samples were analyzed by differential scanning calorimetry (DSC) using a Diamond DSC. All samples were analyzed from 25° C. to 225° C. using a ramp rate of 10° C./min and sample size of approximately 8 mg. Natural glass transition temperatures were obtained by analysis of the second heating cycle.

Example 8: Processing Additives

Selected formulations from Table E (Batch 2, 5, and 12) using the Kollidon® VA 64 carrier were placed on an accelerated (40° C./75% RH) open dish stability for one month and examined by scanning electron microscopy to assess potential surface recrystallization. Surface images of compositions containing processing additives such as Tween 80 and Poloxamer 407 showed indications of recrystallization. The magnitude of this behavior was significantly influenced by the type of additive selected. Compositions containing Poloxamer 407 exhibited substantial surface recrystallization over the storage period, while formulations using Tween 80 showed only the minimal potential recrystallization. Solid dispersion produced without a processing aid exhibited excellent amorphous stability, showing no indications of recrystallization.

Kollidon® VA 64 compositions with and without a non-ionic surfactant, Poloxamer 407, from Table E (Batch 2 and 12) were also evaluated for oral bioavailability enhancement in cynomolgus monkeys. The compositions were administered to achieve a target dose of 25 mg/kg body weight of the Compound 1 (R-enantiomer). Formulation development results showed that these compositions provided similar physiochemical properties and also yielded similar non-sink dissolution behavior. A second batch containing Poloxamer 407 was produced for this dosing experiment using a ZSE-18 mm extruder (the original batches were produced using a Nano-16 extruder). Additionally, to enhance disintegration of the compositions, all dosed capsules contained Polyplasdone XL-10 (Crospovidone) at a loading of 4.0%. This second batch yielded similar potency and chiral impurity levels as previously described for equivalent formulations; however presented a significantly reduced oral bioavailability in comparison to the Poloxamer 407 free formulation (Batch 2). The formulations studied presented relative oral bioavailabilities of 104%±33% and 38%±19% for the Poloxamer 407 free and Poloxamer 407 containing formulations respectively.

Example 9: Bioavailability Study

Tablet and capsule dosage forms were prepared to support oral bioavailability in cynomologus monkeys. Formulations for each batch are presented in Table F below along with composition attributes.

TABLE F

| Material | Compound 1 Tablets, 100 mg | Compound 1 Capsules, 100 mg |
|---|---|---|
| Extrudate 400 mg/g | 40.0% | 86.24% |
| Microcrystalline cellulose, Avicel PH 102 | 45.0% | 6.76% |
| Polyplasdone XL | — | 5.0% |
| Croscarmellose Sodium, Ac-Di-Sol | 10.0% | — |
| Colloidal Silicon Dioxide, Aerosil 200 | 4.5% | 2.00 |
| Magnesium Stearate | 0.5% | — |

TABLE G

Solid Dispersion Composition Attributes

| Metric | Compound 1 Tablets, 100 mg Value | Compound 1 Capsules, 100 mg Value |
|---|---|---|
| Potency | 104.7% | 103.9% |
| Total Impurities | 0.66% | 0.66% |
| RRT 0.79 | 0.16% | 0.16% |
| RRT 0.84 | 0.05% | 0.05% |
| RRT 0.84 | 0.027% | 0.027% |
| Chiral Impurity | 3.47% | 3.5% |
| Amorphous Character | Amorphous | Amorphous |

Tablets prepared to support the animal trial were adjusted based on the measured potency and chiral purity of the extrudate to achieve a target delivery of 100 mg of Compound 1. Potency values for both the tablet and capsule tested at approximately 103.5% to account for the measured chiral impurity level of the extrudate. The composition attributes (Table G) associated with the chemical purity indicated that the dosage forms produced provided a robust product with no significant decomposition induced by the manufacturing process.

Figure 2:
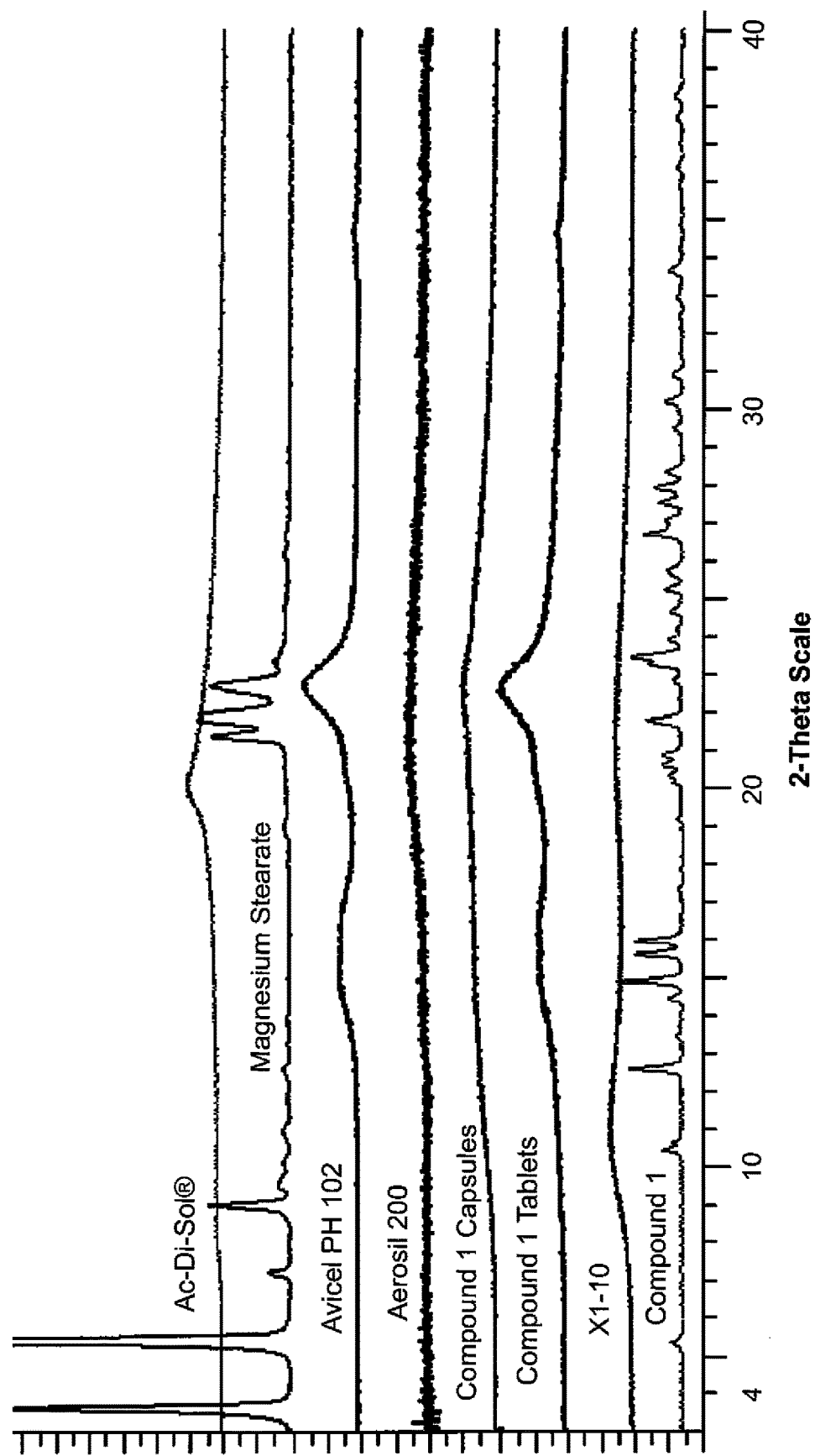
FIG. 2 is an X-ray powder diffraction (XRPD) of Compound 1 tablets, capsules and constituent raw materials used in the manufacture of animal trial and stability samples.

The amorphous nature of the solid dispersion compositions was assessed by XRPD, with representative diffraction patterns for each constituent raw material and the respective dosage forms presented in FIG. 2. Results show that only magnesium stearate and crystalline Compound 1 produced characteristic peaks indicative of their crystalline nature. Other materials in the composition were whown to be amorphous due to the absence of characteristic peaks associated with crystalline structure. Testing of both compositions showed that the materials prepared for the study were amorphous, demonstrating amorphous halos characteristic of the major amorphous excipients in the formulations. Based on these results; compositions prepared were shown to be amorphous.

Dissolution behavior of the compositions produced was also assessed using sink dissolution, with profiles presented in FIG. 3 (diamond=tablet; square=capsule). Compound 1 tablets showed rapid dissolution. Capsule formulations showed muted release relative to the tablet formulation.

Preclinical bioavailability studies were conducted in cynomolgus monkeys (n=3) at an approximate dose of 25 mg/kg to assess oral bioavailability of tablet and capsule dosage forms prepared by hot melt extrusion and spray drying. Melt extruded compositions were shown to provide superior AUC values compared to spray dried formulations. Mean plasma profiles for each of the formulations are presented in FIG. 4.

Example 10: High Shear Mixing Reduces Potency Variation

Due to the continuous nature of the extrusion process potency variation must be kept to a minimum to yield a robust manufacturing procedure. During the initial development runs significant intra-batch potency variation was observed that could not be accounted for based on a mass balance and suggested heterogeneity of the feed stock during processing. For the preparation of the initial development batches a bag blending procedure was used where Compound 1 and Kollidon® VA 64 were added into a polyethylene bag and manually agitated for a period of up to 5 minutes. Once potency variability within batches was observed, a procedural change was made to prepare feed stock material by screening both components through an 18-mesh screen and mixing in a high shear mixer for two minutes at 1,500 rpm. A retroactive comparison of the potency values, presented in FIG. 5, showed that the use of high shear mixing significantly reduced potency variation.

Example 11: Tablet Disintegration

For the preliminary disintegration study tablets were manually prepared at 100 mg strength using 10.0 mm round, standard concave tooling at compression forces of 4.8, 6.9, 6.2 and 13.9 kN, respectively from blend batches having extrudate levels of 62.5% and 80%. Forces used for compression were selected to yield tablets with approximate hardness values of 10.0±5.0 kP. Disintegration testing was conducted using simulated gastric fluid to assess performance. Results from testing the prototype batches showed limited disintegration, with measured times greater than 180 min for the samples selected. Additional optimization was conducted by sequentially reducing the solid dispersion loading and also modifying the grade of diluent and superdisintegrant used. For this study, four formulation modifications and two tooling types were investigated, as presented in Table H. Results showed that reductions in solid dispersion loading from 62.5% to 50% provided a significant improvement in disintegration performance, with further improvement observed when further reducing to 40%.

TABLE H

Disintegration Optimization Studies for Compound Tablets, 100 mg

| Sample No. | Formulation Variation | Force (kN) | Hardness (kP) | Disintegration Time (min) |
|---|---|---|---|---|
| 1 | 62.5% extrudate; 22.5% MCC, 10% XL10 10 mm round, standard concave | 4.8 | 14.7 | >180 |
| 2 | 50% extrudate; 35% MCC, 10% XL10 10 mm round, standard concave | 6.4 | 10.1 | 21.3 |

TABLE H-continued

Disintegration Optimization Studies for Compound Tablets, 100 mg

| Sample No. | Formulation Variation | Force (kN) | Hardness (kP) | Disintegration Time (min) |
|---|---|---|---|---|
| 3 | 50% extrudate; 35% MCC, 10% Ac-Di-Sol 10 mm round, standard concave | 6.4 | 9.2 | 0.3 |
| 4 | 50% extrudate; 35% MCC: S1500, 10% XL10 10 mm round, standard concave | 7.7 | 8.7 | 24.8 |
| 5 | 40% extrudate; 45% MCC, 10% Ac-Di-Sol 8 × 18 mm Caplet Shaped Tooling | 3.5 | 8.6 | 0.3 |
| 6 | 50% extrudate; 35% MCC, 10% Ac-Di-Sol 8 × 18 mm Caplet Shaped Tooling | 6.4 | 11.5 | 0.4 |

Example 12: Compression Optimization

Compression robustness of each formulation was studied using a manual tablet press to assess the impact of critical process parameters (dwell time and compression force) and disintegration time and tablet hardness. For this study a two level factorial design was implemented, varying the levels of each critical process parameter as shown in Table I.

Critical product attributes for each formulation condition were evaluated and the results are presented in Table I. Both formulations exhibited tablet hardness values that were dependent on both compression force and dwell time. Disintegration behavior for both formulations was rapid, with measured disintegration times less than 5 min for all tablets studied.

TABLE I

Compression Optimization Study of 100 mg Tablets

| Formulation | | | | |
|---|---|---|---|---|
| 50% solid dispersion extrudate 35% avicel PH 102 10% Ac-Di-Sol 4.5% Colloidal Silicon Dioxide 0.5% Magnesium Stearate | | 40% solid dispersion extrudate 45% avicel PH 102 10% Ac-Di-Sol 4.5% Colloidal Silicon Dioxide 0.5% Magnesium Stearate | | |
| Run # | Dwell Time (s) | Compression Force (kN/psi) | Dwell Time (s) | Compression Force (kN) |
| 1 | 0 | 6.4/1,700 | 0 | 3.5/1,000 |
| 2 | 0 | 8.5/2,200 | 0 | 5.6/1,500 |
| 3 | 0 | 6.4/1,700 | 5 | 3.5/1,000 |
| 4 | 0 | 8.5/2,200 | 5 | 5.6/1,500 |

Example 13: Treatment of Patients

"An Open-Label, Phase I, Dose Escalation Study of Compound 1 in Patients With Relapsed or Refractory Solid Tumors Followed by a Dose Expansion Phase in Patients with Metastatic Melanoma."

This is a phase 1, multicenter, nonrandomized, open-label, dose escalation study. This study is conducted in patients ≥18 years of age with advanced solid tumors (excluding lymphoma) (Dose Escalation and PK Expansion cohort) or locally advanced, metastatic, and/or unresectable melanoma (melanoma expansion cohorts) and additional solid tumors.

The QW arm tests an initial Compound 1 dose of 400 mg once weekly (on Days 1, 8, 15, and 22) in a 28-day cycle. Patients will fast (with the exception of water) for at least 2 hours before and at least 2 hours after taking their dose of Compound 1. Patients may continue treatment for additional cycles until disease progression, unacceptable toxicity, or the patient discontinues for any other reason. The maximum duration of treatment will be 12 months unless it is determined that a patient would derive benefit from continued therapy beyond 12 months.

QW Dose Expansion Phase: Once the MTD and/or RP2D of QW Compound 1 has been determined, the study will continue to a QW Dose Expansion phase. The Dose Expansion phase will enroll approximately 16 patients (up to 16 patients per cohort), one cohort of patients with locally advanced, metastatic, and/or unresectable NRAS mutation positive melanoma naive to MEK or RAF inhibitors, and one cohort of patients with BRAF mutionation positive thyroid, colorectal or non-small cell lung cancers. Individual Dose Expansion cohorts may be opened or closed sequentially or in parallel at the sponsor's discretion, based on emerging data.

Patients in the QW Dose Expansion phase will take Compound 1 orally QW for a 28-day cycle until disease progression, unacceptable toxicity, or the patient discontinues for any other reason. The maximum duration of treatment will be 1 year unless it is determined that a patient would derive benefit from continued therapy beyond 12 months.

Example 14: Methods for Measuring BRAF and/or NRAS Markers

BRAF PCR based Assay (Vendor: Qiagen; Catalog#: 870801) The BRAF RGQ PCR Kit v2 combines two technologies, ARMS® and Scorpions®, to detect mutations in real-time PCR assays. This assay detects BRAFV600 mutations V600E (GAG) and V600E complex (GAA), V600D (GAT), V600K (AAG), V600R (AGG). The kit detects the presence of the V600E (GAG) and V600E complex (GAA) but does not distinguish between them.

Arms

Specific mutated sequences are selectively amplified by allele specific primer designed to match a mutated DNA.

Scorpions

Detection of amplification is performed using Scorpions. Scorpions are PCR primer covalently linked to a fluorescently labeled probe (i.e. FAM™ or HEX™) and a quencher. During PCR when the probe is bound to the amplicon, the fluorophore and quencher become separated resulting in an increase in fluorescence signal.

Procedure

The BRAF RGQ PCR Kit v2 comprises a two-step procedure. In the first step, the control assay is performed to assess the total amplifiable BRAF DNA in a sample. In the second step, both the mutation and control assays are performed to determine the presence or absence of mutant DNA.

Control Assay

The control assay, labeled with FAM, is used to assess the total amplifiable BRAF DNA in a sample. The control assay amplifies a region of exon 3 of the BRAF gene.

The primers and Scorpion probe are designed to amplify independently of any known BRAF polymorphisms.

Mutation Assays

Each mutation assay contains a FAM-labeled Scorpion probe and an ARMS primer for discrimination between the wild-type DNA and a specific mutant DNA.

Data Analysis: ΔCt Method

Scorpions real-time assays uses the number of PCR cycles necessary to detect a fluorescent signal above a background signal as a measure of the target molecules present at the beginning of the reaction. The point at which the signal is detected above background fluorescence is called the 'cycle threshold' (Ct).

Sample ΔCt values are calculated as the difference between the mutation assay Ct and control assay Ct from the same sample. Samples are classed as mutation positive if they give a ΔCt less than the Cut-Off ΔCt value for that assay. Above this value, the sample either contains less than the percentage of mutation able to be detected by the kit (beyond the limit of the assays), or the sample is mutation negative.

When using ARMS primers some inefficient priming could occur, giving a very late background Ct from DNA not containing a mutation. All ΔCt values calculated from background amplification are greater than the cut off ΔCt values and the sample is classed mutation negative.

For each sample, the ΔCt values are calculated as follows, ensuring that the mutation and control Ct values are from the same sample:

$\Delta Ct = \{\text{sample mutation } Ct\} - \{\text{sample control } Ct\}$

Sample control Ct can range between 27-33
Sample mutation Ct can range between 15-40
Acceptable ΔCt for the mutant call is <6 or 7
Methods for measuring NRAS mutations are similar to those described above for BRAF. Qiagen NRAS assay for the detection of NRAS Q61 mutations includes:
Q61K (181 C>A)
Q61R (182 A>G)

What is claimed:

1. A pharmaceutical composition comprising:
   (1) 10% to 50% w/w of a solid dispersion extrudate comprising:
      (a) about 40% w/w of (R)-2-(1-(6-amino-5-chloropyrimidine-4-carboxamido)ethyl)-N-(5-chloro-4-(trifluoromethyl)pyridin-2-yl)thiazole-5-carboxamide, or a pharmaceutically acceptable salt thereof, and
      (b) about 60% w/w of copovidone; and
   (2) 90% to 50% w/w of one or more pharmaceutically acceptable excipients,
   wherein the solid dispersion extrudate comprises <3% w/w of (S)-2-(1-(6-amino-5-chloropyrimidine-4-carboxamido)ethyl)-N-(5-chloro-4-(trifluoromethyl)pyridin-2-yl)thiazole-5-carboxamide.

2. The pharmaceutical composition of claim 1, which comprises croscarmellose sodium.

3. The pharmaceutical composition of claim 1, which comprises colloidal silicon dioxide.

4. The pharmaceutical composition of claim 1, which comprises magnesium stearate.

5. The pharmaceutical composition of claim 1, which comprises microcrystalline cellulose.

6. A process for preparing a pharmaceutical composition of claim 1, which comprises:
   (i) extruding a mixture of (R)-2-(1-(6-amino-5-chloropyrimidine-4-carboxamido)ethyl)-N-(5-chloro-4-(trifluoromethyl)pyridin-2-yl)thiazole-5-carboxamide, or a pharmaceutically acceptable salt thereof, and copovidone to form a solid dispersion extrudate; and
   (ii) blending the resulting solid dispersion extrudate with one or more pharmaceutically acceptable excipients,
   wherein the solid dispersion extrudate comprises <3% w/w of (S)-2-(1-(6-amino-5-chloropyrimidine-4-carboxamido)ethyl)-N-(5-chloro-4-(trifluoromethyl)pyridin-2-yl)thiazole-5-carboxamide.

* * * * *